United States Patent
Brandt et al.

(10) Patent No.: US 6,946,471 B2
(45) Date of Patent: Sep. 20, 2005

(54) 2-(2,6-DICHLOROPHENYL)-DIARYLIMIDAZOLES

(75) Inventors: Michael Brandt, Iffeldorf (DE); Georg Fertig, Penzberg (DE); Hans-Willi Krell, Penzberg (DE); Thomas von Hirschheydt, Penzberg (DE); Edgar Voss, Staufenberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/848,611

(22) Filed: May 18, 2004

(65) Prior Publication Data

US 2004/0214874 A1 Oct. 28, 2004

Related U.S. Application Data

(62) Division of application No. 10/408,539, filed on Apr. 7, 2003, now Pat. No. 6,790,852.

(30) Foreign Application Priority Data

Apr. 18, 2002 (EP) ............................................. 02008228

(51) Int. Cl.$^7$ .......................................... A61K 31/506
(52) U.S. Cl. ..................................................... 514/275
(58) Field of Search .......................................... 514/275

(56) References Cited

FOREIGN PATENT DOCUMENTS

WO WO 96/18626 6/1996
WO WO 01/44154 6/2001

OTHER PUBLICATIONS

Gust et al., Eur. J. Med. Chem., 28, pp. 103–115 (1993).

Somei et al., Chem. Pharm. Bull., 29, pp. 3145–3157 (1981).

Karl et al., J. Med. Chem., 31., pp. 72–83 (1988).

Leeper et al., Pestic. Chem., Proc. Int. Congr. Pestic. Chem. $2^{nd}$, Tahoori, A. (Ed.) 5, pp. 125–139 (1972).

*Primary Examiner*—Richard L. Raymond
(74) *Attorney, Agent, or Firm*—George W. Johnston; Patricia S. Rocha-Tramaloni; Brian C. Remy

(57) ABSTRACT

This invention is directed to compounds of formula (I), which are valuable therapeutics for the treatment of cancer and cancer related diseases.

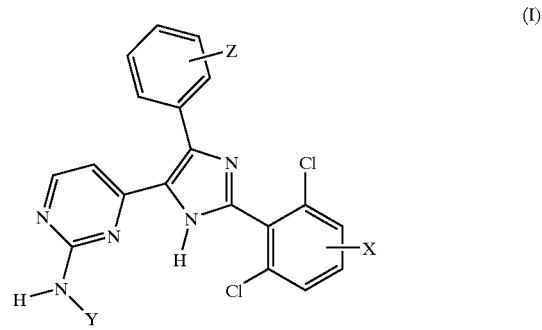

16 Claims, No Drawings

2-(2,6-DICHLOROPHENYL)-DIARYLIMIDAZOLES

PRIORITY TO RELATED APPLICATIONS

This application is a division of U.S. application Ser. No. 10/408,539, filed Apr. 7, 2003, now U.S. Pat. No. 6,790,852, which claims the benefit of European Application No. 02008228.5, filed Apr. 18, 2002; each of which is incorporated herein by reference in its entirety.

FIELD OF THE INVENTION

This invention relates to new 2-(2,6-dichlorophenyl)-diarylimidazoles and their pharmaceutically acceptable salts. These compounds are protein-tyrosine kinase inhibitors, especially inhibitors of c-met kinase and are therefore excellent therapeutics for the treatment of cancer. The invention relates also to pharmaceutical compositions that contain these new compounds as active agents for the treatment of cancer and cancer related diseases.

BACKGROUND OF THE INVENTION

Protein-tyrosine kinases (PTKs), enzymes that catalyse the transfer of the γ-phosphate of ATP to tyrosine residues of protein substrates, are critical components of signalling pathways that control cellular proliferation and differentiation. PTKs are subdivided into two large families, receptor tyrosine kinases (RTKs) and non-receptor tyrosine kinases (NRTKs). RTKs span the plasma membrane and contain an extra-cellular domain, which binds ligand, and an intracellular portion, which possesses catalytic activity and regulatory sequences. Most RTKs, like the hepatocyte growth factor receptor c-met, possess a single polypeptide chain and are monomeric in the absence of ligand. Ligand binding to the extracellular portion of RTKs, dimerizes monomeric receptors, resulting in autophosphorylation of specific tyrosine residues in the cytoplasmic portion (for review see: Blume-Jensen, P., and Hunter, T., Nature 411 (2001) 355–365; Hubbard, S. R., et al., J. Biol. Chem. 273 (1998) 11987–11990; Zwick, E., et al., Trends Mol. Med. 8 (2002) 17–23). In general, tyrosine autophosphorylation either stimulates the intrinsic catalytic kinase activity of the receptor or generates recruitment sites for downstream signalling proteins containing phosphotyrosine-recognition domains, such as the Src homology 2 (SH2) domain or the phosphotyrosine-binding (PTB) domain.

Protein tyrosine kinases play a critical role in intracellular signal transduction pathways leading to diverse cellular responses such as proliferation, apoptosis and differentiation. Consequently, these enzymes have become primary targets for the development of novel therapeutics designed to block cancer cell proliferation, metastasis, angiogenesis and promote apoptosis. The strategy that has progressed farthest in clinical development is the use of monoclonal antibodies to target growth factor receptor tyrosine kinases. The use of small molecule tyrosine kinase inhibitors however could have significant theoretical advantages over monoclonal antibodies. Small molecule inhibitors could have better tissue penetration, could have activity against intracellular targets and mutated targets and could be designed to have oral bioavailability. Several lead compounds have shown promising activity against such targets as the EGFR, the vascular endothelial cell growth factor receptor and bcr-abl.

The hepatocyte growth factor receptor c-met was first identified as an activated oncogene in an N-methyl-N'-nitrosoguanidinic treated human osteogenic sarcoma cell line (MUNG-HOS) by its ability to transform NIH 3T3 mouse fibroblasts. The receptor encoded by the c-met protooncogene (located on chromosome 7) is a two-chain protein composed of 50 kda(α) chain disulfide linked to a 145 kda(β) chain in an αβ complex of 190 kDa. The α chain is exposed at the cell surface while the β chain spans the cell membrane and possesses an intracellular tyrosine kinase domain. The presence of this intracellular tyrosine kinase domain groups c-met as a member of the receptor tyrosine kinase (RTK) family of cell surface molecules.

Hepatocyte growth factor (HGF), also known as Scatter Factor (SF), is a multifunctional cytokine that elicits diverse responses in different cells and tissues. Since its initial discovery and characterisation HGF/SF has been the subject of intense research, particularly regarding its role in cancer development and progression. Much evidence now points to its role as a regulator of carcinogenesis, cancer invasion and metastasis (for review see: Herynk, M. H., and Radinsky, R., In Vivo 14 (2000) 587–596; Jiang, W., et al., Crit. Rev. Oncol. Hematol. 29 (1999) 209–248; Longati, P., et al., Curr. Drug Targets 2 (2001) 41–55; Maulik, G., et al., Cytokine-Growth Factor Rev. 13 (2002) 41–59; Parr, C., and Jiang, W. G., Histol. Histopathol. 16 (2001) 251–268.

HGF/SF binds to and induces tyrosine phosphorylation of the mature c-met receptor β chain. Such events are thought to promote binding of intracellular signalling proteins containing src homology (SH) regions such as PLD-γ, Ras-GAP, PI-3 kinase pp60$^{c-src}$ and the GRB-2 Socs complex to the activated receptor. Each SH2-containing protein may activate a different subset of signalling phosphopeptides, thus eliciting different responses within the cell.

C-met mutations have been well-described in hereditary and sporadic human papillary renal carcinomas and have been reported in ovarian cancer, childhood hepatocellular carcinoma, metastatic head and neck squamous cell carcinomas, and gastric cancer. C-met is also over-expressed in both non-small cell lung cancer and small cell lung cancer cells, in breast, colon and prostate tumors. Since c-met appears to play an important role in oncogenesis of a variety of tumors, various inhibition strategies have been employed to therapeutically target this receptor tyrosine kinase.

The usefulness of inhibiting the protein-tyrosine kinase c-met for inhibiting tumor growth and invasion has been shown in many well documented preclinical experiments (e.g., Abounader, R., et al., J. Natl. Cancer Inst. 91 (1999) 1548–1556; Laterra, J., et al., Lab. Invest. 76 (1997) 565–577; Tomioka, D., Cancer Res. 61 (2001) 7518–7524; Wang, R., et al., J. Cell Biology 153 (2001) 1023–1033).

WO 96/18626 discloses inhibitors of tyrosine kinases and c-met kinase which are derivatives of 2-(2,6-dichlorophenyl)-4-phenyl-5-(pyridin-4yl)-1H-imidazole (examples 5, 6 and 55). However, they show unfavorable cytochrome P450 interactions and also some undesirable physical properties like low bioavailability.

It has now been found, that the 2-(2,6-dichlorophenyl)-4-phenyl-5-(pyrimidin-4yl)-1H-imidazoles according to this invention avoid these disadvantages and show improved properties as protein-tyrosine kinase inhibitors.

It is, therefore, desirable to have a compounds that avoid the above-described disadvantageous and show improved properties as protein-tyrosine kinase inhibitors.

SUMMARY OF THE INVENTION

It was surprisingly found that the pharmaceutical and anti-tumorigenic activities, due to the c-met inhibition of the compounds according to this invention are especially provided by the presence of a 2,6-dichlorophenyl residue in 2-position of the imidazole ring.

The invention relates to compounds of formula (I)

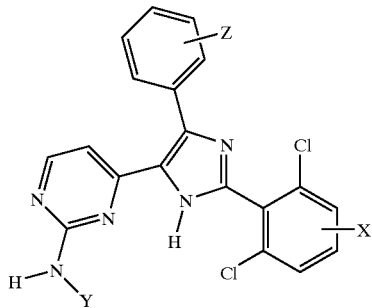

(I)

wherein

X is hydrogen; $OR^1$; $SR^2$; $(SO)R^2$; $(SO_2)R^2$; or a group $A^1$—Q;
$A^1$ represents a $C_1$–$C_3$-alkylen group;
Q is $OR^1$; $SR^2$; $SOR^2$; $SO_2R^2$; $NR^3R^4$; $NHCH_2CH_2NR^3R^4$ or halogen;
$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl or a group $A^1$—$Q^1$;
$Q^1$ represents $C_1$–$C_2$-alkoxy; cyano; carboxyl; $C_1$–$C_6$-alkoxycarbonyl; carboxamide; —CO—$NR^3R^4$; $C_1$–$C_6$-alkylsulfanyl; $C_1$–$C_6$-alkylsulfenyl; $C_1$–$C_6$-alkylsulfonyl and in case that $A^1$ represents an 1,2-ethylen- or 1,3-propylen group, $Q^1$ is hydroxy or $NR^3R^4$;
$R^2$ is $C_1$–$C_6$-alkyl; dimethylphosphonylmethyl; 2,3-epoxy-1-propyl; 2,3-dihydroxy-1-propyl; 2,2-dimethyl-1,3-dioxolan-4-ylmethyl or $A^1$—$Q^1$;
$R^3$ and $R^4$ are independently selected from the group consisting of hydrogen; $C_1$–$C_6$-alkyl or together form a 5 to 7 membered, saturated or unsaturated ring, optionally substituted by a methyl group and containing one or two heteroatoms, independently selected from N or O;
Y is hydrogen or a group $A^2$—R;
$A^2$ is unsubstituted $C_1$–$C_5$-alkylen, or substituted $C_1$–$C_5$-alkylen substituted by $C_1$–$C_6$-alkyl; phenyl or by hydroxy;
R represents hydroxy; linear or branched $C_1$–$C_6$-alkoxy; amino; dimethylamino; diethylamino; t-butyloxycarbonylamino; carboxyl; $C_1$–$C_6$-alkoxycarbonyl; triazolyl; cyano; piperidino; 1-pyrrolidinyl; morpholino; 4-methylpiperazin-1-yl; O—$A^1$—$NR^3R^4$; S—$A^1$—$NR^3R^4$; 4-carboxyphenyl; furan-3-yl; thiophen-2-yl or 3-methylthiophen-2-yl;
Z represents one or two substituents independently selected from the group consisting of halogen; hydroxy; allyloxy; methyl; $C_1$–$C_5$-alkoxy; methoxymethoxy; (2-methoxyethoxy)methyloxy; methylthio; ethoxymethoxy; methylendioxy; ethynyl; trimethylsilylethynyl and benzyloxy which is optionally substituted by halogen; methoxy; cyano; nitro; methylendioxy; carboxy or ethoxy;
or its pharmaceutically acceptable salt thereof

DETAILED DESCRIPTION OF THE INVENTION

Preferred $C_1$–$C_6$-alkyl groups with regard to $R^1$, $R^2$, $R^3$, $R^4$ and $A^2$ are methyl, ethyl and propyl.

Preferred $C_1$–$C_6$-alkoxy groups with regard to $Q^1$, R and Z are methoxy, ethoxy or isopropyloxy.

Preferred ring systems, formed by $R^3$ and $R^4$ together represent 1-pyrrrolidinyl-, piperidino-, morpholino- or 4-methylpiperazin-1-yl.

Preferably X=$A^1$—Q represents —$CH_2OH$ or —$CH_2$—$CH_2$—OH.

Preferably X=—O—$A^1$—$Q^1$ is —O—$CH_2$—$CH_2$—OH; —O—$CH_2$—COOH or —O—$CH_2$—CN.

Preferred groups for Y=$A^2$—R are 2-hydroxyethyl; 3-hydroxypropyl, 2-methoxyethyl; 3-methoxypropyl; (R)-2,3-dihydroxy-1-propyl; (S)-2,3-dihydroxy-1-propyl; (R)-3-hydroxybutyl; (S)-3-hydroxybutyl; 2-morpholinoethyl; 3-morpholinopropyl; $(CH_2)_3COOH$; 2-(4-methylpiperazin-1-yl)ethyl; 3-Hydroxy-2,2-dimethylpropyl; 3-hydroxy-1-phenylpropyl; 3-tert-butyloxyethyl; 2-aminoethyl; 3-aminopropyl; 4-aminobutyl; 2-(N,N-dimethylamino)ethyl; 3-(N,N-dimethylamino)propyl; 3-(pyrrolidin-1-yl)propyl; $CH_2COOH$; $(CH_2)_2COOH$; $CH(C_2H_5)COOH$; $(CH_2)_3COOC(CH_3)_3$; $(CH_2)_2$—N—$COOC(CH_3)_3$; $(CH_2)_3$—N—$COOC(CH_3)_3$; $(CH_2)_2$—O—$(CH_2)_2$—$N(CH_3)_2$; $(CH_2)_2$—O—$(CH_2)_2$—$NH_2$; $(CH_2)_2$—S—$(CH_2)_2$—$N(CH_3)_2$; $(CH_2)_2$—S—$(CH_2)_3$—$N(CH_3)_2$; $(CH_2)_3$—S—$(CH_2)_2$—$N(CH_3)_2$; $(CH_2)_3$—S—$(CH_2)_3$—$N(CH_3)_2$; (1,2,4-triazol-1-yl)ethyl; 3-(1,2,4-triazol-3-yl)propyl.

Halogen is fluorine, chlorine, bromine or iodine.

Preferably, the substituent X is located in the 4-position of the phenyl ring, whereas the substituent Z is preferably located in the 3- or 4-position. If Z represents benzyloxy or a substituted benzyloxy group, Z is preferably located in the 3-position.

Especially preferred are compounds of formula (I) and pharmaceutically acceptable salts thereof, wherein Z is selected from the group consisting of 3-chloro; 4-chloro; 3-bromo; 3-iodo; 3-ethynyl; 3-methoxymethoxy; 3-(2-methoxyethoxy)methyloxy; 3-methylthio; 3-ethoxymethoxy; 3,4-methylendioxy or 3-benzyloxy, which is optionally substituted by halogen; methoxy; cyano; nitro; methylendioxy; carboxy or ethoxy.

Also especially preferred are compounds of formula (I), wherein

X is hydrogen; $OR^1$; $(SO)CH_3$; $(SO_2)CH_3$; or a group $CH_2$—Q;
Q is OH; $NR^3R^4$ or $NHCH_2CH_2NR^3R^4$;
$R^1$ is selected from the group consisting of hydrogen; dimethylphosphonylmethyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl or a group $A^1$—$Q^1$;
$A^1$ represents a methylene, ethylene or propylene group;
$Q^1$ is cyano; carboxyl; carboxamide; —CO—$NR^3R^4$; and in case that $A^1$ represents an 1,2-ethylen- or 1,3-propylen group, then $Q^1$ can be cyano; carboxyl; carboxamide; hydroxy or $NR^3R^4$;
$R^3$ and $R^4$ are independently selected from the group consisting of hydrogen, methyl, ethyl, 2-morpholinoethyl or together form a 5 to 7 membered, saturated or unsaturated ring, optionally substituted by a methyl group and containing one or two heteroatoms, independently selected from N or O;
Y represents 2-hydroxyethyl; 3-hydroxypropyl; 2-methoxyethyl; 3-methoxypropyl; (R)-2,3-dihydroxy-1-propyl; (S)-2,3-dihydroxy-1-propyl; (R)-3-hydroxybutyl; (S)-3-hydroxybutyl; 3-Hydroxy-2,2-dimethylpropyl;

2-morpholinoethyl; 3-morpholinopropyl; 2-(4-methylpiperazin-1-yl)ethyl; 3-hydroxy-1-phenylpropyl; 2-aminoethyl; 3-aminopropyl; 4-aminobutyl; 2-(N,N-dimethylamino)ethyl; 3-(N,N-dimethylamino)propyl; 3-(pyrrolidin-1-yl)propyl; $CH_2COOH$; $(CH_2)_2COOH$; $(CH_2)_3COOH$; $CH(C_2H_5)COOH$; $(CH_2)_2—O—(CH_2)_2—N(CH_3)_2$; $(CH_2)_2—O—(CH_2)_2—NH_2$; $(CH_2)_2—S—(CH_2)_2—N(CH_3)_2$; $(CH_2)_2—S—(CH_2)_3—N(CH_3)_2$; $(CH_2)_3—S—(CH_2)_2—N(CH_3)_2$ or $(CH_2)_3—S—(CH_2)_3—N(CH_3)_2$;

Z is selected from the group consisting of 3-chloro; 4-chloro; 3-bromo; 3-iodo; 3-ethynyl; 3-methoxymethoxy or 3-benzyloxy which is optionally substituted by halogen; methoxy; cyano; nitro; methylendioxy; carboxy or ethoxy;

with the substituent X being located in the 4-position of the phenyl ring, and a pharmaceutically acceptable salt thereof.

Also especially preferred are compounds of formula (I), wherein

X is hydrogen; $OR^1$; $(SO)CH_3$; $(SO_2)CH_3$; or a group $CH_2—Q$;

Q is OH; $NR^3R^4$ or $NHCH_2CH_2NR^3R^4$;

$R^1$ is selected from the group consisting of hydrogen; dimethylphosphonylmethyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl or a group $A^1—Q^1$;

$A^1$ represents a methylene, ethylene or propylene group;

$Q^1$ represents cyano, carboxyl; and in case that $A^1$ represents an 1,2-ethylen- or 1,3-propylen group, then $Q^1$ can be cyano, carboxyl, hydroxy or $NR^3R^4$;

$R^3$ and $R^4$ are independently selected from the group consisting of hydrogen, methyl, ethyl or together form a 5 to 7 membered, saturated or unsaturated ring, optionally substituted by a methyl group and containing one or two heteroatoms, independently selected from N or O;

Y is 2-hydroxyethyl; 3-hydroxypropyl; (R)-2,3-dihydroxy-1-propyl; (S)-2,3-dihydroxy-1-propyl; 2-morpholinoethyl; 3-morpholinopropyl; 2-(4-methylpiperazin-1-yl)ethyl; 2-aminoethyl; 3-aminopropyl; 2-(N,N-dimethylamino)ethyl; 3-(N,N-dimethylamino)propyl or 3-(pyrrolidin-1-yl)propyl;

Z is selected from the group consisting of 3-chloro; 4-chloro; 3-bromo; 3-iodo; 3-ethynyl; 3-methoxymethoxy or 3-benzyloxy which is optionally substituted by halogen; methoxy or cyano;

with the substituent X being located in the 4-position of the phenyl ring, and a pharmaceutically acceptable salt thereof.

Most preferred are the compounds of formula (I), as defined by the non-limiting examples H1.1.1 till H17.3.5 and pharmaceutically acceptable salts thereof.

Formula (I) represents 2-(2,6-dichlorophenyl)-4-phenyl-5-(4-pyrimidinyl)-1H-imidazoles which are the tautomers of 2-(2,6-dichlorophenyl)-5-phenyl-4-(4-pyrimidinyl)-1H-imidazoles. Both tautomers represent the same structure, their nomenclature may be used interchangeably and both tautomers are part of the invention. The compounds of the present invention may contain one or more chiral centers and may occur as racemates, racemic mixtures, and as individual diastereomers, with all possible isomers, including optical isomers, being included within the scope of the present invention.

Compounds of formula (I) can be prepared by reacting a compound of formula (VI) or (VII) with an amine Y—$NH_2$, wherein X, Y and Z have the significance as defined herein before, at a temperature in the range of 80 to 180° C. and subsequent isolation of the compound. Preferably, stoichiometric amounts or an excess of the amines are used. The reaction can be performed without solvent or in a solvent like dioxane, dimethoxyethane, N-methylpyrrolidone or toluene.

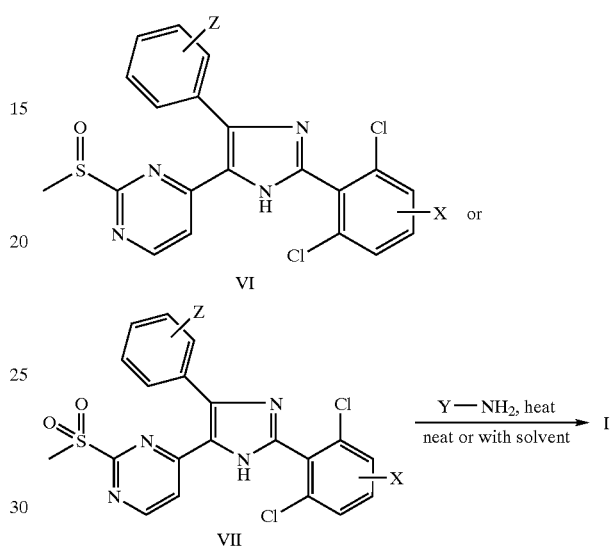

Compounds of formula (VI) and (VII) can be obtained by oxidation of the sulfide group of the thioethers, described by formula (V). To obtain the sulfoxides of formula (VI) the oxidation is preferably carried out by using 3-chloroperbenzoic acid. For the thesis of the sulfones of formula (VII), oxone™ is preferably used.

The thioethers of formula (V)

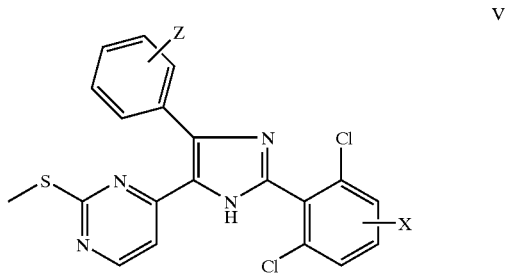

can be obtained by N-deoxygenation of compounds of formula (IV). This reaction is preferably carried out using ethyl bromoacetate in the presence of triethylamine (Chem. Pharm. Bull. 1981, 29, 3145). Alternatively, this reduction can be achieved by the use of triethylphosphite in dimethylformamide.

A compound of formula (IV) can be obtained by reacting a compound of formula (III) with a compound of formula (II), wherein the substituents X and Z have the significance as defined hereinbefore. This reaction is a condensation and is preferably carried out in the presence of ammonia, using methods which are known for other aldehydes.

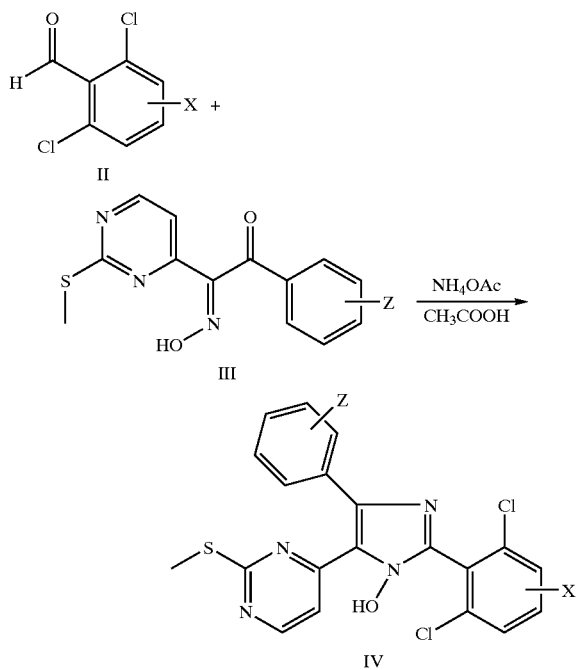

A further embodiment of the invention is the use of a compound of formula (II), wherein the substituent X has the significance as defined hereinabove, for the manufacture of a compound of formula (I) as described in the above-mentioned process.

A further embodiment of the invention is a compound of formula (II),

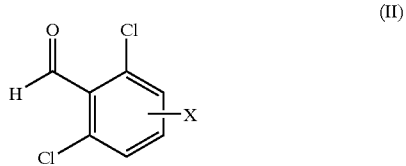

wherein

X is $OR^1$; $SR^2$; $(SO)R^2$; $(SO_2)R^2$ or $CH_2$—Q;
Q represents $OR^1$; $SR^2$; $SOR^2$; $SO_2R^2$; $NR^3R^4$; NH—$CH_2$—$CH_2NR^3R^4$ or halogen;
$R^1$ is selected from the group consisting of hydrogen; $C_1$–$C_3$-alkyl; allyl; dimethylphosphonylmethyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl; trifluoromethylsulfonyl; trimethylsilanyl; triisopropylsilanyl; t-butyldimethylsilanyl; phenyldimethylsilanyl; 1,3-di-t-butyldimethylsilanyloxy-2-propyl; 3-t-butyldimethylsilanyloxy-2-t-butyldimethylsilanyloxymethyl-1-propyl or a group $A^1$—$Q^1$;
$A^1$ represents a methylene, ethylene or propylene group;
$Q^1$ means cyano; carboxyl; $COOCH_3$; $COOCH_2CH_3$;
$R^2$ is $C_1$–$C_6$-alkyl; $CH_2$—COO—$CH_2$—$CH_3$; dimethylphosphonylmethyl; 2,3-epoxy-1-propyl; 2,3-dihydroxy-1-propyl; 2-hydroxy-1-ethyl; 2,2-dimethyl-1,3-dioxolan-4-ylmethyl or $A^1$—$Q^1$;
$R^3$ and $R^4$ are independently selected from the group consisting of hydrogen; methyl; ethyl; 2-morpholinoethyl or together form a 5 to 7 membered, saturated or unsaturated ring, optionally substituted by a methyl group and containing one or two heteroatoms, independently selected from N or O, with the proviso that X=$OR^1$ is not OH or O-allyl.

Preferably, the substituent X is located in the 4-position of the phenyl ring. 2,6-dichlorobenzaldehydes are valuable intermediates for the manufacture of the compounds of formula (I) according to the invention. 2,6-dichloro-3-hydroxybenzaldehyde and 2,6-dichloro-4-hydroxybenzaldehyde are known from the state of the art. The 2,6-dichloro-3-hydroxybenzaldehyde has been synthesized from 3-hydroxybenzaldehyde (Eur. J. Med. Chem. 1993, 28, 103–115), but this requires the use of highly toxic chlorine gas and leads to side products because of overoxidation. The procedure disclosed in this invention (example A2) avoids these disadvantages. 2,6-dichloro-4-hydroxybenzaldehyde can be prepared from 3,5-dichlorophenol by either a Reimer-Tiemann reaction (J. Med. Chem. 1988, 31, 72–83) or by a bromination/Grignard sequence (WO 01/44154). The Reimer-Tiemann procedure does not allow an economically preparation due to very low yields (<4%); in addition, the required use of chloroform causes substantial ecological issues. The other known reaction via a bromination/Grignard sequence requires a total of 4 steps, including stoichiometric bromination with bromine and the use of toxic chloromethyl methyl ether to protect the phenol. In addition, the total yield is only 40%.

This invention provides an improved process for the manufacture of 2,6-dichloro-3-hydroxybenzaldehyde and 2,6-dichloro-4-hydroxybenzaldehyde. This process is characterized by the metallation of protected 2,4-dichlorophenol or 3,5-dichlorophenol with a lithium base, followed by reaction with an ester or amide of formic acid and the deprotection and isolation of the compounds. A suitable lithium base is methyllithium, n-butyllithium, sec-butyllithium, t-butyllithium, lithiumdiisopropylamide or lithium bistrimethylsilylamide, preferred is butyllithium. An appropriate solvent is diethyl ether, tetrahydrofurane or 1,2-dimethoxyethane, preferred is tetrahydrofurane. The metallation step is performed at from about −100° C. to about −60° C., preferably at from about −80° C. to about −70° C. Suitable protecting groups are triisopropylsilanyl, t-butyldimethylsilanyl or phenyldimethylsilanyl, prefered is triiso-propylsilanyl. Suitable derivatives of formic acid are methyl formate, ethylformate, dimethylformamide or N-formylpiperidine, preferred is dimethylformamide. This procedure can also be applied for the manufacture of 2,6-dichloro-3-hydroxymethylbenzaldehyde and 2,6-dichloro-4-hydroxymethylbenzaldehyde according to this invention.

The term "pharmaceutically acceptable salt" as used hereinabove refers to conventional acid-addition salts or base-addition salts that retain the biological effectiveness and properties of the compounds of formula (I) and are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds (see, e.g., H. Ansel et. al., Pharmaceutical Dosage Forms and Drug Delivery Systems, 6th ed., (1995), pp. 196 and 1456–1457.

The compounds of formula (I) and the pharmaceutically acceptable salts of the compounds of formula (I) can be used as pharmaceutical compositions, e.g., in the form of pharmaceutical preparations. The pharmaceutical preparations can be administered orally, e.g., in the form of tablets, coated tablets, dragées, hard and soft gelatine capsules, solutions, emulsions or suspensions. The administration can, however, also be effected rectally, e.g., in the form of suppositories, parenterally, e.g., in the form of injection solutions.

The compounds of formula (I) can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance, no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula (I) or a pharmaceutically acceptable salt thereof and a therapeutically inert carrier are also an object of the present invention, as is a process for their production, which comprises bringing one or more compounds of formula (I) and/or pharmaceutically acceptable salts and, if desired, one or more other therapeutically valuable substances into a galenical administration form together with one or more therapeutically inert carriers.

Because of their activity as tyrosine kinase inhibitors, preferably of c-met kinase, compounds of formula (I) are valuable ingredients of therapeutics aiming at the treatment of cancer and other diseases that correspond with enhanced expression of the c-met receptor or related kinase receptors. Typically compounds of formula (I) block the phosphorylation activity of c-met kinase with an $IC_{50}$ of 0.5 nM to 5 µM.

Therefore, the dosage of a compound according to this invention can vary within wide limits and will also have to be adjusted to the individual requirements in each particular case. In the case of oral administration, the dosage for adults can vary from about 0.01 mg to about 1000 mg per day of a compound of formula (I) or of the corresponding amount of a pharmaceutically acceptable salt thereof. The daily dosage may be administered as single dose or in divided doses and, in addition, the upper limit can also be exceeded when this is found to be indicated.

The following examples and preparations illustrate the invention but are not intended to limit its scope.

EXAMPLES

A Synthesis of Substituted 2,6-dichlorobenzaldehydes

Example A1

2,6-dichloro-4-hydroxybenzaldehyde (A1)

Preparation of 3,5-dichlorotriisopropylsilyloxybenzene (A1.1)

A solution of 4.08 g (25 mmol) 3,5-dichlorophenol and 6.70 g (62.5 mmol) 2,6-lutidine in 75 ml dry $CH_2Cl_2$ 9.96 g (32.5 mmol) triisopropylsilyltriflate was mixed at 0° C. and stirred for 2 hours at this temperature. After hydrolysis with water (15 ml) the organic layer was washed with saturated NaCl, dried over $MgSO_4$ and evaporated to dryness. Chromatography of the crude product on SiGel using iso-hexane as eluent returned A1.1 as a colorless oil in quantitative yield.

$^1$H-NMR (250 MHz, $CDCl_3$) δ=1.03–1.15 (m, 18 H, $CH_3$); 1.16–1.35 (m, 3 H CH); 6.73–6.80 (m, 2 H, $CH_{arom.}$); 6.92–6.98 (m, 1 H, $CH_{arom.}$) $^{13}$C-NMR (62.9 MHz, $CDCl_3$) δ=12.7 (CH); 18.0 (CH3); 119.0, 121.6 ($CH_{arom.}$); 135.2, 157.4 ($C_{arom.}$)

Scale-up

A solution of 200 g 3,5-dichlorophenol and 330 ml 2,6-lutidine in 3.0 l dry $CH_2Cl_2$ 400 g triisopropylsilyltriflate was mixed at 0° C. within 1 h and the mixture was stirred for additional 3 hours at this temperature. After hydrolysis with 1.0 l water, the organic layer was washed with saturated NaCl, dried over $MgSO_4$ and evaporated to dryness (70° C./80 mbar). The residue was taken up in petrol ether and filtrated through SiGel to yield 360 g (92%) A1.1 as colorless oil.

Preparation of 2,6-dichloro-4-hydroxybenzaldehyde (A1) and 2,6-dichloro-4-triisopropylsilyloxybenzaldehyde (A1.2)

A solution of n-BuLi (2.5 M in hexane, 9.4 ml, 23 mmol) was added to a stirred solution of 7.49 g (23 mmol) A1.1 in dry THF (30 ml) under nitrogen keeping the temperature below −67° C. After stirring for 45 minutes at −78° C., 2.14 g (29 mmol) dry dimethylformamide was added keeping the temperature below −65° C. The mixture was allowed to warm up to −10° C. After hydrolysis with NaCl-saturated 2 N HCl (25 ml), the phases were separated and the organic layer was dried over $MgSO_4$ evaporated to dryness. To the residue hexane (20 ml) was added and the precipitated A1 (4.37 g, 23 mmol) was filtered off and washed with hexane (5 ml), m.p. 229–230° C.

$^1$H-NMR (250 MHz, DMSO-$D_6$) δ=6.94 (s, 2 H, $CH_{arom.}$); 10.25 (s, 1 H, CH=O), 11.46 (s (br), 1 H, OH) $^{13}$C-NMR (62.9 MHz, DMSO-$D_6$) δ=117.0 ($CH_{arom.}$); 120.7, 137.8, 162.1 ($C_{arom.}$); 187.2 (CH=O)

A small amount of 2,6-dichloro-4-triisopropylsilyloxybenzaldehyde (A1.2) was isolated from the iso-hexane mother liquor by column chromatography on SiGel (iso-hexane/ethyl acetate 20:1).

$^1$H-NMR (250 MHz, $CDCl_3$) δ=1.05–1.17 (m, 18 H, $CH_3$); 1.19–1.39 (m, 3H, CH); 6.88 (s, 2 H, $CH_{arom.}$); 10.41 (s, 1 H, CH=O) $^{13}$C-NMR (62.9 MHz, $CDCl_3$) δ=12.7 (CH); 17.9 ($CH_3$); 121.5 ($CH_{arom.}$); 123.4, 138.9, 160.4 ($C_{arom.}$); 187.9 (CH=O)

Deprotection of the phenolic hydroxy group can be achieved by a standard procedure using n-$Bu_4$NF in THF and purification by column chromatography on SiGel (iso-hexane/ethyl acetate 1:1) (see example A3).

Scale-up 440 ml n-BuLi (2.7 M in hexane) was added to solution of 360 g A1.1 in 2.6 l dry tetrahydrofurane under nitrogen keeping the temperature below −65° C. After stirring for 2 h at −70° C. 120 ml dry dimethylformamide was added keeping the temperature below −65° C. The mixture was allowed to warm up to room temperature overnight. After addition of 700 ml 4 M HCl the mixture was stirred vigorously for 1 h at room temperature. Then the phases were separated (addition of solid NaCl may be necessary) and the organic layer was dried over sodium sulfate and was reduced in vacuo. Recrystallization of the precipitate from toluene/tetrahydrofurane yielded 154 g (70%) A1.

Example A2

2,6-dichloro-3-hydroxybenzaldehyde (A2)

Preparation of 2,4-dichlorotriisopropylsilyloxybenzene (A2.1)

An analogous reaction to that described in example A1.1, but starting with 2,4-dichlororphenol gave the title compound as a colorless oil in quantitative yield.

$^1$H-NMR (250 MHz, CDCl$_3$) δ=1.07–1.18 (m, 18 H, CH$_3$); 1.20–1.40 (m, 3H CH); 6.82 (d, 8.8 Hz, 1 H, CH$_{arom.}$); 7.07 (dd, 8.8 Hz, 2.5 Hz, 1 H, CH$_{arom.}$); 7.34 (d, 2.5 Hz, 1 H, CH$_{arom.}$) $^{13}$C-NMR (62.9 MHz, CDCl$_3$) δ=13.0 (CH); 18.0 (CH3); 120.8 (CH$_{arom.}$); 125.9 (C$_{arom.}$); 126.2 (C$_{arom.}$); 127.6, 130.1 (CH$_{arom.}$); 151.0 (C$_{arom.}$)

Preparation of 2,6-dichloro-3-hydroxybenzaldehyde (A2)

An analogous reaction to that described in example A1, but starting with A2.1 yielded the title compound as a white solid.

$^1$H-NMR (250 MHz, DMSO-D$_6$) δ=7.19 (d, 8.8 Hz, 1 H, CH$_{arom.}$); 7.39 (d, 8.8 Hz, 1 H, CH$_{arom.}$); 10.33 (s, 1 H, CH=O), 10.92 (s (br), 1 H, OH) $^{13}$C-NMR (62.9 MHz, DMSO-D$_6$) δ=121.1 (CH$_{arom.}$); 121.9, 123.8 (C$_{arom.}$); 130.2 (CH$_{arom.}$); 131.6 (CH$_{arom.}$); 153.5 (C$_{arom.}$); 190.5 (CH=O)

Example A3

2,6-dichloro-4-hydroxymethylbenzaldehyde (A3)

Preparation of 3,5-dichloro(triisopropylsilyloxymethyl)benzene (A3.1)

An analogous reaction to that described in example A1.1, but starting with 3,5-dichlorobenzylic alcohol gave the title compound as a colorless oil in quantitative yield.

$^1$H-NMR (250 MHz, CDCl$_3$) δ=0.96–1.25 (m, 21 H, i-Pr); 4.78 (s, 2 H, OCH$_2$); 7.23 (s, 2H, CH$_{arom.}$) $^{13}$C-NMR (62.9 MHz, CDCl$_3$) δ=12.1 (CH); 18.1 (CH$_3$); 64.0 (OCH$_2$); 124.2, 127.0 (C$_{arom.}$H); 134.9, 145.3 (C$_{arom.}$)

Preparation of 2,6-dichloro-4-(triisopropylsilyloxymethyl)benzaldehyde (A3.2)

An analogous reaction to that described in example A1, but starting with A3.1 and hydrolyzing with ice water instead of aqueous HCl yielded the title compound as a colorless oil that solidifies on ice standing (eluent: iso-hexane/ethyl acetate 20:1).

$^1$H-NMR (250 MHz, CDCl$_3$) δ=1.03–1.28 (m, 21 H, i-Pr); 4.82 (s, 2 H, OCH$_2$); 7.37 (s, 2H, CH$_{arom.}$); 10.48 (s, 1 H, CH=O) $^{13}$C-NMR (62.9 MHz, CDCl$_3$) δ=12.0 (CH); 18.1 (CH$_3$); 63.6 (OCH$_2$); 126.8 (C$_{arom.}$H); 128.6, 137.2, 149.0 (C$_{arom.}$); 188.8 (CH=O)

Scale-up

To a solution of 70 g A3.1 in 220 ml dry tetrahydrofurane 131 ml n-BuLi (1.6 M in hexane) was added under nitrogen keeping the temperature below −70° C. After stirring for 45 minutes at −75° C. 28 ml dry dimethylformamide was added keeping the temperature below −65° C. The mixture was stirred additional 30 minutes at −75° C. and then was allowed to warm up 0° C. within 3 h. After 2 h at 0° C. 150 ml ice water and 150 ml ether were added. The phases were separated and the aqueous layer extracted with 100 ml ether. The combined organic layers were washed with aqueous NaCl dried over sodium sulphate and evaporated to dryness. Yield: 73 g (95%) A3.2 as a light brown oil, that solidifies an ice standing.

Preparation of 2,6-dichloro-4-hydroxymethylbenzaldehyde (A3)

426 mg (1.2 mmol) A3.2 (426 mg, 1.2 mmol) were dissolved in dry tetrahydrofurane (20 ml) and a solution of n-Bu$_4$NF (1.3 ml, 1 M in THF, 1.3 mmol) was added at room temperature and stirred overnight. After concentration in vacuo, 134.0 mg A3 was isolated by column chromatography on SiGel (iso-hexane/ethyl acetate 2:1), as a colorless solid, m.p. 109–110° C.

$^1$H-NMR (250 MHz, CDCl$_3$) δ=1.99 (t, 4.4 Hz, 1 H, OH); 4.74 (d, 4.4 Hz, 2H, OCH$_2$); 7.40 (s, 2 H, CH$_{arom.}$); 10.48 (s, 1 H, CH=O) $^{13}$C-NMR (62.9 MHz, CDCl$_3$) δ=63.4 (OCH$_2$); 127.5 (C$_{arom.}$H); 129.2, 137.4, 147.9 (C$_{arom.}$); 188.7 (CH=O)

Scale-up

To a solution of 65 g (0.18 mol) A3.2 in 1100 ml ethanol at 50° C., 180 ml 0.25 N HCl was added and the mixture was stirred for 6 h at 85° C. The ethanol was removed in vacuo whereupon the product precipitated. 700 ml ethyl acetate/petrol ether (2:1) was added and the organic layer was washed with water and aqueous NaCl and dried over sodium sulphate. The solution was reduced to about 100 g and 200 ml warm petrol ether were added and shortly warmed up to 50° C. After standing at room temperature overnight, the precipitated A3 was filtered off and washed with petrol ether/ethyl acetate (15:1). Yield: 24.3 g (66%). Purification of the mother liquor by column chromatography yielded another 4 g A3.

Example A4

Preparation of methyl (3,5-dichloro-4-formylphenoxy)acetate (A4)

A mixture of 382 mg (2.0 mmol) A1, 337 mg (2.2 mmol) methyl bromoacetate and 387 mg (2.8 mmol) potassium carbonate in 6 ml dry acetone were stirred for 2 h at 60° C. After filtration and removal of the solvent the residue was purified by column chromatography on SiGel (hexane/ethyl acetate 4:1). Yield: 508 mg (97%) A4, colorless solid.

$^1$H-NMR (250 MHz, DMSO-D$_6$) δ=3.72 (s, 3 H, CH$_3$); 5.04 (s, 2 H, CH$_2$); 7.28 (s, 2 H, CH$_{arom.}$); 10.29 (s, 1 H, CH=O). $^{13}$C-NMR (62.9 MHz, DMSO-D$_6$) δ=52.1 (CH$_3$), 65.2 (CH$_2$); 116.5 (CH$_{arom.}$); 123.1, 137.5, 161.1 (C$_{arom.}$); 168.3 (C=O); 187.8 (CH=O).

Example A5

Preparation of ethyl (3,5-dichloro-4-formylphenoxy)acetate (A5)

An analogous reaction to that described in example A4, but reacting with ethyl bromoacetate yielded 94% A5.

¹H-NMR (250 MHz, CDCl₃): δ=1.32 (t, 7.2 Hz, 3 H, CH₃); 4.30 (q, 7.2 Hz, 2 H, CH₂); 4.68 (s, 2 H, CH₂); 6.92 (s, 2 H, CH$_{arom.}$); 10.41 (s, 1 H, CH=O). ¹³C-NMR (62.9 MHz, CDCl₃): δ=14.3 (CH₃); 62.1, 65.5 (CH₂); 116.4 (CH$_{arom.}$); 123.8, 139.2, 160.9 (C$_{arom.}$); 167.3 (C=O); 187.8 (CH=O).

Example A6

Preparation of (3,5-dichloro-4-formylphenoxy) acetonitrile (A6)

An analogous reaction to that described in example A4, but reacting with bromoacetonitrile yielded 87% A6.

¹H-NMR (250 MHz, CDCl₃) δ=4.87 (s, 2 H, CH₂); 7.02 (s, 2 H, CH$_{arom.}$); 10.42 (s, 1 H, CH=O) ¹³C-NMR (62.9 MHz, CDCl₃) δ=53.7 (CH₂); 113.7 (CN); 116.4 (CH$_{arom.}$); 125.1, 139.3, 159.1 (C$_{arom.}$); 187.5 (CH=O)

Example A7

Preparation of dimethyl (3,5-dichloro-4-formylphenoxymethyl)phosphine oxide (A7)

To a solution of 191 mg (1.00 mmol) A1 in 4 ml dry dimethylformamide 139 mg (1.1 mmol) chloromethyldimethylphosphine oxide and 194 mg (1.4 mmol) potassium carbonate were added. The mixture was heated in a microwave reactor to 200° C. for 10 minutes. After removal of the solvent and column chromatography on SiGel (dichloromethane/methanol 95:5), 149 mg (53%) A7 were obtained as a colorless solid, m.p. 136–139° C.

¹H-NMR (250 MHz, CDCl₃): δ=1.52 (d, 13.5 Hz, 6 H, PCH₃); 4.53 (d, 6.6 Hz, 2H, PCH₂); 7.36 (s, 2 H, CH$_{arom.}$); 10.29 (s, 1 H, CH=O). ¹³C-NMR (62.9 MHz, CDCl₃): δ=14.0 (d, 69.0 Hz, PCH₃); 67.3 (d, 78.7 Hz, PCH₂); 116.5 (CH$_{arom.}$); 122.9, 137.4 (C$_{arom.}$); 162.1 (d, 10.3 Hz, C$_{arom.}$); 187.6 (CH=O). ¹³P-NMR (101.3 MHz, DMSO-D₆): δ=39.2 (C₃P=O).

Example A8

Preparation of (rac)-2,6-dichloro-4-(2,2-dimethyl-[1,3]-dioxolane-4-ylmethoxy)benzaldehyde (A8)

To a solution of 6.64 g (35.0 mmol) A1, 10.03 g (38.0 mmol) triphenylphosphine and 5.06 g (38.0 mmol) (rac)-2,2-dimethyl-[1,3]-dioxolane-4-methanol in 100 ml dry tetrahydrofurane a solution of 6.48 g (37.0 mmol) diethyl azodicarboxylate in 20 ml dry tetrahydrofurane was added and the mixture was stirred at room temperature overnight. After removal of the solvent and column chromatography on SiGel (hexane/ethyl acetate 4:1) 6.12 g (57%) A8 were obtained as a colorless oil that solidified on ice standing.

¹H-NMR (250 MHz, CDCl₃) δ=1.41 (s, 3 H, CH₃); 1.46 (s, 3 H, CH₃); 3.75–4.61 (m, 5 H, CHOR und CH₂OR); 6.95 (s, 2 H, CH$_{arom.}$); 10.41 (s, 1 H, CH=O). ¹³C-NMR (62.9 MHz, CDCl₃) δ=25.3, 26.8 (CH3); 66.4, 69.6, 73.6 (CH, CH₂); 110.3 (C); 116.3 (CH$_{arom.}$); 123.4, 139.2, 161.8 (C$_{arom.}$); 187.8 (CH=O).

Preparation of (R)-2,6-dichloro-4-(2,2-dimethyl-[1,3]-dioxolane-4-ylmethoxy)benzaldehyde (A8.1)

An analogous reaction to that described in example A8, but starting with (R)-2,2-dimethyl-[1,3]-dioxolane-4-methanol gave A8.1 in 63% yield.

Preparation of (S)-2,6-dichloro-4-(2,2-dimethyl-[1,3]-dioxolane-4-ylmethoxy)benzaldehyde (A8.2)

An analogous reaction to that described in example A8, but starting with (S)-2,2-dimethyl-[1,3]-dioxolane-4-methanol gave A8.2 in 55% yield.

Example A9

Preparation of 2,6-dichloro-4-methylthiobenzaldehyde (A9)

Preparation of 2,6-dichloro-4-thiomethylbenzonitrile (A9.1)

7.1 g (101 mmol) sodium thiomethylate was added to a solution of 20.0 g (93 mmol) 2,6-dichloro-4-nitrobenzonitrile (Pestic. Chem., Proc. Int. Congr. Pestic. Chem. 2$^{nd}$, Tahoori, A. (Ed.) 1972, 5, 125–139) in 250 ml dry 2-butanone at −78° C. The stirred suspension was allowed to warm up to room temperature overnight. All volatile components were removed in vacuo, water (200 ml) was added and the mixture was extracted three times with CH₂Cl₂ (100 ml each). The combined organic layers were dried over Na₂SO₄ and concentrated under reduced pressure to ⅓. 12.0 g (59%) A9.1 precipitated on overnight standing at −78° C. and was used without further purification. An analytical sample was purified by column chromatography on SiGel (iso-hexane/ethyl acetate 9:1).

¹H-NMR (250 MHz, CDCl₃) δ=2.52 (s, 3 H, SCH₃); 7.18 (s, 2 H, CH$_{arom.}$) ¹³C-NMR (62.9 MHz, CDCl₃) δ=14.9 (SCH₃); 109.5 (C$_{arom.}$); 113.8 (CN); 124.0 (CH$_{arom.}$); 138.4, 149.0 (C$_{arom.}$)

Preparation of 2,6-dichloro-4-thiomethylbenzaldehyde (A9)

A solution of 11.82 g (54 mmol) A9.1 in 65 ml dry CH₂Cl₂ was cooled to −3° C. and a solution of 9.24 g (65 mmol) diisobutylaluminium hydride in 65 ml dry CH₂Cl₂ was added slowly keeping the temperature below 1° C. After 30 minutes under stirring at 0° C. the reaction was allowed to warm up to room temperature and stirred for additional 75 minutes. The reaction mixture was poured on a mixture of ice (250 g) and HCl (300 ml, 1:1) and vigorously stirred for 1 hour. The phases were separated and the aqueous layer was extracted twice with CH₂Cl₂ (200 ml each). The combined organic layers were washed twice with 5% NaHCO₃ (250 ml each) once with saturated NaCl (250 ml) dried over Na₂SO₄ and evaporated to dryness. Column chromatography on SiGel (iso-hexane/ethyl acetate 9:1) returned 10.7 g (48 mmol) A9 as a pale yellow solid, m.p. 87.5–89.5° C.

¹H-NMR (250 MHz, CDCl₃) δ=2.53 (s, 3 H, SCH₃); 7.16 (s, 2 H, CH$_{arom.}$); 10.43 (s, 1 H, CH=O) ¹³C-NMR (62.9 MHz, CDCl₃) δ=14.8 (SCH₃); 125.6 (CH$_{arom.}$); 125.7, 137.8, 148.4 (C$_{arom.}$); 188.0 (CH=O)

Example A10

2,6-dichloro-4-methanesulfinylbenzaldehyde (A10)

To a solution of 100 mg (0.452 mmol) A9 in 6 ml dichloromethane and 4 ml ethyl acetate at −40° C. a solution of 142 mg (0.452 mmol) 3-chloroperoxybenzoic acid (55%) in 4 ml ethyl acetate was added within 5 minutes. After stirring for 2 h at −40° C., the mixture was allowed to warm up to room temperature, then water and ethyl acetate were added. The organic layer was washed twice with 0.1 M NaOH dried over sodium sulphate and the solvent was removed in vacuo. Purification of the residue by column chromatography on SiGel (heptane/ethyl acetate 1:1) yielded 35 mg (33%) A10, m.p. 100–102° C.

¹H-NMR (250 MHz, CDCl₃) δ=2.82(s, 3H, CH₃), 7.65(s, 2H, 3-H/5-H), 10.50(s, 1H, CHO). ¹³C-NMR (62.9 MHz, CDCl₃) δ=43.7 (CH₃), 124.5 (C-3/C-5), 132.1 (C-1), 137.7 (C-2/C-6),152.5 (C-4), 187.9 (CHO).

Example A11

2,6-dichloro-4-methanesulfonylbenzaldehyde (A11)

The chromatographic workup of example A10 yielded additionally 20 mg (17%) (A11, m.p. 125–128° C.

$^1$H-NMR (250 MHz, CDCl$_3$) δ=3.14 (s, 3H, CH$_3$), 7.94 (s, 2H, 3-H/5-H), 10.50(s, 1H, CHO). $^{13}$C-NMR (62.9 MHz, CDCl$_3$) δ=44.6 (CH$_3$), 128.6 (C-3/C-5), 135.1 (C-1), 137.9 (C-2/C-6), 145.2 (C-4), 187.9 (CHO).

Example A12

2,6-dichloro-4-(2-hydroxyethoxy)benzaldehyde (A12)

To a solution of 3.00 g (15.7 mmol) A1 and 1.4 ml (19.7 mmol) 2-bromoethanol in 50 ml dry dimethyl formamide 3.06 g (22.1 mmol) potassium carbonate were added the mixture was heated to 80° C. for 2 hours. Every 30 minutes, 0.2 ml 2-bromoethanol were added until no A1 was longer observed by TLC (hexanes/ethyl acetate 1:1). The solvent was removed in vacuo and the residue was partitionated between ethyl acetate and water. The organic layer was dried over sodium sulfate and evaporated to dryness. The residue was treated with ether and filtered off to yield 3.03 g (82%) A12, m.p. 83–85° C.

$^1$H-NMR (250 MHz, CDCl$_3$) δ=4.02(t, 2H, 2'-H), 4.13(t, 2H, 1'-H), 6.96(s, 2H, 3-H, 5-H), 10.50(s, 1H, CHO). $^{13}$C-NMR (62.9 MHz, CDCl$_3$) δ=60.9 (C-2'), 70.3 (C-1'), 116.2 (C-3, C-5), 123.1 (C-1), 139.1 (C-2, C-6), 161.9 (C-4), 187.7 (CHO).

Example A13

2,6-dichloro-4-(2,3-dihydroxy-1-propoxy)benzaldehyde (A13)

An analogous reaction to that described in example A12, but reacting with 3-bromo-propane-1,2-diol and sodium hydride and purification by preparative scale HPLC on RP 18 (methanol-water-gradient) yielded 25% A13, m.p. 52–55° C.

$^1$H-NMR (250 MHz, CDCl$_3$) δ=1.5–2.8 (br, 2H, OH), 3.75 (mc, 1H, 3'-H), 3.88 (mc, 1H, 3'-H), 4.11 (mc, 1H, 2'-H), 4.11 (s, 2H, 1'-H), 7.92 (s, 2H, 3-H/5-H), 10.40 (s, 1H, CHO). $^{13}$C-NMR (62.9 MHz, CDCl$_3$) δ=63.6 (C-3'), 70.26 (C-1'), 70.34 (C-2'), 116.6 (C-3/C-5), 123.7 (C-1), 139.5 (C-2/C-6), 162.0 (C-4), 188.1 (CHO).

Example A14

3,5-dichloro-4-formylphenyl trifluoromethanesulfonate (A14)

A solution of 500 mg (2.62 mmol) A1 in 4.0 ml dry pyridine was cooled to 0° C. and 812 mg (2.88 mmol) trifluoromethanesulfonate anhydride was added and stirred at room temperature overnight. The mixture was poured on a mixture of ice and 8 ml 6 M HCl, and extracted with ethyl acetate. The organic layer was dried over sodium sulfate, evaporated to dryness and the residue was purified by column chromatography on SiGel (heptane/ethyl acetate 5:1) yielding 680 mg (80%) A14 as a colorless oil.

$^1$H-NMR (250 MHz, CDCl$_3$) δ=7.40 (s, 2H, 2-H/6-H), 10.47 (s, 1H, CHO). $^{13}$C-NMR (62.9 MHz, CDCl$_3$) δ=121.1 (q, CF$_3$), 123.3 (C-2/C-6), 130.9 (C-4), 138.7 (C-3/C-5), 151.0 (C-1), 187.4 (CHO).

Example A15

Preparation of ethyl 3,5-dichloro-4-formylbenzyloxyacetate (A15)

A solution of 500 mg (2.4 mmol) A3 in 5 ml dry dimethyl formamide was cooled in an ice bath and 73 mg (3.0 mmol) sodium hydride was added and the mixture was stirred for 10 minutes. After addition of 410 mg (2.6 mmol) ethyl bromoacetate, the mixture was heated to 110° C. for 8 h. The solvent was removed in vacuo and the residue was taken up in ethyl acetate and washed with water. The organic layer was dried over sodium sulphate and evaporated to dryness. Purification of the residue by column chromatography on SiGel (heptane/ethyl acetate 4:1) yielded 40 mg (6%) A15.

$^1$H-NMR (500 z, CDCl$_3$) δ=1.24 (t, 6 Hz, 3 H, CH$_3$); 4.11 (s, 2 H, CH$_2$); 4.19 (q, 6 Hz, 2 H, CH$_2$); 4.60 (s, 2 H, CH$_2$); 6.96 (s, 2 H, CH$_{arom.}$); 10.42 (CH=O) $^{13}$C-NMR (125.8 MHz, CDCl$_3$) δ=12.7 (CH$_3$); 60.5 (CH$_2$), 66.9 (CH$_2$); 70.2 (CH$_2$); 126.5 (C-2/C-6); 128.3 (C-4); 136.1 (C-3/C-5); 143.4 (C-1); 168.7 (COOR), 187.4 (CH=O)

Example A16

Preparation of 2,6-dichloro-4-bromomethylbenzaldehyde (A16)

21.0 mg (0.8 mmol) Phosporous tribromide was added to a stirred solution of 480 mg (2.3 mmol) A3 in 20 ml dry tetrahydrofurane, and the solution was stirred for 3 hours at room temperature. After hydrolysis (15 ml) the phases were separated and the organic layer was washed with saturated NaCl (10 ml) and dried over magnesium sulfate. 236 mg (0.9 mmol) A16 was obtained by column chromatography on SiGel (iso-hexane/ethyl acetate 9:1).

$^1$H-NMR (250 MHz, CDCl$_3$) δ=4.38 (s, 2 H, CH$_2$Br); 7.42 (s, 2 H, CH$_{arom.}$); 10.46 (s, 1 H, CH=O) $^{13}$C-NMR (62.9 MHz, CDCl$_3$) δ=29.9 (CH$_2$Br); 130.0 (C$_{arom.}$);130.2 (C$_{arom.}$H); 137.3, 144.1 (C$_{arom.}$); 188.3 (CH=O)

Example A17

Preparation of 2,6-dichloro-4-chloromethylbenzaldehyde (A17)

289 mg (2.5 mmol) Methansulfonylchloride was added to a stirred solution of 470 mg (2.3 mmol) A3 and 255 mg (2.5 mmol) triethylamine in dry 20 ml dichloromethane, and the solution was stirred at room temperature overnight. After hydrolysis (15 ml), the phases were separated and the organic layer was washed with saturated NaCl (10 ml) and dried over magnesium sulfate. 236 mg (0.9 mmol) A17 was obtained by column chromatography on SiGel (iso-hexane/ethyl acetate 9:1).

$^1$H-NMR (250 MHz, CDCl$_3$) δ=4.52 (s, 2 H, CH$_2$Cl); 7.42 (s, 2 H, CH$_{arom.}$); 10.46 (s, 1 H, CH=O) $^{13}$C-NMR (62.9 MHz, CDCl$_3$) δ=43.8 (CH$_2$Cl); 129.6 (C$_{arom.}$H); 130.0, 137.3, 143.7 (C$_{arom.}$); 188.3 (CH=O)

Example A18

Preparation 2,6-dichloro-4-p-toluenesulfonyloxybenzaldehyd (A18)

A solution of 488 mg (2.56 mmol) p-toluenesulfonyl chloride in 5 ml solvent was added to a solution of 500 mg (2.44 mmol) A3 and 617 mg triethylamine in 20 ml dry dichloromethane at 0–5° C. and was allowed to warm up to room temperature within 1 h. The organic layer was washed with water for several times, dried over sodium sulfate and evaporated to dryness. Chromatography of the residue on SiGel (heptane/ethyl acetate 3:1) yielded 180 mg (21%) A18, m.p. 77–80° C.

$^1$H-NMR (250 MHz, CDCl$_3$): δ=2.48 (s, 3H, CH$_3$), 5.03 (s, 2H, OCH$_2$), 7.24 (s, 2H, 3-H/5-H), 7.38 (d, 2H, 2'-H/6'-

H), 7.79 (d, 2H, 3'-H/5'-H), 10.42 (s, 1H, CHO). $^{13}$C-NMR (62.9 MHz, CDCl$_3$): δ=22.1 (CH$_3$), 69.2 (CH$_2$), 128.4 (C-2'/C-6'), 129.0 (C-3/C-5), 130.5 (C-3'/C-5'), 130.7, 133.0, 137.5, 140.4, 146.0 (C$_{arom.}$) 188.5 (CHO).

Example A19

Preparation of N-(3,5-dichloro-4-formyl)benzyl morpholine (A19)

To a solution of 215 mg (0.8 mmol) A16 and 75 mg (0.9 mmol) morpholine in 5 ml acetonitrile 119 mg (0.9 mmol) potassium carbonate was added and the resulting mixture was stirred at 80° C. for 4 hours. After filtration and removal of the solvent in vacuo 94 mg (0.3 mmol) A19 was obtained by column chromatography on SiGel (iso-hexane/ethyl acetate 4:1).

$^1$H-NMR (250 MHz, CDCl$_3$) δ=2.45 (d, 4.6 Hz, 4 H, OCH$_2$); 3.48 (s, 2 H, NCH$_2$); 3.72 (d, 4.6 Hz, 4 H, NCH$_2$); 7.39 (s, 2 H, CH$_{arom.}$); 10.46 (s, 1H, CH=O) $^{13}$C-NMR (62.9 MHz, CDCl$_3$) δ=53.7 (OCH$_2$); 62.0, 67.0 (NCH$_2$); 129.0 (C$_{arom.}$); 129.9 (C$_{arom.}$H); 137.1, 145.8 (C$_{arom.}$); 188.7 (CH=O)

Example A20

Preparation ethyl 3,5-dichloro-4-formylbenzylthioacetate (A20)

A solution of 200 mg (0.75 mmol) A16, 98 mg (0.97 mmol) triethylamine and 99 g (0.82 mmol) ethyl thioacetate in 4.0 ml dry tetrahydrofurane was stirred at room temperature for 8 h. After removal of the solvent in vacuo, the residue was partitioned between ethyl acetate and water. The organic layer was dried over sodium sulfate and evaporated to dryness. Chromatography of the residue on SiGel (heptane/ethyl acetate 10:1) yielded 180 mg (79%) A20.

$^1$H-NMR (500 z, CDCl$_3$) δ=1.31 (t, 6 Hz, 3 H, CH$_3$); 3.08 (s, 2 H, SCH$_2$); 3.62 (s, 2 H, Ar—CH$_2$); 4.25 (q, 6 Hz, 2 H, CH$_2$); 7.41 (s, 2 H, CH$_{arom.}$); 10.48 (CH=O) $^{13}$C-NMR (125.8 MHz, CDCl$_3$) δ=14.2 (CH$_3$); 32.3 (CH$_2$), 35.1 (CH$_2$); 61.6 (CH$_2$); 129.4 (C-4); 130.0 (C-2/C-6); 137.1 (C-3/C-5); 144.6 (C-1); 169.8 (COOR), 188.3 (CH=O)

Example A21

Preparation of 2,6-dichlor-4-(2-hydroxyethyl-thiomethyl)benzaldehyde (A21)

67 mg (0.48 mmol) Potassium carbonate was added to a solution of 100 mg (0.373 mmol) A16 und 32 mg (0.41 mmol) 2-thioethanol in 4 ml dry acetonitrile, and stirred for 4 h at 80° C. After removal of the solvent in vacuo, the residue was partitioned between ethyl acetate and water. The organic layer was dried over sodium sulfate and evaporated to dryness. Chromatography of the residue on SiGel (heptane/ethyl acetate 5:1) yielded 30 mg (30%) A21.

$^1$H-NMR (250 MHz, CDCl$_3$) δ=2.05 (br, 1H, OH), 2.68 (t, 2H, SCH$_2$), 3.72 (s, 2H, Ar—CH$_2$), 3.79 (t, CH$_2$OH), 7.38 (s, 2H, 3-H/5-H), 10.47 (s, 1H, CHO). $^{13}$C-NMR (62.9 MHz, CDCl$_3$) δ=34.5 (SCH$_2$), 35.0 (Ar—CH$_2$—S), 60.9 (CH$_2$OH), 128.9 (C-1), 130.0 (C-3/C-5), 137.2 (C-2/C-6), 145.6 (C-4), 188.4 (CHO).

Example A22

Preparation of 4-(2-morpholinoethyl)-3,5-dichloro-4-formylbenzylamine (A22)

An analogous reaction to that described in example A21, but reacting with 4-(2-aminoethyl)morpholine and eluting with ethyl acetate yielded 19% A11.

$^1$H-NMR (500 z, CDCl$_3$) δ=2.41; 2.52; 2.68; 3.66; 3.74; 7.44 (CH$_{arom.}$); 10.48 (CH=O); (poor resolution in aromatic range) $^{13}$C-NMR (125.8 MHz, CDCl$_3$) δ=50.8 (CH$_2$—CH$_2$); 54.0 (CH$_2$—N); 56.7 (CH$_2$—CH$_2$); 57.9 (Ar—CH$_2$); 66.8 (CH$_2$O); 129.1 (C-4); 129.6 (C-2/C-6); 137.0 (C-3/C-5); 146.5 (C-1); 188.3 (CH=O)

Example A23

Preparation of 2,6-dichloro-4-(2-methoxy-ethoxymethoxy)-benzaldehyde (A23)

82 mg (3.4 mmol) sodium hydride was added to an ice cooled solution of 500 mg (2.6 mmol) A1 and 342 mg (2.7 mmol) methoxyethoxymethylchloride in 5 ml dry dimethylformamide and the mixture was stirred at 60° C. for 8 hours. The solvent was distilled off and the residue was partitionated between aqueous ammonia and ethyl acetate. The organic layer was dried over sodium sulfate and evaporated to dryness yielding 370 mg (51%) A23, which was used without further purification.

$^1$H-NMR (250 MHz, CDCl$_3$) δ=3.38 (s, 3H, CH$_3$), 3.52–3.62 (m, 2H, OCH$_2$), 3.78–3.88 (m, 2H, OCH$_2$), 5.32 (s, 2H, OCH$_2$O), 7.09 (s, 2H, 3-H/5-H), 10.42 (s, 1H, CHO). $^{13}$C-NMR (62.9 MHz, CDCl$_3$) δ=59.5 (CH$_3$), 68.8, 71.8 (OCH$_2$), 93.8 (OCH$_2$O), 118.0 (C-3/C-5), 124.1 (C-1), 139.2 (C-2/C-6), 160.8 (C-4), 188.1 (CHO).

Example A24

Preparation of 2,6-dichloro-4-[2-(tert-butyldimethylsilanyloxy)-1-(tert-butyldimethyl-silanyloxymethyl)-ethoxy]-benzaldehyde (A24)

An analogous reaction to that described in example A8, but reacting with 1,3-bis-(tert-butyldimethyl-silanyloxy) propan-2-ol and eluting with heptane/ethyl acetate (5:1) yielded 86% A24.

$^1$H-NMR (400 MHz, CDCl$_3$) δ=−0.01 (s, 6 H, Si—CH$_3$), 0.02 (s, 6 H, Si—CH$_3$), 0.82 (s, 18H, $^t$Bu), 3.71–3.89 (m, 4H, CH$_2$OSi), 4.71–4.79 (m, 1H, CH), 7.22 (s, 2H, 3-H/5-H), 10.27 (s, 1H, CHO). $^{13}$C-NMR (100.6 MHz, CDCl$_3$) δ=−5.16, −5.14 (SiCH$_3$), 18.2 (C(CH$_2$)$_3$), 26.0 (C(CH$_2$)$_3$), 62.2 (CH$_2$OSi), 80.4 (OCH), 117.6 (C-3/C-5), 122.6 (C-1), 138.0 (C-2/C-6), 162.6 (C-4), 187.9 (CHO).

Example A25

Preparation of 2,6-dichloro-4-(2-hydroxy-1-hydroxymethyl-ethoxy)-benzaldehyde (A25)

200 mg (0.4 mmol) A24 and 1 ml (13 mmol) trifluoroacetic acid were stirred in 1 ml dichloromethane at room temperature for two hours. The mixture was evaporated to dryness and purified by preparative scale HPLC on RP 18 (methanol-water-gradient) to yield A25.

$^1$H-NMR (400 MHz, CDCl$_3$) δ=3.44–3.66 (m, 4H, CH$_2$OH), 4.44–4.56 (m, 1H, CH), 4.90 (t, 2H, OH), 7.23 (s, 2H, 3-H/5-H), 10.28 (s, 1H, CHO). $^{13}$C-NMR (100.6 MHz, CDCl$_3$) δ=60.1 (CH$_2$OH), 81.5 (OCH), 117.1 (C-3/C-5), 122.0 (C-1), 137.4 (C-2/C-6), 162.4 (C-4), 187.5 (CHO).

Example A26

Preparation of 2,6-dichloro-4[-3-((tert-butyldimethylsilanyloxy))-2-(tert-butyldimethylsilanyloxymethyl)-propoxy)-benzaldehyde (A26)

3.43 g (18 mmol) A1, 7.40 g (18 mmol) methanesulfonic acid 3-(tert-butyldimethylsilanyloxy)-2-(tert-butyldimethylsilanyloxymethyl)propyl ester (Kim, H. S., et al., J. Med. Chem. 44 (2001) 3092–3108), 3.72 g (27 mmol) potassium carbonate and 41 mg (0.15 mmol) 18-crown-6 were stirred in 40 ml dimethylformamide at 40° C. overnight. 600 ml ethyl acetate and 250 ml aqueous NaCl were added. The organic layer was washed four times with saturated aqueous NaCl (80 ml each), dried over sodium sulfate and evaporated to dryness. Column chromatography of the residue on SiGel (heptane/ethyl acetate 10:1) yielded 508 mg (27%) A26.

$^1$H-NMR (400 MHz, CDCl$_3$) δ=0.00 (s, 12H, Si—CH$_3$), 0.83 (s, 18H, $^t$Bu), 2.00–2.10 (m, 1H, CH), 3.60–3.73 (m, 4H, CH$_2$OSi), 4.05–4.14 (m, 2H, O—CH$_2$), 7.19 (s, 2H, 3-H/5-H), 10.26 (s, 1H, CHO). $^{13}$C-NMR (100.6 MHz, CDCl$_3$) δ=−5.19, −5.14 (SiCH$_3$), 18.3 (C(CH$_2$)$_3$), 26.1 (C(CH$_2$)$_3$), 43.6 (CH), 60.0 (CH$_2$OSi), 67.0 (O—CH$_2$), 116.6 (C-3/C-5), 122.7 (C-1), 138.0 (C-2/C-6), 162.5 (C-4), 188.0 (CHO).

Example A27

Preparation of 2,6-dichloro-4-(3-hydroxy-2-hydroxymethyl-propoxy)-benzaldehyde (A27)

An analogous reaction to that described in example A25 but starting with A26 yielded A27.

Example A28

2,6-dichloro-3-hydroxymethylbenzaldehyde (A28)

Preparation of 2,4-dichloro (triisopropylsilyloxymethyl)benzene (A28.1)

An analogous reaction to that described in example A3.1, but starting with 2,4-dichlorobenzylic alcohol gave the title compound as a colorless oil in quantitative yield.

$^1$H-NMR (400 MHz, CDCl$_3$) δ=1.1 (d, 7 Hz, 18 H, CH$_3$); 1.15–1.29 (m, 3 H, CH); 4.83 (s, 2 H, OCH$_2$); 7.28 (dd, 8 Hz, 2 Hz, 1 H, C5-H); 7.32 (d, 2 Hz, 1 H, C3-H); 7.59 (d, 8 Hz, 1 H, C6-H) $^{13}$C-NMR (100.6 MHz, CDCl$_3$) δ=12.4 (CH); 18.4 (CH$_3$); 62.5 (OCH$_2$); 127.4, 128.5, 128.9 (C$_{arom.}$H); 132.0, 133.1, 138.1 (C$_{arom.}$)

Preparation of 2,6-dichloro-3-(triisopropylsilyloxymethyl)benzaldehyde (A28.2)

An analogous reaction to that described in example A3.2, but starting with A28.1 yielded the title compound as a colorless oil that solidifies on overnight standing (eluent: iso-hexane/ethyl acetate 20:1).

$^1$H-NMR (400 MHz, CDCl$_3$) δ=1.03–1.15 (m, 18 H, CH$_3$); 1.15–1.29 (m, 3 H, CH); 4.88 (s, 2 H, OCH$_2$); 7.44 (d, 8 Hz, 1 H, C5-H); 7.80 (d, 8 Hz, 1 H, C6-H), 10.50 (s, 1 H, C=O)

$^{13}$C-NMR (100.6 MHz, CDCl$_3$) δ=12.3 (CH); 18.4 (CH$_3$); 62.3 (OCH$_2$); 129.8 (C$_{arom.}$H); 130.4 (C$_{arom.}$); 131.6 (C$_{arom.}$H); 133.4, 135.0, 140.3 (C$_{arom.}$); 189.5 (C=O)

Preparation of 2,6-dichloro-3-hydroxymethylbenzaldehyde (A28)

3.3 g (9.1 mmol) A28.2 was dissolved in dry tetrahydrofurane (80 ml) and a solution of n-Bu$_4$NF (10.0 ml, 1 M in THF, 10.0 mmol) was added at room temperature and stirred for 15 Minutes. After concentration in vacuo 600.0 mg (32%), A28 were isolated by column chromatography on SiGel (iso-hexane/ethyl acetate 2:1), as a colorless solid, m.p. 93–95° C.

$^1$H-NMR (400 MHz, CDCl$_3$) δ=4.82 (s, 2 H, OCH$_2$); 7.41 (d, 8 Hz, 1 H, C5-H); 7.67 (d, 8Hz, 1 H, C6-H), 10.48 (s, 1 H, C=O) $^{13}$C-NMR (100.6 MHz, CDCl$_3$) δ=61.7 (OCH$_2$); 129.5 (C$_{arom.}$H); 130.5 (C$_{arom.}$); 132.1(C$_{arom.}$H); 134.2, 135.2, 139.1 (C$_{arom.}$); 189.2 (C=O)

B Synthesis of the "Weinreb"-type Amides

Example B1

3-bromo-N-methoxy-N-methylbenzamide (B1)

100.0 g (0.447 mol) 3-bromobenzoyl chloride was added to an ice cooled solution of 48.9 g (0.491 mol) N,O-dimethylhydroxylamine hydrochloride and 140.0 ml (1.00 mol) triethylamine in 650 ml dry dichloromethane over a period of 30 minutes. After additional stirring for 30 minutes, 370 ml water was added and the organic layer dried over sodium sulfate. Fractionated distillation in vacuo yielded 101.4 g (93%) B1, b.p. 114–129° C./0.07 mbar, as a colorless oil.

MS: 246 (API+) $^1$H-NMR (250 MHz, CDCl$_3$): δ=3.35 (s, 3H, NCH$_3$), 3.56 (s, 3H, OCH$_3$), 7.27 (t, 1H, 5-H), 7.58 (m, 1H, 4-H), 7.60 (m, 1H, 6-H), 7.82 (t, 1H, 2-H).

Example B2

3-iodo-N-methoxy-N-methylbenzamide (B2)

An analogous reaction to that described in example B1, but starting with 3-iodobenzoyl chloride yielded B2.

MS: 292 (API+)

Example B3

3-chloro-N-methoxy-N-methylbenzamide (B3)

An analogous reaction to that described in example B1, but starting with 3-chlorobenzoyl chloride yielded B3.

MS: 200 (API+)

Example B4

3-benzyloxy-N-methoxy-N-methylbenzamide (B4)

To a suspension of 136.8 g (0.60 mol) 3-benzyloxybenzoic acid in 1200 ml dichloromethane 60.6 g (0.6 mol) triethylamine was added at 10° C. A solution of 64.8 g (0.60 mol) ethyl chloroformiate in 100 ml dichloromethane was added over a period of 15 minutes keeping the temperature between 10° C. and 15° C. After stirring for 40 minutes and addition of 58.2 g (0.60 mol) N,O-dimethylhydroxylamine hydrochloride, a solution of 60.6 g (0.60 mol) triethylamine was added over a period of 20 minutes at 10–15° C. The further workup is the same as described in example B1. Yield: 131.9 g (81%) B4.

MS: 273 (API+)

Example B5

3-hydroxy-N-methoxy-N-methylbenzamide (B5)

To a solution of 100 g (0.37 mol) B4 in 750 ml tetrahydrofurane 10 g Pd/C (10%) were added and the mixture was hydrogenated at atmospheric pressure for 2 hours. The catalyst was filtered off and the filtrate was evaporated to yield 66.0 g B5 (98%).

MS: 182 (API+), 180 (API−)

Example B6

3-methoxymethoxy-N-methoxy-N-methylbenzamide (B6)

69.0 g (380 mmol) of B5 were dissolved in 500 ml of dry dimethylformamide, cooled to 0° C. and 11.5 g (480 mmol)

sodium hydride were added and the mixture was allowed to stir for 10 minutes. A solution of 31.2 ml (418 mmol) (chloromethyl)methylether in 100 ml of dry diemthylformamide was added at this temperature over a period of 30 minutes. After stirring at room temperature overnight, the solvent was distilled off and the residue was partitionated between 400 ml of dichloromethane and 100 ml of water. The organic layer was washed with 50 ml of aqueous sodium hydrogen carbonate and two times with water (80 ml each) and finally dried over sodium sulfate. Removing the solvent in vacuo yielded 73.5 g (87%) B6 as a colorless oil which was used without further purification.

MS: 226 (API+)

Example B7

3-(4'-cyanobenzyloxy)-N-methoxy-N-methylbenzamide (B7)

An analogous reaction to that described in example B6, but starting with 4-cyanobenzylic bromide yielded B7.

MS: 297 (API+)

Example B8

3-(4'-chlorobenzyloxy)-N-methoxy-N-methylbenzamide (B8)

1.81 g (10.0 mmol) B5, 1.57 g (11.0 mmol) 4-chlorobenzylic alcohol and 3.03 g (15.0 mmol) tributylphosphine were dissolved in 100 ml tetrahydrofurane and 3.78 g (15.0 mmol) azodicarbonylpiperidine was added at 10° C. The mixture was stirred at room temperature overnight. After removal of the precipitate, the mother liquor was evaporated to dryness and the residue was taken up with ethyl acetate. After filtration and washing with aqueous sodium hydrogen carbonate, 2 N HCl and water, the organic phase was dried over sodium sulfate end the solvent was removed in vacuo.

Chromatography of the residue on SiGel (n-heptane/ethyl acetate 2:1) yielded 2.8 g (90%) B8.

MS: 306 (API+)

Example B9

3-(4'-methoxybenzyloxy)-N-methoxy-N-methylbenzamide (B9)

An analogous reaction to that described in example B8, but starting with 4-methoxybenzylic alcohol yielded B9.

MS: 302 (API+)

Example B10

3-(allyloxy)-N-methoxy-N-methylbenzamide (B10)

To a solution of 10.8 g (59.6 mmol) B5 and 5.42 ml (71.5 mmol) allylic bromide in 300 ml 2-butanone 41.1 g (298 mmol) potassium carbonate were added. After stirring at 60° C. for 15 hours the solvent was distilled off and the residue partitionated between ethyl acetate and water. The organic layer was dried over sodium sulfate and the solvent removed in vacuo. Yield: 12.1 g (92%) B10 as a yellowish oil which was used without further purification.

MS: 222 (API+)

Example B11

4-chloro-N-methoxy-N-methylbenzamide (B11)

An analogous reaction to that described in example B1, but starting with 4-chlorobenzoyl chloride yielded B 11.

MS: 200 (API+)

Example B12

4-fluoro-N-methoxy-N-methylbenzamide (B11)

An analogous reaction to that described in example B1, but starting with 4-fluorobenzoyl chloride yielded B12.

MS: 184 (API+)

Example B13

4-chloro-3-methoxy-N-methoxy-N-methylbenzamide (B13)

An analogous reaction to that described in example B1, but starting with 4-chloro-3-methoxybenzoyl chloride yielded B13.

MS: 230 (API+)

Example B14

3-benzyloxy-4-fluoro-N-methoxy-N-methylbenzamide (B14)

An analogous reaction to that described in example B4, but starting with 3-benzyloxy-4-fluorobenzoic acid yielded B14.

MS: 290 (API+)

Example B15

3-benzyloxy-4-methyl-N-methoxy-N-methylbenzamide (B15)

An analogous reaction to that described in example B4, but starting with 3-benzyloxy-4-methoxybenzoic acid yielded B15.

MS: 286 (API+)

Example B16

3-methylthio-N-methoxy-N-methylbenzamide (B16)

An analogous reaction to that described in example B4, but starting with 3-methylthiobenzoic yielded acid B16.

MS: 212 (API+)

C Synthesis of the "Ethanones"

Example C1

1-(3-bromophenyl)-2-(2-methylthiopyrimidin-4-yl)-ethanone (C1)

19.8 ml (140 mmol) diisopropylamine were dissolved in 250 ml dry tetrahydrofurane and cooled to −75° C. and 87.6 ml of a solution of n-butyllithium (1.6 M in hexane, 140 mmol) was added over a period of 20 minutes. After stirring for 15 minutes at −75° C. a solution of 13.1 g (93 mmol) 2-methylthio-4-methylpyrimidine in 80 ml dry tetrahydrofurane was added within 30 minutes at −75° C. and the mixture was stirred for additional 15 minutes. Then a solution of 25.1 g (103 mmol) B1 was added within 30 minutes at −75° C. The mixture was allowed to warm up to room temperature and was poured on 600 ml ethyl acetate/water (1:1). The aqueous layer was extracted with 50 ml ethyl acetate and the combined organic layers were dried over sodium sulphate. Removal of the solvent in vacuo yielded 23.3 g (77%) C1, m.p. 98–101° C.

MS: M=325 (ESI+), M=323 (ESI−). $^1$H-NMR (250 MHz, CDCl$_3$): "enole" (75%) δ=2.62 (s, 3H, SCH$_3$), 5.97 (s, 1H, CH=C), 6.66 (s, 1H, 5-H-pyrimidine), 8.34 (d, 1H, 6-H-pyrimidine), 14.7 (s, 1H, OH). "keto" (25%) δ=2.52 (s, 3H, SCH$_3$), 4.35 (s, 2H, CH$_2$), 6.97 (d, 1H, 5-H-pyrimidin), 8.46 (d, 1H, 6-H-pyrimidin).

Example C2

1-(3-iodophenyl)-2-(2-methylthiopyrimidin-4-yl)-ethanone (C2)

An analogous reaction to that described in example C1, but starting with B2 yielded C2.

MS: 371 (API+)

Example C3

1-(3-chlorophenyl)-2-(2-methylthiopyrimidin-4-yl)-ethanone (C3)

An analogous reaction to that described in example C1, but starting with B3 yielded C3.

MS: 279 (API+)

Example C4

1-(3-benzyloxyphenyl)-2-(2-methylthiopyrimidin-4-yl)-ethanone (C4)

An analogous reaction to that described in example C1, but starting with B4 yielded C4.

MS: 351 (API+)

Example C5

1-(3-hydroxyphenyl)-2-(2-methylthiopyrimidin-4-yl)-ethanone (C5)

Example C6

1-(3-methoxymethoxyphenyl)-2-(2-methylthiopyrimidin-4-yl)-ethanone (C6)

An analogous reaction to that described in example C1, but starting with B6 yielded C6.

MS: 305 (API+)

Example C7

1-(3-[4'-cyanobenzyloxy]phenyl)-2-(2-methylthiopyrimidin-4-yl)-ethanone (C7)

An analogous reaction to that described in example C1, but starting with B7 yielded C7.

MS: 376 (API+)

Example C8

1-(3-[4'-chlorobenzyloxy]phenyl)-2-(2-methylthiopyrimidin-4-yl)-ethanone (C8)

An analogous reaction to that described in example C1, but starting with B8 yielded C8.

MS: 385 (API+)

Example C9

1-(3-[4'-methoxybenzyloxy]phenyl)-2-(2-methylthiopyrimidin-4-yl)-ethanone (C9)

An analogous reaction to that described in example C1, but starting with B9 yielded C9.

MS: 381 (API+)

Example C10

1-(3-allyloxyphenyl)-2-(2-methylthiopyrimidin-4-yl)-ethanone (C10)

An analogous reaction to that described in example C1, but starting with B10 yielded C10.

MS: 301 (API+)

Example C11

1-(4-chlorophenyl)-2-(2-methylthiopyrimidin-4-yl)-ethanone (C11)

An analogous reaction to that described in example C1, but starting with B11 yielded C11.

MS: 279 (API+)

Example C12

1-(4-fluorophenyl)-2-(2-methylthiopyrimidin-4-yl)-ethanone (C12)

An analogous reaction to that described in example C1, but starting with B12 yielded C12.

MS: 263 (API+)

Example C13

1-(4-chloro-3-methoxyphenyl)-2-(2-methylthiopyrimidin-4-yl)-ethanone (C13)

An analogous reaction to that described in example C1, but starting with B13 yielded C13.

MS: 309 (API+)

Example C14

1-(3-benzyloxy-4-fluorophenyl)-2-(2-methylthiopyrimidin-4-yl)-ethanone (C14)

An analogous reaction to that described in example C1, but starting with B14 yielded C14.

MS: 369 (API+)

Example C15

1-(3-benzyloxy-4-methylphenyl)-2-(2-methylthiopyrimidin-4-yl)-ethanone (C15)

An analogous reaction to that described in example C1, but starting with B15 yielded C15.

MS: 365 (API+)

Example C16

1-(3-methylthiophenyl)-2-(2-methylthiopyrimidin-4-yl)-ethanone (C16)

An analogous reaction to that described in example C1, but starting with B16 yielded C16.

MS: 291 (API+)

Example C17

1-(3-trimethylsilylacetylenyl)-2-(2-methylthiopyrimidin-4-yl)-ethanone (C17)

To a solution of 16.3 g (44.0 mmol) C2 in 260 ml dry THF at 10° C. under nitrogen 1.5 g (2.2 mmol) bis- (triphenylphosphine)palladium-II-chloride, 900 mg (4.7 mmol) copper-I-iodide, 12 ml (85 mmol) trimethylsilylacetylene and 30 ml diisopropylamine were added and the mixture was stirred and successively allowed to warm up to room temperature. After stirring at room temperature overnight, 260 ml water were added and the mixture was extracted twice with ether. The organic layer was separated, dried and evaporated to dryness. Column chromatography of the residue on SiGel (iso-hexane/ethyl acetate 3:1) yielded 12.5 g (83%) C17.

MS: 341 (API+)

D Synthesis of the "Ketoximes"

Example D1

1-(3-bromophenyl)-2-(2-methylthiopyrimidin-4-yl)-2-hydroxyiminoethanone(D1)

12.75 g (39.5 mmol) C1 were dissolved in a mixture of 173 ml glacial acid, 136 ml tetrahydrofurane and 17 ml water. After cooling to 5° C. a solution of 3.24 g (47.0 mmol) sodium nitrite in 25 ml water was added keeping the temperature between 5° C. and 10° C. The cooling was removed and the mixture stirred for 6 hours at room temperature. After removal of the solvent in vacuo 320 ml water and 320 ml ethyl acetate were added. The pH was adjusted to 8 with 3 N NaOH. The phases were separated and the aqueous layer was extracted with 50 ml ethyl acetate. The combined organic layers were dried over sodium sulfate and the solvent was removed in vacuo. The residue was treated with diethylether, filtered off and dried. Yield: 8.33 g (60%) D1, m.p. 156–158° C.

MS: M=352 (ESI+), M=340 (ESI−). $^1$H-NMR (250 MHz, $D_6$-DMSO):δ=2.20 (s, 3H, $SCH_3$), 7.54 (t, 1H, 5-H—BrPh), 7.66 (d, 1H, 5-H-pyrimidine), 7.81(m, 1H), 7.92 (m, 2H), 8.70 (d, 1H, 6-H-pyrimidine), 12.9 (s, 1H, OH).

Example D2

1-(3-iodophenyl)-2-(2-methylthiopyrimidin-4-yl)-2-hydroxyiminoethanone(D2)

An analogous reaction to that described in example D1, but starting with C2 yielded D2 in 88% yield.

MS: 400 (API+), 398 (API−)

Example D3

1-(3-chlorophenyl)-2-(2-methylthiopyrimidin-4-yl)-2-hydroxyiminoethanone(D3)

An analogous reaction to that described in example D1, but starting with C3 gave D3 in 76% yield.

MS: 308 (API+)

Example D4

1-(3-benzyloxyphenyl)-2-(2-methylthiopyrimidin-4-yl)-2-hydroxyiminoethanone(D4)

An analogous reaction to that described in example D1, but starting with C4 gave D4 in 86% yield.

MS: M=380 (API+), M=378 (API−)

Example D5

1-(3-hydroxyphenyl)-2-(2-methylthiopyrimidin-4-yl)-2-hydroxyiminoethanone(D5)

334 mg (1.0 mmol) D6 were dissolved in 20 ml methanol, 200 µl 37% HCl were added and the mixture was stirred at room temperature overnight. After removal of the solvent column chromatography on SiGel using a heptane-ethyl acetate gradient returned 190 mg (65%) D5 as a white solid.

MS: 290 (API+), 288 (API−) $^1$H-NMR (400 MHz, $D_6$-DMSO):δ=2.22 (s, 3H, $SCH_3$), 7.08–7.11 (m, 1H), 7.16–7.20 (m, 1H), 7.20–7.24 (m, 1H), 7.37 (t, 7.8 Hz, 1H), 7.64 (d, 5.1 Hz, 1H, 5-H-pyrimidine), 8.70 (d, 5.1 Hz, 1H, 6-H-pyrimidine), 9.91 (s, 1H, OH), 12.73 (s, 1H, OH). $^{13}$C-NMR (101 MHz, $D_6$-DMSO):δ=13.6 ($SCH_3$), 111.6, 114.7, 119.9, 121.9, 130.7, 136.4, 154.2, 158.2, 158.8, 159.4, 171.8, 193.5

Example D6

1-(3-methoxymethoxyphenyl)-2-(2-methylthiopyrimidin-4-yl)-2-hydroxyiminoethanone (D6)

An analogous reaction to that described in example D1, but starting with C6 gave D6 in 79% yield.

MS: 334 (API+), 332 (API−)

Example D7

1-(3-[4'-cyanobenzyloxy]phenyl)-2-(2-methylthiopyrimidin-4-yl)-2-hydroxyiminoethanone (D7)

An analogous reaction to that described in example D1, but starting with C7 gave C7 in 72% yield.

MS: 405 (API+)

Example D8

1-(3-[4'-chlorobenzyloxy]phenyl)-2-(2-methylthiopyrimidin-4-yl)-2-hydroxyiminoethanone (D8)

An analogous reaction to that described in example D1, but starting with C8 gave D8 in 66% yield.

MS: M=414 (API+), 412 (API−)

Example D9

1-(3-[4'-methoxybenzyloxy]phenyl)-2-(2-methylthiopyrimidin-4-yl)-2-hydroxyiminoethanone (D9)

An analogous reaction to that described in example D1, but starting with C9 gave D9 in 74% yield.

MS: 410 (API+)

Example D10

1-(3-allyloxyphenyl)-2-(2-methylthiopyrimidin-4-yl)-2-hydroxyiminoethanone(D10)

An analogous reaction to that described in example D1, but starting with C10 gave D10 in 84% yield.

MS: 330 (API+), 328 (API−)

Example D11

1-(4-chlorophenyl)-2-(2-methylthiopyrimidin-4-yl)-2-hydroxyiminoethanone(D11)

An analogous reaction to that described in example D1, but starting with C11 gave D11 in 85% yield.

MS: 308 (API+), 306 (API−)

Example D12

1-(4-fluorophenyl)-2-(2-methylthiopyrimidin-4-yl)-2-hydroxyiminoethanone(D12)

An analogous reaction to that described in example D1, but starting with C12 gave D12 in 72% yield.

MS: 292 (API+), 290 (API−)

Example D13

1-(4-chloro-3-methoxyphenyl)-2-(2-methylthiopyrimidin-4-yl)-2-hydroxyiminoethanone (D13)

An analogous reaction to that described in example D1, but starting with C13 gave D13 in 98% yield.

MS: 338 (API+), 336 (API−)

Example D14

1-(3-benzyloxy-4-fluorophenyl)-2-(2-methylthiopyrimidin-4-yl)-2-hydroxyiminoethanone (D14)

An analogous reaction to that described in example D1, but starting with C14 gave D14 in 74% yield.

MS: 398 (API+), 396 (API−)

Example D15

1-(3-benzyloxy-4-methylphenyl)-2-(2-methylthiopyrimidin-4-yl)-2-hydroxyiminoethanone (D15)

An analogous reaction to that described in example D1, but starting with C15 gave D15 in 79% yield.

MS: 394 (API+), 392 (API−)

Example D16

1-(3-methylthiophenyl)-2-(2-methylthiopyrimidin-4-yl)-2-hydroxyiminoethanone(D16)

An analogous reaction to that described in example D1, but starting with C16 gave D16 in 71% yield.

MS: 320 (API+), 318 (API−)

Example D17

1-(3-trimethylsilylacetylenyl)-2-(2-methylthiopyrimidin-4-yl)-2-hydroxyiminoethanone (D17)

An analogous reaction to that described in example D1, but starting with C17 gave D17 in 54% yield, m.p. 140–145° C.

MS: 370 (API+), 368 (API−)

E Synthesis of the "2,6-dichlorophenyl-N-hydroxy imidazoles"

Example E1.1

2-(2,6-dichlorophenyl)-4-(3-bromophenyl)-5-(2-methylthiopyrimidin-4-yl)-N-hydroxy-imidazole (E1.1)

27.9 g (79.3 mmol) D1, 14.6 g (83.2 mmol) 2,6-dichlorobenzaldehyde and 61.0 g (793 mmol) ammonium acetate were dissolved in 550 ml glacial acid and stirred at 100° C. for 150 minutes. The glacial acid was distilled off in vacuo and the residue was treated with ethyl acetate/water and justified at pH 8 with concentrated aqueous ammonia. The precipitate was filtered off, washed with ethyl acetate and dried to yield 24.8 g (62%) E1, m.p. 251–253° C. The aqueous layer was extracted with ethyl acetate and the combined organic layers dried over sodium sulfate. Removal of the solvent in vacuo and treatment with diethylether yielded another 8.9 g (22%) E1.1.

MS: M=509 (API+), 507 (API−)

Example E1.2

2-(2,6-dichloro-4-hydroxyphenyl)-4-(3-bromophenyl)-5-(2-methylthiopyrimidin-4-yl)-N-hydroxy-imidazole (E1.2)

An analogous reaction to that described in example E1.1, but starting with A1 gave E1.2 in 85% yield.

MS: M=525 (API+), 523 (API−)

Example E1.3

2-(2,6-dichloro-4-hydroxymethylphenyl)-4-(3-bromophenyl)-5-(2-methylthiopyrimidin-4-yl)-N-hydroxy-imidazole (E1.3)

An analogous reaction to that described in example E1.1, but starting with A3 gave E1.3 in 99% yield.

MS: M=539 (API+), 537 (API−)

Example E1.4

2-(2,6-dichloro-4-(2-methoxy-ethoxymethoxy)phenyl)-4-(3-bromophenyl)-5-(2-methylthiopyrimidin-4-yl)-N-hydroxy-imidazole (E1.4)

An analogous reaction to that described in example E1.1, but starting with A23 gave E1.4 in 72% yield.

MS: M=613 (API+), 611 (API−)

Example E2.1

2-(2,6-dichlorophenyl)-4-(3-iodophenyl)-5-(2-methylthiopyrimidin-4-yl)-N-hydroxy-imidazole (E2.1)

An analogous reaction to that described in example E1.1, but starting with D2 gave E2.1 in 76% yield.

MS: M=555 (API+), 553 (API−)

Example E2.2

2-(2,6-dichloro-4-hydroxyphenyl)-4-(3-iodophenyl)-5-(2-methylthiopyrimidin-4-yl)-N-hydroxy-imidazole (E2.2)

An analogous reaction to that described in example E1.1, but starting with D2 and A1 gave E2.2 in 99% yield.

MS: M=571 (API+), 569 (API−)

Example E2.3

2-(2,6-dichloro-4-hydroxymethylphenyl)-4-(3-iodophenyl)-5-(2-methylthiopyrimidin-4-yl)-N-hydroxy-imidazole (E2.3)

An analogous reaction to that described in example E1.1, but starting with D2 and A3 gave E2.3 in 99% yield.

MS: M=585 (API+), 583 (API−)

Example E3.1

2-(2,6-dichlorophenyl)-4-(3-chlorophenyl)-5-(2-methylthiopyrimidin-4-yl)-N-hydroxy-imidazole (E3.1)

An analogous reaction to that described in example E1.1, but starting with D3 gave E3.1 in 85% yield.

MS: M=465 (API+), 463 (API−)

Example E3.2

2-(2,6-dichloro-4-hydroxyphenyl)-4-(3-chlorophenyl)-5-(2-methylthiopyrimidin-4-yl)-N-hydroxy-imidazole (E3.2)

Example E3.3

2-(2,6-dichloro-4-hydroxymethylphenyl)-4-(3-chlorophenyl)-5-(2-methylthiopyrimidin-4-yl)-N-hydroxy-imidazole (E3.3)

An analogous reaction to that described in example E1.1, but starting with D3 and A3 gave E3.3 in 67% yield.
MS: M=495 (API+), 493 (API−)

Example E4.1

2-(2,6-dichlorophenyl)-4-(3-benzyloxyphenyl)-5-(2-methylthiopyrimidin-4-yl)-N-hydroxy-imidazole (E4.1)

An analogous reaction to that described in example E1.1, but starting with D4 gave E4.1 in 63% yield.
MS: M=535 (API+), 533 (API−)

Example E4.2

2-(2,6-dichloro-4-hydroxyphenyl)-4-(3-benzyloxyphenyl)-5-(2-methylthiopyrimidin-4-yl)-N-hydroxy-imidazole (E4.2)

An analogous reaction to that described in example E1.1, but starting with D4 and A1 gave E4.2 in 82% yield.
MS: M=551 (API+), 549 (API−)

Example E4.3

2-(2,6-dichloro-4-hydroxymethylphenyl)-4-(3-benzyloxyphenyl)-5-(2-methylthiopyrimidin-4-yl)-N-hydroxy-imidazole (E4.3)

An analogous reaction to that described in example E1.1, but starting with D4 and A3 gave E4.3 in 74% yield.
MS: M=563 (API−)

Example E4.4

2-(2,6-dichloro-4-[methoxycarbonylmethoxy]phenyl)-4-(3-benzyloxyphenyl)-5-(2-methylthiopyrimidin-4-yl)-N-hydroxy-imidazole (E4.4)

An analogous reaction to that described in example E1.1, but starting with D4 and A4 gave E4.4 in 72% yield.
MS: M=623 (API+), 621 (API−)

Example E4.5

2-(2,6-dichloro-4-[ethoxycarbonylmethoxy]phenyl)-4-(3-benzyloxyphenyl)-5-(2-methylthiopyrimidin-4-yl)-N-hydroxy-imidazole (E4.5)

An analogous reaction to that described in example E1.1, but starting with D4 and A5 gave E4.5 in 73% yield.
MS: M=635 (API−)

Example E4.6

(rac)-2-(2,6-dichloro-4-(2,2-dimethyl-[1,3]-dioxolane-4-ylmethoxy)phenyl)-4-(3-benzyloxyphenyl)-5-(2-methylthiopyrimidin-4-yl)-N-hydroxy-imidazole (E4.6)

Example E4.6.1

(R)-2-(2,6-dichloro-4-(2,2-dimethyl-[1,3]-dioxolane-4-ylmethoxy)phenyl)-4-(3-benzyloxyphenyl)-5-(2-methylthiopyrimidin-4-yl)-N-hydroxy-imidazole (E4.6.1)

An analogous reaction to that described in example E1.1, but starting with D4 and A8.1 gave E4.6.1 in 38% yield.
MS: M=665 (API+), 663 (API−)

Example E4.6.2

(S)-2-(2,6-dichloro-4-(2,2-dimethyl-[1,3]-dioxolane-4-ylmethoxy)phenyl)-4-(3-benzyloxyphenyl)-5-(2-methylthiopyrimidin-4-yl)-N-hydroxy-imidazole (E4.6.2)

An analogous reaction to that described in example E1.1, but starting with D4 and A8.2 gave E4.6.2 in 41% yield.
MS: M=665 (API+), 663 (API−)

Example E4.7

(rac)-2-(2,6-dichloro-4-(2,3-dihydroxypropoxy)phenyl)-4-(3-benzyloxyphenyl)-5-(2-methylthiopyrimidin-4-yl)-N-hydroxy-imidazole (E4.7)

Example E4.7.1

(R)-2-(2,6-dichloro-4-(2,3-dihydroxypropoxy)phenyl)-4-(3-benzyloxyphenyl)-5-(2-methylthiopyrimidin-4-yl)-N-hydroxy-imidazole (E4.7.1)

E4.7.1 was isolated as a byproduct (partly deprotection of the ketal in glacial acid) from example E4.6.2 in 42% yield
MS: M=625 (API+), 623 (API−)

Example E4.7.2

(S)-2-(2,6-dichloro-4-(2,3-dihydroxypropoxy)phenyl)-4-(3-benzyloxyphenyl)-5-(2-methylthiopyrimidin-4-yl)-N-hydroxy-imidazole (E4.7.2)

E4.7.2 was isolated as a byproduct (partly deprotection of the ketal in glacial acid) from example E4.6.1 in 37% yield
MS: M=625 (API+), 623 (API−)

Example E4.8

2-(2,6-dichloro-4-(dimethylphoshinoylmethoxy)phenyl)-4-(3-benzyloxyphenyl)-5-(2-methylthio-pyrimidin-4-yl)-N-hydroxy-imidazole (E4.8)

An analogous reaction to that described in example E1.1, but starting with D4 and A7 gave E4.8 in 79% yield.
MS: M=641 (API+), 639 (API−)

Example E4.9

2-(2,6-dichloro-4-methylthiophenyl)-4-(3-benzyloxyphenyl)-5-(2-methylthiopyrimidin-4-yl)-N-hydroxy-imidazole (E4.9)

Example E4.10

2-(2,6-dichloro-4-methanesulfinylphenyl)-4-(3-benzyloxyphenyl)-5-(2-methylthiopyrimidin-4-yl)-N-hydroxy-imidazole (E4.10)

An analogous reaction to that described in example E1.1, but starting with D4 and A10 gave E4.10 in 54% yield.
MS: M=599 (API+), 597 (API−)

Example E4.11

2-(2,6-dichloro-4-methanesulfonylphenyl)-4-(3-benzyloxyphenyl)-5-(2-methylthiopyrimidin-4-yl)-N-hydroxy-imidazole (E4.11)

Example E4.12

2-(2,6-dichloro-4-cyanomethyloxyphenyl)-4-(3-benzyloxyphenyl)-5-(2-methylthiopyrimidin-4-yl)-N-hydroxy-imidazole (E4.12)

An analogous reaction to that described in example E1.1, but starting with D4 and A6 gave E4.12 in 68% yield.
MS: M=590 (API+), 588 (API−)

Example E4.13

2-(2,6-dichloro-4-(N-morpholino)methylphenyl)-4-(3-benzyloxyphenyl)-5-(2-methylthiopyrimidin-4-yl)-N-hydroxy-imidazole (E4.13)

Example E4.14

2-(2,6-dichloro-4-ethoxycarbonylmethylthiomethylphenyl)-4-(3-benzyloxyphenyl)-5-(2-methylthiopyrimidin-4-yl)-N-hydroxy-imidazole (E4.14)

Example E4.15

2-(2,6-dichloro-4-hydroxyethylthiomethylphenyl)-4-(3-benzyloxyphenyl)-5-(2-methylthiopyrimidin-4-yl)-N-hydroxy-imidazole (E4.15)

Example E4.16

2-(2,6-dichloro-4-(N-morpholinoethylaminomethyl)phenyl)-4-(3-benzyloxyphenyl)-5-(2-methylthiopyrimidin-4-yl)-N-hydroxy-imidazole (E4.16)

Example E4.17

2-(2,6-dichloro-4-[2-(tert-butyldimethylsilanyloxy)-1-(tert-butyldimethylsilanyloxymethyl)-ethoxy]-phenyl)-4-(3-benzyloxyphenyl)-5-(2-methylthiopyrimidin-4-yl)-N-hydroxy-imidazole (E4.17)

An analogous reaction to that described in example E1.1, but starting with D4 and A24 gave E4.17 which was used without further purification.
MS: M=853 (API+)

Example E4.18

2-(2,6-dichloro-4-[3-(tert-butyldimethylsilanyloxy)-2-(tert-butyldimethylsilanyloxymethyl)-propoxy]-phenyl)-4-(3-benzyloxyphenyl)-5-(2-methylthiopyrimidin-4-yl)-N-hydroxy-imidazole (E4.18)

Example E5.1

2-(2,6-dichlorophenyl)-4-(3-hydroxyphenyl)-5-(2-methylthiopyrimidin-4-yl)-N-hydroxy-imidazole (E5.1)

Example E5.2

2-(2,6-dichloro-4-hydroxyphenyl)-4-(3-hydroxyphenyl)-5-(2-methylthiopyrimidin-4-yl)-N-hydroxy-imidazole (E5.2)

Example E5.3

2-(2,6-dichloro-4-hydroxymethylphenyl)-4-(3-hydroxyphenyl)-5-(2-methylthiopyrimidin-4-yl)-N-hydroxy-imidazole (E5.3)

An analogous reaction to that described in example E1.1, but starting with D5 and A3 gave E5.3 in 76% yield.
MS: M=475 (API+), 473 (API−)

Example E6.1

2-(2,6-dichlorophenyl)-4-(3-methoxymethoxyphenyl)-5-(2-methylthiopyrimidin-4-yl)-N-hydroxy-imidazole (E6.1)

An analogous reaction to that described in example E1.1, but starting with D6 gave E6.1 in 99% yield.
MS: M=487 (API−)

Example E6.2

2-(2,6-dichloro-4-hydroxyphenyl)-4-(3-methoxymethoxyphenyl)-5-(2-methylthiopyrimidin-4-yl)-N-hydroxy-imidazole (E6.2)

An analogous reaction to that described in example E1.1, but starting with D6 and A1 gave E6.2 in 99% yield.
MS: M=505 (API+), 503 (API−)

Example E6.3

2-(2,6-dichloro-4-hydroxymethylphenyl)-4-(3-methoxymethoxyphenyl)-5-(2-methylthiopyrimidin-4-yl)-N-hydroxy-imidazole (E6.3)

An analogous reaction to that described in example E1.1, but starting with D6 and A3 gave E6.3 in 99% yield.
MS: M=519 (API+), 517 (API−)

Example E6.4

2-(2,6-dichloro-4-[methoxycarbonylmethoxy]phenyl)-4-(3-methoxymethoxyphenyl)-5-(2-methylthio-pyrimidin-4-yl)-N-hydroxy-imidazole (E6.4)

Example E6.5

2-(2,6-dichloro-4-[ethoxycarbonylmethoxy]phenyl)-4-(3-methoxymethoxyphenyl)-5-(2-methylthio-pyrimidin-4-yl)-N-hydroxy-imidazole (E6.5)

An analogous reaction to that described in example E1.1, but starting with D6 and A5 gave E6.5 in 71% yield.
MS: M=591 (API+), 589 (API−)

Example E6.6

(rac)-2-(2,6-dichloro-4-(2,2-dimethyl-[1,3]-dioxolane-4-ylmethoxy)phenyl)-4-(3-methoxymethoxy-phenyl)-5-(2-methylthiopyrimidin-4-yl)-N-hydroxy-imidazole (E6.6)

Example E6.6.1

(R)-2-(2,6-dichloro-4-(2,2-dimethyl-[1,3]-dioxolane-4-ylmethoxy)phenyl)-4-(3-methoxymethoxyphenyl)-5-(2-methylthiopyrimidin-4-yl)-N-hydroxy-imidazole (E6.6.1)

Example E6.6.2

(S)-2-(2,6-dichloro-4-(2,2-dimethyl-[1,3]-dioxolane-4-ylmethoxy)phenyl)-4-(3-methoxymethoxyphenyl)-5-(2-methylthiopyrimidin-4-yl)-N-hydroxy-imidazole (E6.6.2)

Example E6.7

(rac)-2-(2,6-dichloro-4-(2,3-dihydroxypropoxy)phenyl)-4-(3-methoxymethoxyphenyl)-5-(2-methylthio-pyrimidin-4-yl)-N-hydroxy-imidazole (E6.7)

Example E6.7.1

(R)-2-(2,6-dichloro-4-(2,3-dihydroxypropoxy)phenyl)-4-(3-methoxymethoxyphenyl)-5-(2-methylthio-pyrimidin-4-yl)-N-hydroxy-imidazole (E6.7)

Example E6.7.2

(S)-2-(2,6-dichloro-4-(2,3-dihydroxypropoxy)phenyl)-4-(3-methoxymethoxyphenyl)-5-(2-methylthio-pyrimidin-4-yl)-N-hydroxy-imidazole (E6.7)

Example E6.8

2-(2,6-dichloro-4-(dimethylphoshinoylmethoxy)phenyl)-4-(3-methoxymethoxyphenyl)-5-(2-methylthio-pyrimidin-4-yl)-N-hydroxy-imidazole (E6.8)

An analogous reaction to that described in example E1.1, but starting with D6 and A7 gave E6.8 in 86% yield.
MS: M=595 (API+), 593 (API−)

Example E6.9

2-(2,6-dichloro-4-methanesulfinylphenyl)-4-(3-methoxymethoxyphenyl)-5-(2-methylthio-pyrimidin-4-yl)-N-hydroxy-imidazole (E6.9)

An analogous reaction to that described in example E1.1, but starting with D6 and A10 gave E6.9 in 73% yield.
MS: M=551 (API+), 549 (API−)

Example E7.1

2-(2,6-dichlorophenyl)-4-(3-[4'-cyanobenzyloxy]phenyl)-5-(2-methylthiopyrimidin-4-yl)-N-hydroxy-imidazole (E7.1)

Example E7.2

2-(2,6-dichloro-4-hydroxyphenyl)-4-(3-[4'-cyanobenzyloxy]phenyl)-5-(2-methylthio-pyrimidin-4-yl)-N-hydroxy-imidazole (E7.2)

Example E7.3

2-(2,6-dichloro-4-hydroxymethylphenyl)-4-(3-[4'-cyanobenzyloxy]phenyl)-5-(2-methylthiopyrimidin-4-yl)-N-hydroxy-imidazole (E7.3)

Example E7.4

2-(2,6-dichloro-4-(2-hydroxyethoxyphenyl)-4-(3-[4'-cyanobenzyloxy]phenyl)-5-(2-methylthiopyrimidin-4-yl)-N-hydroxy-imidazole (E7.4)

An analogous reaction to that described in example E1.1, but starting with D7 and A12 gave E7.4 in 84% yield.
MS: M=620 (API+), 618 (API−)

Example E8.1

2-(2,6-dichlorophenyl)-4-(3-[4'-chlorobenzyloxy]phenyl)-5-(2-methylthiopyrimidin-4-yl)-N-hydroxy-imidazole (E8.1)

An analogous reaction to that described in example E1.1, but starting with D8 gave E8.1 in 99% yield.
MS: M=571 (API+), 569 (API−)

Example E8.2

2-(2,6-dichloro-4-hydroxyphenyl)-4-(3-[4'-chlorobenzyloxy]phenyl)-5-(2-methylthiopyrimidin-4-yl)-N-hydroxy-imidazole (E8.2)

An analogous reaction to that described in example E1.1, but starting with D8 and A1 gave E8.2 in 99% yield.
MS: M=587 (API+), 585 (API−)

Example E8.3

2-(2,6-dichloro-4-hydroxymethylphenyl)-4-(3-[4'-chlorobenzyloxy]phenyl)-5-(2-methylthiopyrimidin-4-yl)-N-hydroxy-imidazole (E8.3)

Example E9.1

2-(2,6-dichlorophenyl)-4-(3-[4'-methoxybenzyloxy]phenyl)-5-(2-methylthiopyrimidin-4-yl)-N-hydroxy-imidazole (E9.1)

Example E9.2

2-(2,6-dichloro-4-hydroxyphenyl)-4-(3-[4'-methoxybenzyloxy]phenyl)-5-(2-methylthio-pyrimidin-4-yl)-N-hydroxy-imidazole (E9.2)

Example E9.3

2-(2,6-dichloro-4-hydroxymethylphenyl)-4-(3-[4'-methoxybenzyloxy]phenyl)-5-(2-methylthiopyrimidin-4-yl)-N-hydroxy-imidazole (E9.3)

Example E10.1

2-(2,6-dichlorophenyl)-4-(3-allyloxyphenyl)-5-(2-methylthiopyrimidin-4-yl)-N-hydroxy-imidazole (E10.1)

An analogous reaction to that described in example E1.1, but starting with D10 gave E10.1 in 94% yield.
MS: M=485 (API+), 483 (API−)

Example E10.2

2-(2,6-dichloro-4-hydroxyphenyl)-4-(3-allyloxyphenyl)-5-(2-methylthiopyrimidin-4-yl)-N-hydroxy-imidazole (E10.2)

Example E10.3

2-(2,6-dichloro-4-hydroxymethylphenyl)-4-(3-allyloxyphenyl)-5-(2-methylthiopyrimidin-4-yl)-N-hydroxy-imidazole (E10.3)

Example E11.1

2-(2,6-dichlorophenyl)-4-(4-chlorophenyl)-5-(2-methylthiopyrimidin-4-yl)-N-hydroxy-imidazole (E11.1)

An analogous reaction to that described in example E1.1, but starting with D11 gave E11.1 in 96% yield.
MS: M=465 (API+), 463 (API−)

Example E11.2

2-(2,6-dichloro-4-hydroxyphenyl)-4-(4-chlorophenyl)-5-(2-methylthiopyrimidin-4-yl)-N-hydroxy-imidazole (E11.2)

Example E11.3

2-(2,6-dichloro-4-hydroxymethylphenyl)-4-(4-chlorophenyl)-5-(2-methylthiopyrimidin-4-yl)-N-hydroxy-imidazole (E11.3)

Example E12.1

2-(2,6-dichlorophenyl)-4-(4-fluorophenyl)-5-(2-methylthiopyrimidin-4-yl)-N-hydroxy-imidazole (E12.1)

Example E12.2

2-(2,6-dichloro-4-hydroxyphenyl)-4-(4-fluorophenyl)-5-(2-methylthiopyrimidin-4-yl)-N-hydroxy-imidazole (E12.2)

Example E12.3

2-(2,6-dichloro-4-hydroxymethylphenyl)-4-(4-fluorophenyl)-5-(2-methylthiopyrimidin-4-yl)-N-hydroxy-imidazole (E12.3)

Example E13.1

2-(2,6-dichlorophenyl)-4-(4-chloro-3-methoxyphenyl)-5-(2-methylthiopyrimidin-4-yl)-N-hydroxy-imidazole (E13.1)

An analogous reaction to that described in example E1.1, but starting with D13 gave E13.1 in 88% yield.
MS: M=495 (API+), 493 (API−)

Example E13.2

2-(2,6-dichloro-4-hydroxyphenyl)-4-(4-chloro-3-methoxyphenyl)-5-(2-methylthiopyrimidin-4-yl)-N-hydroxy-imidazole (E13.2)

Example E13.3

2-(2,6-dichloro-4-hydroxymethylphenyl)-4-(4-chloro-3-methoxyphenyl)-5-(2-methylthiopyrimidin-4-yl)-N-hydroxy-imidazole (E13.3)

Example E14.1

2-(2,6-dichlorophenyl)-4-(3-benzyloxy-4-fluorophenyl)-5-(2-methylthiopyrimidin-4-yl)-N-hydroxy-imidazole (E14.1)

An analogous reaction to that described in example E1.1, but starting with D14 gave E14.1 in 93% yield.
MS: M=553 (API+), 551 (API−)

Example E14.2

2-(2,6-dichloro-4-hydroxyphenyl)-4-(3-benzyloxy-4-fluorophenyl)-5-(2-methylthiopyrimidin-4-yl)-N-hydroxy-imidazole (E14.2)

An analogous reaction to that described in example E1.1, but starting with D14 and A1 gave E14.2 in 95% yield.
MS: M=569 (API+), 567 (API−)

Example E14.3

2-(2,6-dichloro-4-hydroxymethylphenyl)-4-(3-benzyloxy-4-fluorophenyl)-5-(2-methylthiopyrimidin-4-yl)-N-hydroxy-imidazole (E14.3)

An analogous reaction to that described in example E1.1, but starting with D14 and A3 gave E14.3.
MS: M=583 (API+), 581 (API−)

Example E15.1

2-(2,6-dichlorophenyl)-4-(3-benzyloxy-4-methylphenyl)-5-(2-methylthiopyrimidin-4-yl)-N-hydroxy-imidazole (E15.1)

Example E15.2

2-(2,6-dichloro-4-hydroxyphenyl)-4-(3-benzyloxy-4-methylphenyl)-5-(2-methylthiopyrimidin-4-yl)-N-hydroxy-imidazole (E15.2)

An analogous reaction to that described in example E1.1, but starting with D15 and A1 gave E15.2 in 89% yield.
MS: M=565 (API+), 563(API−)

Example E15.3

2-(2,6-dichloro-4-hydroxymethylphenyl)-4-(3-benzyloxy-4-methylphenyl)-5-(2-methylthiopyrimidin-4-yl)-N-hydroxy-imidazole (E15.3)

An analogous reaction to that described in example E1.1, but starting with D15 and A3 gave E15.3 in 99% yield.
MS: M=579 (API+), 577 (API−)

Example E16.1

2-(2,6-dichlorophenyl)-4-(3-methylthiophenyl)-5-(2-methylthiopyrimidin-4-yl)-N-hydroxy-imidazole (E16.1)

An analogous reaction to that described in example E1.1, but starting with D16 gave E16.1 in 87% yield.
MS: M=475 (API+), 473 (API−)

Example E16.2

2-(2,6-dichloro-4-hydroxyphenyl)-4-(3-methylthiophenyl)-5-(2-methylthiopyrimidin-4-yl)-N-hydroxy-imidazole (E16.2)

Example E16.3

2-(2,6-dichloro-4-hydroxymethylphenyl)-4-(3-methylthiophenyl)-5-(2-methylthiopyrimidin-4-yl)-N-hydroxy-imidazole (E16.3)

Example E17.1

2-(2,6-dichlorophenyl)-4-(3-trimethylsilylacetylenylphenyl)-5-(2-methylthiopyrimidin-4-yl)-N-hydroxy-imidazole (E17.1)

An analogous reaction to that described in example E1.1, but starting with D17 gave E17.1 in 61% yield.
MS: M=525 (API+), 523 (API−)

Example E17.2

2-(2,6-dichloro-4-hydroxyphenyl)-4-(3-trimethylsilylacetylenylphenyl)-5-(2-methylthio-pyrimidin-4-yl)-N-hydroxy-imidazole (E17.2)

Example E17.3

2-(2,6-dichloro-4-hydroxymethylphenyl)-4-(3-trimethylsilylacetylenylphenyl)-5-(2-methylthiopyrimidin-4-yl)-N-hydroxy-imidazole (E17.3)

F Synthesis of the "2,6-dichlorophenyl-N-H imidazoles"

Example F1.1

2-(2,6-dichlorophenyl)-4-(3-bromophenyl)-5-(2-methylthiopyrimidin-4-yl)-N-H-imidazole (F1.1)

78.1 g (130 mmol) E1.1 , 59.8 g (391 mmol) methyl bromoacetate and 181.6 ml (1.3 mol) triethylamine were dissolved in 3.35 l methanol and stirred at 60° C. overnight. After removal of the solvent in vacuo the residue was partitionated between ethyl acetate/water. The organic layer was dried over sodium sulfate evaporated to dryness an the residue was treated with diisopropylether, filtered off and dried. Yield: 44.1 g (69%) F1, m.p. 183–186° C.

MS: M=493 (ESI+), M=491 (ESI−). $^1$H-NMR (250 MHz, D$_6$-DMSO):δ=2.18 (s, 3H, SCH$_3$), 7.43 (t, 1H, Ar—H), 7.5–7.8 (m, 5H, Ar—H), 7.87 (s, 1H, 2-H—BrPh), 8.56 (d, 1H, 6-H-pyrimidine), 13.4 (s, 1H, OH).

Example F1.2

2-(2,6-dichloro-4-hydroxyphenyl)-4-(3-bromophenyl)-5-(2-methylthiopyrimidin-4-yl)-N-H-imidazole (F1.2)

1.34 g (3.0 mmol) E1.2 and 6.71 ml (38.0 mmol) triethyl phosphite in 57 ml dry dimethylformamide were stirred at 100° C. for 2 h. After removal of all volatiles in vacuo, column chromatography of the residue on SiGel (dichloromethane/methanol 20:1) returned F1.2 in 70% yield.
MS: M=509 (API+), 507 (API−)

Example F1.3

2-(2,6-dichloro-4-hydroxymethylphenyl)-4-(3-bromophenyl)-5-(2-methylthiopyrimidin-4-yl)-N-H-imidazole (F1.3)

An analogous reaction to that described in example F1.1, but starting with E1.3 gave F1.3 in 74% yield.
MS: M=523 (API+), 521 (API−)

Example F1.4

2-(2,6-dichloro-4-(2-methoxy-ethoxymethoxy)phenyl)-4-(3-bromophenyl)-5-(2-methylthiopyrimidin-4-yl)-N-H-imidazole (F1.4)

An analogous reaction to that described in example F1.1, but starting with E1.4 gave F1.4 in 99% yield.
MS: M=597 (API+), 595 (API−)

Example F2.1

2-(2,6-dichlorophenyl)-4-(3-iodophenyl)-5-(2-methylthiopyrimidin-4-yl)-N-H-imidazole (F2.1)

An analogous reaction to that described in example F1.1, but starting with E2.1 gave F2.1 in 99% yield.
MS: M=539 (API+), 537 (API−)

Example F2.2

2-(2,6-dichloro-4-hydroxyphenyl)-4-(3-iodophenyl)-5-(2-methylthiopyrimidin-4-yl)-N-H-imidazole (F2.2)

An analogous reaction to that described in example F1.1, but starting with E2.2 gave F2.2 in 58% yield.
MS: M=555 (API+), 553 (API−)

Example F2.3

2-(2,6-dichloro-4-hydroxymethylphenyl)-4-(3-iodophenyl)-5-(2-methylthiopyrimidin-4-yl)-N-H-imidazole (F2.3)

An analogous reaction to that described in example F1.1, but starting with E2.3 gave F2.3 in 56% yield.
MS: M=569 (API+), 567 (API−)

Example F3.1

2-(2,6-dichlorophenyl)-4-(3-chlorophenyl)-5-(2-methylthiopyrimidin-4-yl)-N-H-imidazole (F3.1)

An analogous reaction to that described in example F1.1, but starting with E3.1 gave F3.1 in 64% yield.
MS: M=449 (API+), 447 (API−)

Example F3.2

2-(2,6-dichloro-4-hydroxyphenyl)-4-(3-chlorophenyl)-5-(2-methylthiopyrimidin-4-yl)-N-H-imidazole (F3.2)

Example F3.3

2-(2,6-dichloro-4-hydroxymethylphenyl)-4-(3-chlorophenyl)-5-(2-methylthiopyrimidin-4-yl)-N-H-imidazole (F3.3)

An analogous reaction to that described in example F1.1, but starting with E3.3 gave F3.3 in 98% yield.
MS: M=479 (API+), 477 (API−)

Example F4.1

2-(2,6-dichlorophenyl)-4-(3-benzyloxyphenyl)-5-(2-methylthiopyrimidin-4-yl)-N-H-imidazole (F4.1)

An analogous reaction to that described in example F1.2, but starting with E4.1 gave F4.1 in 76% yield.
MS: M=519 (API+), 517 (API−)

Example F4.2

2-(2,6-dichloro-4-hydroxyphenyl)-4-(3-benzyloxyphenyl)-5-(2-methylthiopyrimidin-4-yl)-N-H-imidazole (F4.2)

An analogous reaction to that described in example F1.1, but starting with E4.2 gave F4.2 in 42% yield. As a byproduct 34% F4.4 was obtained.
MS: M=535 (API+), 533 (API−)

Example F4.3

2-(2,6-dichloro-4-hydroxymethylphenyl)-4-(3-benzyloxyphenyl)-5-(2-methylthiopyrimidin-4-yl)-N-H-imidazole (F4.3)

An analogous reaction to that described in example F1.2, but starting with E4.3 gave F4.3 in 63% yield. MS: M=549 (API+), 547 (API−)

Example F4.4

2-(2,6-dichloro-4-[methoxycarbonylmethoxy]phenyl)-4-(3-benzyloxyphenyl)-5-(2-methylthio-pyrimidin-4-yl)-N-H-imidazole (F4.4)

An analogous reaction to that described in example F1.1, but starting with E4.4 gave F4.4 in 79% yield. Starting with E4.5 also returned F4.4 (trans-esterification in methanol) in 81% yield.
MS: M=607 (API+), 605 (API−)

Example F4.5

2-(2,6-dichloro-4-(2-hydroxyethoxy)phenyl)-4-(3-benzyloxyphenyl)-5-(2-methylthio-pyrimidin-4-yl)-N-H-imidazole (F4.5)

To a solution of 3.96 g (6.5 mmol) F4.4 in 70 ml dry THF 3.59 ml lithium alanate (1 M in toluene) was added at 0° C. The reaction was monitored by HPLC and stopped by adding a few drops of water. After removal of the solvent, the residue was purified by column chromatography on SiGel (ethyl acetate) to yield 3.40 g (90%) F4.5 as a light yellow oil, that solidifies on standing.
MS: M=579 (API+), 577 (API−)

Example F4.6

2-(2,6-dichloro-4-(2-carboxymethoxy)phenyl)-4-(3-benzyloxyphenyl)-5-(2-methylthio-pyrimidin-4-yl)-N-H-imidazole (F4.6)

To a solution of 676 mg (1.1 mmol) F4.4 in 20 ml methanol was added a solution of 125 mg (2.2 mmol) KOH in water. After stirring for 30 minutes, 100 µl glacial acid was added. The mixture was treated further without purification (example G4.6) assuming 100% yield.
MS: M=591 (ESI−).

Example F4.7

(rac)-2-(2,6-dichloro-4-(2,2-dimethyl-[1,3]-dioxolane-4-ylmethoxy)phenyl)-4-(3-benzyloxyphenyl)-5-(2-methylthiopyrimidin-4-yl)-N-H-imidazole (F4.7)

Example F4.7.1

(R)-2-(2,6-dichloro-4-(2,2-dimethyl-[1,3]-dioxolane-4-ylmethoxy)phenyl)-4-(3-benzyloxyphenyl)-5-(2-methylthiopyrimidin-4-yl)-N-H-imidazole (F4.7.1)

Example F4.7.2

(S)-2-(2,6-dichloro-4-(2,2-dimethyl-[1,3]-dioxolane-4-ylmethoxy)phenyl)-4-(3-benzyloxyphenyl)-5-(2-methylthiopyrimidin-4-yl)-N-H-imidazole (F4.7.2)

Example F4.8

(rac)-2-(2,6-dichloro-4-(2,3-dihydroxypropoxy)phenyl)-4-(3-benzyloxyphenyl)-5-(2-methylthio-pyrimidin-4-yl)-N-H-imidazole (F4.8)

Example F4.8.1

(R)-2-(2,6-dichloro-4-(2,3-dihydroxypropoxy)
phenyl)-4-(3-benzyloxyphenyl)-5-(2-methylthio-
pyrimidin-4-yl)-N-H-imidazole (F4.8.1)

An analogous reaction to that described in example F1.1, but starting with E4.7.1 gave F4.8.1 in 78% yield.
MS: M=609 (API+), 607 (API−)

Example F4.8.2

(S)-2-(2,6-dichloro-4-(2,3-dihydroxypropoxy)
phenyl)-4-(3-benzyloxyphenyl)-5-(2-methylthio-
pyrimidin-4-yl)-N-H-imidazole (F4.8.2)

An analogous reaction to that described in example F1.1, but starting with E4.7.2 gave F4.8.2 in 70% yield.
MS: M=609 (API+), 607 (API−)

Example F4.9

2-(2,6-dichloro-4-(dimethylphoshinoylmethoxy)
phenyl)-4-(3-benzyloxyphenyl)-5-(2-methylthio-
pyrimidin-4-yl)-N-H-imidazole (F4.9)

An analogous reaction to that described in example F1.1, but starting with E4.8 gave F4.9 in 72% yield.
MS: M=625 (API+), 623 (API−)

Example F4.10

2-(2,6-dichloro-4-methylthiophenyl)-4-(3-
benzyloxyphenyl)-5-(2-methylthiopyrimidin-4-yl)-
N-H-imidazole (F4.10)

Example F4.11

2-(2,6-dichloro-4-methanesulfinylphenyl)-4-(3-
benzyloxyphenyl)-5-(2-methylthio-pyrimidin-4-yl)-
N-H-imidazole (F4.11)

An analogous reaction to that described in example F1.1, but starting with E4.10 gave F4.11 in 98% yield.
MS: M=581 (API+), 579 (API−)

Example F4.12

2-(2,6-dichloro-4-methanesulfonylphenyl)-4-(3-
benzyloxyphenyl)-5-(2-methylthio-pyrimidin-4-yl)-
N-H-imidazole (F4.12)

Example F4.13

2-(2,6-dichloro-4-cyanomethyloxyphenyl)-4-(3-
benzyloxyphenyl)-5-(2-methylthio-pyrimidin-4-yl)-
N-H-imidazole (F4.13)

An analogous reaction to that described in example F1.1, but starting with E4.12 gave F4.13 in 72% yield.
MS: M=574 (API+), 572 (API−)

Example F4.14

2-(2,6-dichloro-4-(N-morpholino)methylphenyl)-4-
(3-benzyloxyphenyl)-5-(2-methylthiopyrimidin-4-
yl)-N-H-imidazole (F4.14)

Example F4.15

2-(2,6-dichloro-4-
ethoxycarbonylmethylthiomethylphenyl)-4-(3-
benzyloxyphenyl)-5-(2-methylthiopyrimidin-4-yl)-
N-H-imidazole (F4.15)

Example F4.16

2-(2,6-dichloro-4-hydroxyethylthiomethylphenyl)-4-
(3-benzyloxyphenyl)-5-(2-methylthiopyrimidin-4-
yl)-N-H-imidazole (F4.16)

Example F4.17

2-(2,6-dichloro-4-(N-morpholinoethylaminomethyl)
phenyl)-4-(3-benzyloxyphenyl)-5-(2-
methylthiopyrimidin-4-yl)-N-H-imidazole (F4.17)

Example F4.18

2-(2,6-dichloro-4-[2-(tert-butyldimethylsilanyloxy)-
1-(tert-butyldimethylsilanyloxymethyl)-ethoxy]-
phenyl)-4-(3-benzyloxyphenyl)-5-(2-
methylthiopyrimidin-4-yl)-N-H-imidazole (F4.18)

An analogous reaction to that described in example F1.1, but starting with E4.17 gave F4.18 in 27% yield.
MS: M=837 (API+)

Example F4.19

2-(2,6-dichloro-4-[3-(tert-butyldimethylsilanyloxy)-
2-(tert-butyldimethylsilanyloxymethyl)-propoxy]-
phenyl)-4-(3-benzyloxyphenyl)-5-(2-
methylthiopyrimidin-4-yl)-N-H-imidazole (F4.19)

Example F5.1

2-(2,6-dichlorophenyl)-4-(3-hydroxyphenyl)-5-(2-
methylthiopyrimidin-4-yl)-N-H-imidazole (F5.1)

Example F5.2

2-(2,6-dichloro-4-hydroxyphenyl)-4-(3-
hydroxyphenyl)-5-(2-methylthiopyrimidin-4-yl)-N-
H-imidazole (F5.2)

Example F5.3

2-(2,6-dichloro-4-hydroxymethylphenyl)-4-(3-
hydroxyphenyl)-5-(2-methylthiopyrimidin-4-yl)-N-
H-imidazole (F5.3)

An analogous reaction to that described in example F1.1, but starting with E5.3 gave F5.3 in 55% yield.
MS: M=459 (API+), 457 (API−)

Example F6.1

2-(2,6-dichlorophenyl)-4-(3-
methoxymethoxyphenyl)-5-(2-methylthiopyrimidin-
4-yl)-N-H-imidazole (F6.1)

An analogous reaction to that described in example F1.2, but starting with E6.1 gave F6.1 in 93% yield.
MS: M=473 (API+), 471 (API−)

Example F6.2

2-(2,6-dichloro-4-hydroxyphenyl)-4-(3-methoxymethoxyphenyl)-5-(2-methylthio-pyrimidin-4-yl)-N-H-imidazole (F6.2)

An analogous reaction to that described in example F1.1, but starting with E6.2 gave F6.2 in 58% yield.

MS: M=489 (API+), 487 (API−)

Example F6.3

2-(2,6-dichloro-4-hydroxymethylphenyl)-4-(3-methoxymethoxyphenyl)-5-(2-methylthiopyrimidin-4-yl)-N-H-imidazole (F6.3)

An analogous reaction to that described in example F1.1, but starting with E6.3 gave F6.3 in 44% yield.

MS: M=503 (API+), 501 (API−)

Example F6.4

2-(2,6-dichloro-4-[methoxycarbonylmethoxy]phenyl)-4-(3-methoxymethoxyphenyl)-5-(2-methylthio-pyrimidin-4-yl)-N-H-imidazole (F6.4)

An analogous reaction to that described in example F1.1, but starting with E6.5 gave F6.4 in 80% yield. (trans-esterification in methanol)

MS: M=561 (API+), 559 (API−)

Example F6.5

2-(2,6-dichloro-4-(2-hydroxyethoxy)phenyl)-4-(3-methoxymethoxyphenyl)-5-(2-methylthio-pyrimidin-4-yl)-N-H-imidazole (F6.5)

An analogous reaction to that described in example F4.5, but starting with F6.4 gave F6.5 in 70% yield.

MS: M=533 (API+), 531 (API−)

Example F6.6

2-(2,6-dichloro-4-(2-carboxymethoxy)phenyl)-4-(3-methoxymethoxyphenyl)-5-(2-methylthio-pyrimidin-4-yl)-N-H-imidazole (F6.6)

An analogous reaction to that described in example F4.6, but starting with F6.4 yielded F6.6. The crude product was used (example G6.6) without further purification assuming 100% yield.

MS: M=547 (API+), 545 (API−)

Example F6.7

(rac)-2-(2,6-dichloro-4-(2,2-dimethyl-[1,3]-dioxolane-4-ylmethoxy)phenyl)-4-(3-methoxymethoxyphenyl)-5-(2-methylthiopyrimidin-4-yl)-N-H-imidazole (F6.7)

Example F6.7.1

(R)-2-(2,6-dichloro-4-(2,2-dimethyl-[1,3]-dioxolane-4-ylmethoxy)phenyl)-4-(3-methoxymethoxyphenyl)-5-(2-methylthiopyrimidin-4-yl)-N-H-imidazole (F6.7.1)

Example F6.7.2

(S)-2-(2,6-dichloro-4-(2,2-dimethyl-[1,3]-dioxolane-4-ylmethoxy)phenyl)-4-(3-methoxymethoxyphenyl)-5-(2-methylthiopyrimidin-4-yl)-N-H-imidazole (F6.7.2)

Example F6.8

2-(2,6-dichloro-4-(2,3-dihydroxypropoxy)phenyl)-4-(3-methoxymethoxyphenyl)-5-(2-methylthio-pyrimidin-4-yl)-N-H-imidazole (F6.8)

Example F6.8.1

(R)-2-(2,6-dichloro-4-(2,3-dihydroxypropoxy)phenyl)-4-(3-methoxymethoxyphenyl)-5-(2-methylthio-pyrimidin-4-yl)-N-H-imidazole (F6.8.1)

Example F6.8.2

(S)-2-(2,6-dichloro-4-(2,3-dihydroxypropoxy)phenyl)-4-(3-methoxymethoxyphenyl)-5-(2-methylthio-pyrimidin-4-yl)-N-H-imidazole (F6.8.2)

Example F6.9

2-(2,6-dichloro-4-(dimethylphoshinoylmethoxy)phenyl)-4-(3-methoxymethoxyphenyl)-5-(2-methylthio-pyrimidin-4-yl)-N-H-imidazole (F6.9)

An analogous reaction to that described in example F1.1, but starting with E6.8 gave F6.9 in 62% yield.

MS: M=579 (API+), 577 (API−)

Example F6.10

2-(2,6-dichloro-4-methanesulfinylphenyl)-4-(3-methoxymethoxyphenyl)-5-(2-methylthio-pyrimidin-4-yl)-N-H-imidazole (F6.10)

An analogous reaction to that described in example F1.1, but starting with E6.9 gave F6.10 in 66% yield.

MS: M=535 (API+), 533 (API−)

Example F7.1

2-(2,6-dichlorophenyl)-4-(3-[4'-cyanobenzyloxy]phenyl)-5-(2-methylthiopyrimidin-4-yl)-N-H-imidazole (F7.1)

Example F7.2

2-(2,6-dichloro-4-hydroxyphenyl)-4-(3-[4'-cyanobenzyloxy]phenyl)-5-(2-methylthio-pyrimidin-4-yl)-N-H-imidazole (F7.2)

Example F7.3

2-(2,6-dichloro-4-hydroxymethylphenyl)-4-(3-[4'-cyanobenzyloxy]phenyl)-5-(2-methylthiopyrimidin-4-yl)-N-H-imidazole (F7.3)

Example F7.4

2-(2,6-dichloro-4-(2-hydroxyethoxy)phenyl)-4-(3-[4'-cyanobenzyloxy]phenyl)-5-(2-methylthiopyrimidin-4-yl)-N-H-imidazole (F7.4)

An analogous reaction to that described in example F1.1, but starting with E7.4 gave F7.4 in 62% yield.
MS: M=604 (API+), 602 (API−)

Example F8.1

2-(2,6-dichlorophenyl)-4-(3-[4'-chlorobenzyloxy]phenyl)-5-(2-methylthiopyrimidin-4-yl)-N-H-imidazole (F8.1)

An analogous reaction to that described in example F1.2, but starting with E8.1 gave F8.1 in 59% yield.
MS: M=555 (API+), 553 (API−)

Example F8.2

2-(2,6-dichloro-4-hydroxyphenyl)-4-(3-[4'-chlorobenzyloxy]phenyl)-5-(2-methylthiopyrimidin-4-yl)-N-H-imidazole (F8.2)

An analogous reaction to that described in example F1.2, but starting with E8.2 gave F8.2 in 63% yield.
MS: M=569 (API−)

Example F8.3

2-(2,6-dichloro-4-hydroxymethylphenyl)-4-(3-[4'-chlorobenzyloxy]phenyl)-5-(2-methylthiopyrimidin-4-yl)-N-H-imidazole (F8.3)

Example F9.1

2-(2,6-dichlorophenyl)-4-(3-[4'-methoxybenzyloxy]phenyl)-5-(2-methylthiopyrimidin-4-yl)-N-H-imidazole (F9.1)

Example F9.2

2-(2,6-dichloro-4-hydroxyphenyl)-4-(3-[4'-methoxybenzyloxy]phenyl)-5-(2-methylthio-pyrimidin-4-yl)-N-H-imidazole (F9.2)

Example F9.3

2-(2,6-dichloro-4-hydroxymethylphenyl)-4-(3-[4'-methoxybenzyloxy]phenyl)-5-(2-methylthiopyrimidin-4-yl)-N-H-imidazole (F9.3)

Example F10.1

2-(2,6-dichlorophenyl)-4-(3-allyloxyphenyl)-5-(2-methylthiopyrimidin-4-yl)-N-H-imidazole (F10.1)

An analogous reaction to that described in example F1.2, but starting with E10.1 gave F10.1 in 86% yield.
MS: M=469 (API+), 467 (API−)

Example F10.2

2-(2,6-dichloro-4-hydroxyphenyl)-4-(3-allyloxyphenyl)-5-(2-methylthiopyrimidin-4-yl)-N-H-imidazole (E10.2)

Example F10.3

2-(2,6-dichloro-4-hydroxymethylphenyl)-4-(3-allyloxyphenyl)-5-(2-methylthio-pyrimidin-4-yl)-N-H-imidazole (F10.3)

Example F11.1

2-(2,6-dichlorophenyl)-4-(4-chlorophenyl)-5-(2-methylthiopyrimidin-4-yl)-N-H-imidazole (F11.1)

An analogous reaction to that described in example F1.2, but starting with E11.1 gave F11.1 in 80% yield.
MS: M=449 (API+), 447 (API−)

Example F11.2

2-(2,6-dichloro-4-hydroxyphenyl)-4-(4-chlorophenyl)-5-(2-methylthiopyrimidin-4-yl)-N-H-imidazole (F11.2)

Example F11.3

2-(2,6-dichloro-4-hydroxymethylphenyl)-4-(4-chlorophenyl)-5-(2-methylthio-pyrimidin-4-yl)-N-H-imidazole (F11.3)

An analogous reaction to that described in example F1.1, but starting with E11.3 gave F11.3 in 33% yield.
MS: M=479 (API+), 477 (API−)

Example F12.1

2-(2,6-dichlorophenyl)-4-(4-fluorophenyl)-5-(2-methylthiopyrimidin-4-yl)-N-H-imidazole (F12.1)

Example F12.2

2-(2,6-dichloro-4-hydroxyphenyl)-4-(4-fluorophenyl)-5-(2-methylthio-pyrimidin-4-yl)-N-H-imidazole (F12.2)

Example F12.3

2-(2,6-dichloro-4-hydroxymethylphenyl)-4-(4-fluorophenyl)-5-(2-methylthiopyrimidin-4-yl)-N-H-imidazole (F12.3)

Example F13.1

2-(2,6-dichlorophenyl)-4-(4-chloro-3-methoxyphenyl)-5-(2-methylthiopyrimidin-4-yl)-N-H-imidazole (F13.1)

An analogous reaction to that described in example F1.2, but starting with E13.1 gave F13.1 in 81% yield.
MS: M=479 (API+), 477 (API−)

Example F13.2

2-(2,6-dichloro-4-hydroxyphenyl)-4-(4-chloro-3-methoxyphenyl)-5-(2-methylthio-pyrimidin-4-yl)-N-H-imidazole (F13.2)

Example F13.3

2-(2,6-dichloro-4-hydroxymethylphenyl)-4-(4-chloro-3-methoxyphenyl)-5-(2-methylthiopyrimidin-4-yl)-N-H-imidazole (F13.3)

Example F14.1

2-(2,6-dichlorophenyl)-4-(3-benzyloxy-4-fluorophenyl)-5-(2-methylthiopyrimidin-4-yl)-N-H-imidazole (F14.1)

An analogous reaction to that described in example F1.1, but starting with E14.1 gave F14.1 in 87% yield.
MS: M=537 (API+), 535 (API−)

Example F14.2

2-(2,6-dichloro-4-hydroxyphenyl)-4-(3-benzyloxy-4-fluorophenyl)-5-(2-methylthiopyrimidin-4-yl)-N-H-imidazole (F14.2)

An analogous reaction to that described in example F1.1, but starting with E14.2 gave F14.2 in 59% yield.
MS: M=553 (API+), 551 (API−)

Example F14.3

2-(2,6-dichloro-4-hydroxymethylphenyl)-4-(3-benzyloxy-4-fluorophenyl)-5-(2-methylthiopyrimidin-4-yl)-N-H-imidazole (F14.3)

An analogous reaction to that described in example F1.1, but starting with E14.3 gave F14.3 in 65% yield.
MS: M=567 (API+), 565 (API−)

Example F15.1

2-(2,6-dichlorophenyl)-4-(3-benzyloxy-4-methylphenyl)-5-(2-methylthiopyrimidin-4-yl)-N-H-imidazole (F15.1)

Example F15.2

2-(2,6-dichloro-4-hydroxyphenyl)-4-(3-benzyloxy-4-methylphenyl)-5-(2-methylthiopyrimidin-4-yl)-N-H-imidazole (F15.2)

An analogous reaction to that described in example F1.1, but starting with E15.2 gave F15.2 in 87% yield.
MS: M=549 (API+), 547 (API−)

Example F15.3

2-(2,6-dichloro-4-hydroxymethylphenyl)-4-(3-benzyloxy-4-methylphenyl)-5-(2-methylthiopyrimidin-4-yl)-N-H-imidazole (F15.3)

An analogous reaction to that described in example F1.1, but starting with E15.3 gave F15.3 in 83% yield.
MS: M=563 (API+), 561 (API−)

Example F16.1

2-(2,6-dichlorophenyl)-4-(3-methylthiophenyl)-5-(2-methylthiopyrimidin-4-yl)-N-H-imidazole (F16.1)

Example F16.2

2-(2,6-dichloro-4-hydroxyphenyl)-4-(3-methylthiophenyl)-5-(2-methylthiopyrimidin-4-yl)-N-H-imidazole (F16.2)

Example F16.3

2-(2,6-dichloro-4-hydroxymethylphenyl)-4-(3-methylthiophenyl)-5-(2-methylthio-pyrimidin-4-yl)-N-H-imidazole (F16.3)

Example F17.1

2-(2,6-dichlorophenyl)-4-(3-acetylenylphenyl)-5-(2-methylthiopyrimidin-4-yl)-N-H-imidazole (F17.1)

An analogous reaction to that described in example F1.1, but starting with E17.1 gave F17.1 in 99% yield.
MS: M=437 (API+), 435 (API−)

Example F17.2

2-(2,6-dichloro-4-hydroxyphenyl)-4-(3-acetylenylphenyl)-5-(2-methylthiopyrimidin-4-yl)-N-hydroxy-imidazole (F17.2)

Example F17.3

2-(2,6-dichloro-4-hydroxymethylphenyl)-4-(3-acetylenylphenyl)-5-(2-methylthio-pyrimidin-4-yl)-N-hydroxy-imidazole (F17.3)

G Synthesis of the "2,6-dichlorophenyl-N-H-imidazole sulfones" (and sulfoxides)

Example G1.1

2-(2,6-dichlorophenyl)-4-(3-bromophenyl)-5-(2-methanesulfonylpyrimidin-4-yl)-N-H-imidazole (G1.1)

A solution of 116.2 g (189 mmol) oxone™ in 1.7 l water was added to a solution of 44.3 g (90.0 mmol) F1.1 in 2.15 l methanol. After stirring 5 hours at room temperature, the methanol was distilled off and the residue taken up with ethyl acetate, washed with saturated aqueous sodium hydrogen carbonate, dried over sodium sulfate and evaporated to dryness. Chromatography of the residue on SiGel (n-heptane/ethyl acetate gradient 3:1 to 1:1) yielded 34.1 g (72%) G1.1, m.p. 231–233° C.

MS: M=525 (ESI+), M=523 (ESI−). $^1$H-NMR (250 MHz, CDCl$_3$): main tautomer (57%) δ=3.35 (s, 3H, CH$_3$), 7.3–7.7 (m, 6H, Ar—H), 7.84 (t, 1H, 2-H—Br—Ph), 8.64 (d, 1H, 6-H-pyrimidine), 11.2 (s, 1H, NH). $2^{nd}$ tautomer (43%)

δ=2.92 (s, 3H, CH₃), 7.3–7.7 (m, 5H, Ar—H), 7.74 (t, 1H, 2-H—Br—Ph), 8.23 (d, 1H, 5-H-pyrimidine), 8.81 (d, 1H, 6-H-pyrimidine), 10.4 (s, 1H, NH).

Example G1.2

2-(2,6-dichloro-4-hydroxyphenyl)-4-(3-bromophenyl)-5-(2-methanesulfonylpyrimidin-4-yl)-N-H-imidazole (G1.2)

An analogous reaction to that described in example G1.1, but starting with F1.2 gave G1.2 in 70% yield.
MS: M=541 (API+), 539 (API−)

Example G1.3

2-(2,6-dichloro-4-hydroxymethylphenyl)-4-(3-bromophenyl)-5-(2-methanesulfonyl-pyrimidin-4-yl)-N-H-imidazole (G1.3)

An analogous reaction to that described in example G1.1, but starting with F1.3 gave G1.3 in 7% yield.
MS: M=555 (API+), 553 (API−)

Example G1.4

2-(2,6-dichloro-4-(2-methoxy-ethoxymethoxy)phenyl)-4-(3-bromophenyl)-5-(2-methanesulfonylpyrimidin-4-yl)-N-H-imidazole (G1.4)

An analogous reaction to that described in example G1.1, but starting with F1.4 gave G1.4 in 86% yield.
MS: M=629 (API+), 627 (API−)

Example G2.1

2-(2,6-dichlorophenyl)-4-(3-iodophenyl)-5-(2-methanesulfonylpyrimidin-4-yl)-N-H-imidazole (G2.1)

An analogous reaction to that described in example G1.1, but starting with F2.1 gave G2.1 in 4% yield.
MS: M=571 (API+), 569 (API−)

Example G2.2

2-(2,6-dichloro-4-hydroxyphenyl)-4-(3-iodophenyl)-5-(2-methanesulfonylpyrimidin-4-yl)-N-H-imidazole (G2.2)

An analogous reaction to that described in example G1.1, but starting with F2.2 gave G2.2 in 40% yield.
MS: M=587 (API+), 585 (API−)

Example G2.3

2-(2,6-dichloro-4-hydroxymethylphenyl)-4-(3-iodophenyl)-5-(2-methanesulfonyl-pyrimidin-4-yl)-N-H-imidazole (G2.3)

An analogous reaction to that described in example G1.1, but starting with F2.3 gave G2.3 in 88% yield.
MS: M=601 (API+), 599 (API−)

Example G3.1

2-(2,6-dichlorophenyl)-4-(3-chlorophenyl)-5-(2-methanesulfonylpyrimidin-4-yl)-N-H-imidazole (G3.1)

An analogous reaction to that described in example G1.1, but starting with F3.1 gave G3.1 in 89% yield.
MS: M=481 (API+), 479 (API−)

Example G3.2

2-(2,6-dichloro-4-hydroxyphenyl)-4-(3-chlorophenyl)-5-(2-methanesulfonylpyrimidin-4-yl)-N-H-imidazole (G3.2)

Example G3.3

2-(2,6-dichloro-4-hydroxymethylphenyl)-4-(3-chlorophenyl)-5-(2-methanesulfonyl-pyrimidin-4-yl)-N-H-imidazole (G3.3)

An analogous reaction to that described in example G1.1, but starting with F3.3 gave G3.3 in 62% yield.
MS: M=511 (API+), 509 (API−)

Example G4.1

2-(2,6-dichlorophenyl)-4-(3-benzyloxyphenyl)-5-(2-methanesulfonylpyrimidin-4-yl)-N-H-imidazole (G4.1)

An analogous reaction to that described in example G1.1, but starting with F4.1 gave G4.1 in 73% yield.
MS: M=551 (API+), 549 (API−)

Example G4.2

2-(2,6-dichloro-4-hydroxyphenyl)-4-(3-benzyloxyphenyl)-5-(2-methanesulfonyl-pyrimidin-4-yl)-N-H-imidazole (G4.2)

An analogous reaction to that described in example G1.1, but starting with F4.2 gave G4.2 in 91% yield.
MS: M=567 (API+), 565 (API−)

Example G4.3

2-(2,6-dichloro-4-hydroxymethylphenyl)-4-(3-benzyloxyphenyl)-5-(2-methanesulfonyl-pyrimidin-4-yl)-N-H-imidazole (G4.3)

An analogous reaction to that described in example G1.1, but starting with F4.3 gave G4.3 in 24% yield.
MS: M=581 (API+), 579 (API−)

Example G4.4

2-(2,6-dichloro-4-[methoxycarbonylmethoxy]phenyl)-4-(3-benzyloxyphenyl)-5-(2-methanesulfonyl-pyrimidin-4-yl)-N-H-imidazole (G4.4)

Example G4.5

2-(2,6-dichloro-4-(2-hydroxyethoxy)phenyl)-4-(3-benzyloxyphenyl)-5-(2-methane-sulfonylpyrimidin-4-yl)-N-H-imidazole (G4.5)

An analogous reaction to that described in example G1.1, but starting with F4.5 gave G4.5 in 94% yield.

MS: M=611 (API+), 609 (API−)

Example G4.6

2-(2,6-dichloro-4-(2-carboxymethoxy)phenyl)-4-(3-benzyloxyphenyl)-5-(2-methane-sulfonylpyrimidin-4-yl)-N-H-imidazole (G4.6)

An analogous reaction to that described in example G1.1, but starting with F4.6 gave G4.6 in 79% yield.

MS: M=625 (API+), 623 (API−)

Example G4.7

(rac)-2-(2,6-dichloro-4-(2,2-dimethyl-[1,3]-dioxolane-4-ylmethoxy)phenyl)-4-(3-benzyloxyphenyl)-5-(2-methanesulfonylpyrimidin-4-yl)-N-H-imidazole (G4.7)

Example G4.7.1

(R)-2-(2,6-dichloro-4-(2,2-dimethyl-[1,3]-dioxolane-4-ylmethoxy)phenyl)-4-(3-benzyloxyphenyl)-5-(2-methanesulfonylpyrimidin-4-yl)-N-H-imidazole (G4.7.1)

Example G4.7.2

(S)-2-(2,6-dichloro-4-(2,2-dimethyl-[1,3]-dioxolane-4-ylmethoxy)phenyl)-4-(3-benzyloxyphenyl)-5-(2-methanesulfonylpyrimidin-4-yl)-N-H-imidazole (G4.7.2)

Example G4.8

2-(2,6-dichloro-4-(2,3-dihydroxypropoxy)phenyl)-4-(3-benzyloxyphenyl)-5-(2-methanesulfonyl-pyrimidin-4-yl)-N-H-imidazole (G4.8)

Example G4.8.1

(R)-2-(2,6-dichloro-4-(2,3-dihydroxypropoxy)phenyl)-4-(3-benzyloxyphenyl)-5-(2-methanesulfonyl-pyrimidin-4-yl)-N-H-imidazole (G4.8.1)

An analogous reaction to that described in example G1.1, but starting with F4.8.1 gave G4.8.1 in 99% yield.

MS: M=641 (API+), 639 (API−)

Example G4.8.2

(S)-2-(2,6-dichloro-4-(2,3-dihydroxypropoxy)phenyl)-4-(3-benzyloxyphenyl)-5-(2-methanesulfonyl-pyrimidin-4-yl)-N-H-imidazole (G4.8.2)

An analogous reaction to that described in example G1.1, but starting with F4.8.2 gave G4.8.2 in 90% yield.

MS: M=641 (API+), 639 (API−)

Example G4.9

2-(2,6-dichloro-4-(dimethylphoshinoylmethoxy)phenyl)-4-(3-benzyloxyphenyl)-5-(2-methanesulfonyl-pyrimidin-4-yl)-N-H-imidazole (G4.9)

An analogous reaction to that described in example G1.1, but starting with F4.9 gave G4.9 in 91% yield.

MS: M=657 (API+), 655 (API−)

Example G4.10

2-(2,6-dichloro-4-methylthiophenyl)-4-(3-benzyloxyphenyl)-5-(2-methanesulfinyl-pyrimidin-4-yl)-N-H-imidazole (G4.10)

Example G4.11

2-(2,6-dichloro-4-methanesulfinylphenyl)-4-(3-benzyloxyphenyl)-5-(2-methanesulfinylpyrimidin-4-yl)-N-H-imidazole (G4.11)

216 mg (0.7 mmol) MCPBA were added to a −40° C. solution of 400 mg (0.7 mmol) F4.11 in 6 ml dichloromethane/ethyl acetate (1:1). After 2 hours at −40° C. the mixture was allowed to warm up to room temperature. The solution was washed with water/ethyl acetate, dried over sodium sulphate and evaporated. Column chromatography of the residue returned 180 mg (44%) G4.11.

MS: M=597 (API+), 595 (API−)

Example G4.12

2-(2,6-dichloro-4-methanesulfonylphenyl)-4-(3-benzyloxyphenyl)-5-(2-methanesulfonyl-pyrimidin-4-yl)-N-H-imidazole (G4.12)

Example G4.13

2-(2,6-dichloro-4-cyanomethyloxyphenyl)-4-(3-benzyloxyphenyl)-5-(2-methanesulfonylpyrimidin-4-yl)-N-H-imidazole (G4.13)

An analogous reaction to that described in example G1.1, but starting with F4.13 gave G4.13 in 79% yield.

MS: M=606 (API+), 604 (API−)

Example G4.14

2-(2,6-dichloro-4-(N-morpholino)methylphenyl)-4-(3-benzyloxyphenyl)-5-(2-methylthiopyrimidin-4-yl)-N-H-imidazole (G4.14)

Example G4.15

2-(2,6-dichloro-4-ethoxycarbonylmethylthiomethylphenyl)-4-(3-benzyloxyphenyl)-5-(2-methanesulfonyl-pyrimidin-4-yl)-N-H-imidazole (G4.15)

Example G4.16

2-(2,6-dichloro-4-hydroxyethylthiomethylphenyl)-4-(3-benzyloxyphenyl)-5-(2-methylthiopyrimidin-4-yl)-N-H-imidazole (G4.16)

Example G4.17

2-(2,6-dichloro-4-(N-morpholinoethylaminomethyl)phenyl)-4-(3-benzyloxyphenyl)-5-(2-methanesulfonylpyrimidin-4-yl)-N-H-imidazole (G4.17)

Example G4.18

2-(2,6-dichloro-4-(2-hydroxy-1-hydroxymethyl-ethoxy]-phenyl)-4-(3-benzyloxyphenyl)-5-(2-methanesulfonylpyrimidin-4-yl)-N-H-imidazole (G4.18)

An analogous reaction to that described in example G1.1, but starting with F4.18 gave G4.18 in 82% yield.
MS: M=641 (API+)

Example G4.19

2-(2,6-dichloro-4-[3-(tert-butyldimethylsilanyloxy)-2-(tert-butyldimethylsilanyloxy-methyl)-propoxy]-phenyl)-4-(3-benzyloxyphenyl)-5-(2-methanesulfonylpyrimidin-4-yl)-N-H-imidazole (G4.19)

Example G5.1

2-(2,6-dichlorophenyl)-4-(3-hydroxyphenyl)-5-(2-methanesulfonylpyrimidin-4-yl)-N-H-imidazole (G5.1)

Example G5.2

2-(2,6-dichloro-4-hydroxyphenyl)-4-(3-hydroxyphenyl)-5-(2-methanesulfonylpyrimidin-4-yl)-N-H-imidazole (G5.2)

Example G5.3

2-(2,6-dichloro-4-hydroxymethylphenyl)-4-(3-hydroxyphenyl)-5-(2-methanesulfonyl-pyrimidin-4-yl)-N-H-imidazole (G5.3)

An analogous reaction to that described in example G1.1, but starting with F5.3 gave G5.3 in 81% yield.
MS: M=491 (API+), 489 (API−)

Example G6.1

2-(2,6-dichlorophenyl)-4-(3-methoxymethoxyphenyl)-5-(2-methanesulfonylpyrimidin-4-yl)-N-H-imidazole (G6.1)

An analogous reaction to that described in example G1.1, but starting with F6.1 gave G6.1 in 80% yield.
MS: M=505 (API+), 503 (API−)

Example G6.2

2-(2,6-dichloro-4-hydroxyphenyl)-4-(3-methoxymethoxyphenyl)-5-(2-methanesulfonyl-pyrimidin-4-yl)-N-H-imidazole (G6.2)

An analogous reaction to that described in example G1.1, but starting with F6.2 gave G6.2 in 53% yield.
MS: M=521 (API+), 519 (API−)

Example G6.3

2-(2,6-dichloro-4-hydroxymethylphenyl)-4-(3-methoxymethoxyphenyl)-5-(2-methanesulfonylpyrimidin-4-yl)-N-H-imidazole (G6.3)

An analogous reaction to that described in example G1.1, but starting with F6.3 gave G6.3 in 58% yield.
MS: M=535 (API+), 533 (API−)

Example G6.4

2-(2,6-dichloro-4-[methoxycarbonylmethoxy]phenyl)-4-(3-methoxymethoxyphenyl)-5-(2-methanesulfonylpyrimidin-4-yl)-N-H-imidazole (G6.4)

Example G6.5

2-(2,6-dichloro-4-(2-hydroxyethoxy)phenyl)-4-(3-methoxymethoxyphenyl)-5-(2-methanesulfonyl-pyrimidin-4-yl)-N-H-imidazole (G6.5)

An analogous reaction to that described in example G1.1, but starting with F6.5 gave G6.5 in 85% yield.
MS: M=565 (API+), 563 (API−)

Example G6.6

2-(2,6-dichloro-4-(2-carboxymethoxy)phenyl)-4-(3-methoxymethoxyphenyl)-5-(2-methanesulfonyl-pyrimidin-4-yl)-N-H-imidazole (G6.6)

An analogous reaction to that described in example G1.1, but starting with F6.6 gave G6.6 in 58% yield.
MS: M=579 (API+), 577 (API−)

Example G6.7

(rac)-2-(2,6-dichloro-4-(2,2-dimethyl-[1,3]-dioxolane-4-ylmethoxy)phenyl)-4-(3-methoxymethoxyphenyl)-5-(2-methanesulfonylpyrimidin-4-yl)-N-H-imidazole (G6.7)

Example G6.7.1

(R)-2-(2,6-dichloro-4-(2,2-dimethyl-[1,3]-dioxolane-4-ylmethoxy)phenyl)-4-(3-methoxymethoxyphenyl)-5-(2-methanesulfonylpyrimidin-4-yl)-N-H-imidazole (G6.7.1)

Example G6.7.2

(S)-2-(2,6-dichloro-4-(2,2-dimethyl-[1,3]-dioxolane-
4-ylmethoxy)phenyl)-4-(3-methoxy-
methoxyphenyl)-5-(2-methanesulfonylpyrimidin-4-
yl)-N-H-imidazole (G6.7.2)

Example G6.8

(rac)-2-(2,6-dichloro-4-(2,3-dihydroxypropoxy)
phenyl)-4-(3-methoxy-methoxyphenyl)-5-(2-
methanesulfonyl-pyrimidin-4-yl)-N-H-imidazole
(G6.8)

Example G6.8.1

(R)-2-(2,6-dichloro-4-(2,3-dihydroxypropoxy)
phenyl)-4-(3-methoxymethoxyphenyl)-5-(2-
methanesulfonyl-pyrimidin-4-yl)-N-H-imidazole
(G6.8.1)

Example G6.8.2

(S)-2-(2,6-dichloro-4-(2,3-dihydroxypropoxy)
phenyl)-4-(3-methoxy-methoxyphenyl)-5-(2-
methanesulfonyl-pyrimidin-4-yl)-N-H-imidazole
(G6.8.2)

Example G6.9

2-(2,6-dichloro-4-(dimethylphoshinoylmethoxy)
phenyl)-4-(3-methoxymethoxyphenyl)-5-(2-
methanesulfonylpyrimidin-4-yl)-N-H-imidazole
(G6.9)

An analogous reaction to that described in example G1.1,
but starting with F6.9 gave G6.9 in 77% yield.
MS: M=611 (API+), 609 (API−)

Example G6.10

2-(2,6-dichloro-4-methanesulfinylphenyl)-4-(3-
methoxymethoxyphenyl)-5-(2-
methanesulfinylpyrimidin-4-yl)-N-H-imidazole
(G6.10)

An analogous reaction to that described in example
G4.11, but starting with F6.10 gave G6.10 in 56% yield.
MS: M=551 (API+), 549 (API−)

Example G7.1

2-(2,6-dichlorophenyl)-4-(3-[4'-cyanobenzyloxy]
phenyl)-5-(2-methanesulfonylpyrimidin-4-yl)-N-H-
imidazole (G7.1)

Example G7.2

2-(2,6-dichloro-4-hydroxyphenyl)-4-(3-[4'-
cyanobenzyloxy]phenyl)-5-(2-methane-
sulfonylpyrimidin-4-yl)-N-H-imidazole (G7.2)

Example G7.3

2-(2,6-dichloro-4-hydroxymethylphenyl)-4-(3-[4'-
cyanobenzyloxy]phenyl)-5-(2-methanesulfonyl-
pyrimidin-4-yl)-N-H-imidazole (G7.3)

Example G7.4

2-(2,6-dichloro-4-(2-hydroxyethoxy)phenyl)-4-(3-
[4'-cyanobenzyloxy]phenyl)-5-(2-
methanesulfonylpyrimidin-4-yl)-N-H-imidazole
(G7.4)

An analogous reaction to that described in example G1.1,
but starting with F7.4 gave G7.4 in 81% yield.
MS: M=636 (API+), 634 (API−)

Example G8.1

2-(2,6-dichlorophenyl)-4-(3-[4'-chlorobenzyloxy]
phenyl)-5-(2-methanesulfonyl-pyrimidin-4-yl)-N-H-
imidazole (G8.1)

An analogous reaction to that described in example G1.1,
but starting with F8.1 gave G8.1 in 47% yield.
MS: M=587 (API+), 585 (API−)

Example G8.2

2-(2,6-dichloro-4-hydroxyphenyl)-4-(3-[4'-
chlorobenzyloxy]phenyl)-5-(2-
methanesulfonylpyrimidin-4-yl)-N-H-imidazole
(G8.2)

An analogous reaction to that described in example G1.1,
but starting with F8.2 gave G8.2 in 68% yield.
MS: M=603 (API+), 601 (API−)

Example G8.3

2-(2,6-dichloro-4-hydroxymethylphenyl)-4-(3-[4'-
chlorobenzyloxy]phenyl)-5-(2-methanesulfonyl-
pyrimidin-4-yl)-N-H-imidazole (G8.3)

Example G9.1

2-(2,6-dichlorophenyl)-4-(3-[4'-methoxybenzyloxy]
phenyl)-5-(2-methanesulfonyl-pyrimidin-4-yl)-N-H-
imidazole (G9.1)

Example G9.2

2-(2,6-dichloro-4-hydroxyphenyl)-4-(3-[4'-
methoxybenzyloxy]phenyl)-5-(2-
methanesulfonylpyrimidin-4-yl)-N-H-imidazole
(G9.2)

Example G9.3

2-(2,6-dichloro-4-hydroxymethylphenyl)-4-(3-[4'-
methoxybenzyloxy]phenyl)-5-(2-
methanesulfonylpyrimidin-4-yl)-N-H-imidazole
(G9.3)

Example G10.1

2-(2,6-dichlorophenyl)-4-(3-allyloxyphenyl)-5-(2-methanesulfonylpyrimidin-4-yl)-N-H-imidazole (G10.1)

An analogous reaction to that described in example G1.1, but starting with F10.1 gave G10.1 in 75% yield.
MS: M=501 (API+), 499 (API−)

Example G10.2

2-(2,6-dichloro-4-hydroxyphenyl)-4-(3-allyloxyphenyl)-5-(2-methanesulfonylpyrimidin-4-yl)-N-H-imidazole (G10.2)

Example G10.3

2-(2,6-dichloro-4-hydroxymethylphenyl)-4-(3-allyloxyphenyl)-5-(2-methanesulfonyl-pyrimidin-4-yl)-N-H-imidazole (G10.3)

Example G11.1

2-(2,6-dichlorophenyl)-4-(4-chlorophenyl)-5-(2-methanesulfonylpyrimidin-4-yl)-N-H-imidazole (G11.1)

An analogous reaction to that described in example G1.1, but starting with F11.1 gave G11.1 in 87% yield.
MS: M=481 (API+), 479 (API−)

Example G11.2

2-(2,6-dichloro-4-hydroxyphenyl)-4-(4-chlorophenyl)-5-(2-methanesulfonylpyrimidin-4-yl)-N-H-imidazole (G11.2)

Example G11.3

2-(2,6-dichloro-4-hydroxymethylphenyl)-4-(4-chlorophenyl)-5-(2-methanesulfonyl-pyrimidin-4-yl)-N-H-imidazole (G11.3)

An analogous reaction to that described in example G11.1, but starting with F11.3 gave G11.3 in 99% yield.
MS: M=511 (API+), 509 (API−)

Example G12.1

2-(2,6-dichlorophenyl)-4-(4-fluorophenyl)-5-(2-methanesulfonylpyrimidin-4-yl)-N-H-imidazole (G12.1)

Example G12.2

2-(2,6-dichloro-4-hydroxyphenyl)-4-(4-fluorophenyl)-5-(2-methanesulfonylpyrimidin-4-yl)-N-H-imidazole (G12.2)

Example G12.3

2-(2,6-dichloro-4-hydroxymethylphenyl)-4-(4-fluorophenyl)-5-(2-methanesulfonyl-pyrimidin-4-yl)-N-H-imidazole (G12.3)

Example G13.1

2-(2,6-dichlorophenyl)-4-(4-chloro-3-methoxyphenyl)-5-(2-methanesulfonylpyrimidin-4-yl)-N-H-imidazole (G13.1)

An analogous reaction to that described in example G1.1, but starting with F13.1 gave G13.1 in 53% yield.
MS: M=509.01 (API+), 507 (API−)

Example G13.2

2-(2,6-dichloro-4-hydroxyphenyl)-4-(4-chloro-3-methoxyphenyl)-5-(2-methanesulfonyl-pyrimidin-4-yl)-N-H-imidazole (G13.2)

Example G13.3

2-(2,6-dichloro-4-hydroxymethylphenyl)-4-(4-chloro-3-methoxyphenyl)-5-(2-methane-sulfonylpyrimidin-4-yl)-N-H-imidazole (G13.3)

Example G14.1

2-(2,6-dichlorophenyl)-4-(3-benzyloxy-4-fluorophenyl)-5-(2-methanesulfonylpyrimidin-4-yl)-N-H-imidazole (G14.1)

An analogous reaction to that described in example G1.1, but starting with F14.1 gave G14.1 in 61% yield.
MS: M=569 (API+), 567 (API−)

Example G14.2

2-(2,6-dichloro-4-hydroxyphenyl)-4-(3-benzyloxy-4-fluorophenyl)-5-(2-methanesulfonylpyrimidin-4-yl)-N-H-imidazole (G14.2)

An analogous reaction to that described in example G1.1, but starting with F14.2 gave G14.2 in 84% yield.
MS: M=585 (API+), 583 (API−)

Example G14.3

2-(2,6-dichloro-4-hydroxymethylphenyl)-4-(3-benzyloxy-4-fluorophenyl)-5-(2-methanesulfonyl-pyrimidin-4-yl)-N-H-imidazole (G14.3)

An analogous reaction to that described in example G1.1, but starting with F14.3 gave G14.3 in 80% yield.
MS: M=599 (API+), 597 (API−)

Example G15.1

2-(2,6-dichlorophenyl)-4-(3-benzyloxy-4-methylphenyl)-5-(2-methanesulfonylpyrimidin-4-yl)-N-H-imidazole (G15.1)

Example G15.2

2-(2,6-dichloro-4-hydroxyphenyl)-4-(3-benzyloxy-4-methylphenyl)-5-(2-methanesulfonylpyrimidin-4-yl)-N-H-imidazole (G15.2)

An analogous reaction to that described in example G1.1, but starting with F15.2 gave G15.2 in 40% yield.
MS: M=581 (API+), 579 (API−)

Example G15.3

2-(2,6-dichloro-4-hydroxymethylphenyl)-4-(3-benzyloxy-4-methylphenyl)-5-(2-methanesulfonyl-pyrimidin-4-yl)-N-H-imidazole (G15.3)

An analogous reaction to that described in example G1.1, but starting with F15.3 gave G15.3 in 61% yield.

MS: M=595 (API+), 593 (API−)

Example G16.1

2-(2,6-dichlorophenyl)-4-(3-methylthiophenyl)-5-(2-methanesulfinylpyrimidin-4-yl)-N-H-imidazole (G16.1)

2-(2,6-dichlorophenyl)-4-(3-methylthiophenyl)-5-(2-methanesulfinylpyrimidin-4-yl)-N-hydroxy-imidazole (G16.1.1)

To a solution of 480 mg (1 mmol) E16.1 in 3 ml dichloromethane a solution of 246 mg (1 mmol) 3-chloroperbenzoic acid in 7 ml dichloromethane was added at 0° C. and stirred at this temperature for 6 hours. After washing with 5% aqueous sodium hydrogencarbonate and water (each 0° C.) the organic layer was dried over sodium sulfate and evaporated to dryness to yield 470 mg G16.1.1 (96%).

MS: 475 (API+), 473 (API−)

Example G16.2

2-(2,6-dichloro-4-hydroxyphenyl)-4-(3-methylthiophenyl)-5-(2-methanesulfinyl-pyrimidin-4-yl)-N-H-imidazole (G16.1)

Example G16.3

2-(2,6-dichloro-4-hydroxymethylphenyl)-4-(3-methylthiophenyl)-5-(2-methanesulfinyl-pyrimidin-4-yl)-N-H-imidazole (G16.1)

Example G17.1

2-(2,6-dichlorophenyl)-4-(3-acetylenylphenyl)-5-(2-methanesulfonylpyrimidin-4-yl)-N-H-imidazole (G17.1)

An analogous reaction to that described in example G1.1, but starting with F17.1 gave G17.1 in 98% yield.

MS: M=469 (API+)

Example G17.2

2-(2,6-dichloro-4-hydroxyphenyl)-4-(3-acetylenylphenyl)-5-(2-methanesulfonyl-pyrimidin-4-yl)-N-H-imidazole (G17.1)

Example G17.3

2-(2,6-dichloro-4-hydroxymethylphenyl)-4-(3-acetylenylphenyl)-5-(2-methanesulfonyl-pyrimidin-4-yl)-N-H-imidazole (G17.1)

H Synthesis of the "2,6-dichlorophenyl-N-H-imidazole aminopyrimidines"

Example H1.1.1

2-(2,6-dichlorophenyl)-4-(3-bromophenyl)-5-(2-[3-hydroxypropylamino]pyrimidin-4-yl)-N-H-imidazole (H1.1.1)

52.4 mg (0.10 mmol) G1.1 and 120.2 mg (1.60 mmol) 3-amino-1-propanol were heated to 110° C. for 60 minutes. Purification by preparative scale HPLC/MS on RP 18 (methanol-water-gradient) yielded 35.5 mg (68%) H1.1.1.

MS: M=520 (API+)

Example H1.1.2

2-(2,6-dichlorophenyl)-4-(3-bromophenyl)-5-(2-[2-hydroxyethylamino]pyrimidin-4-yl)-N-H-imidazole (H1.1.2)

An analogous reaction to that described in example H1.1.1, but starting with 2-aminoethanol gave H1.1.2 in 43% yield.

MS: M=506 (API+)

Example H1.1.3

2-(2,6-dichlorophenyl)-4-(3-bromophenyl)-5-(2-[3-methoxypropylamino]pyrimidin-4-yl)-N-H-imidazole (H1.1.3)

An analogous reaction to that described in example H1.1.1, but starting with 3-methoxy-1-aminopropane gave H1.1.3 in 83% yield.

MS: M=534 (API+)

Example H1.1.4

2-(2,6-dichlorophenyl)-4-(3-bromophenyl)-5-(2-[2-methoxyethylamino]pyrimidin-4-yl)-N-H-imidazole (H1.1.4)

An analogous reaction to that described in example H1.1.1, but starting with 2-methoxy-1-aminoethane gave H1.1.4 in 69% yield.

MS: M=520 (API+)

Example H1.1.5

(rac)-2-(2,6-dichlorophenyl)-4-(3-bromophenyl)-5-(2-[2,3-dihydroxypropylamino]-pyrimidin-4-yl)-N-H-imidazole (H1.1.5)

An analogous reaction to that described in example H1.1.1, but starting with (rac)-2,3-dihydroxypropylamine gave H1.1.5 in 74% yield.

MS: M=536 (API+)

Example H1.1.6

(R)-2-(2,6-dichlorophenyl)-4-(3-bromophenyl)-5-(2-[2,3-dihydroxypropylamino]-pyrimidin-4-yl)-N-H-imidazole (H1.1.6)

An analogous reaction to that described in example H1.1.1, but starting with (R)-2,3-dihydroxypropylamine gave H1.1.6 in 84% yield.

MS: M=536 (API+)

Example H1.1.7

(S)-2-(2,6-dichlorophenyl)-4-(3-bromophenyl)-5-(2-[2,3-dihydroxypropylamino]-pyrimidin-4-yl)-N-H-imidazole (H1.1.7)

An analogous reaction to that described in example H1.1.1, but starting with (S)-2,3-dihydroxypropylamine gave H1.1.7 in 71% yield.

MS: M=536 (API+)

Example H1.1.8

2-(2,6-dichlorophenyl)-4-(3-bromophenyl)-5-(2-[2-N-morpholinoethyl]pyrimidin-4-yl)-N-H-imidazole (H1.1.7)

An analogous reaction to that described in example H1.1.1, but starting with N-(2-aminoethyl)morpholine gave H1.1.8 in 85% yield, m.p. 104–108° C.

MS: M=575 (ESI+), M=573 (ESI−). $^1$H-NMR (250 MHz, CDCl$_3$) δ=2.4–2.7 (m, 6 H, CH$_2$N), 3.61 (q, 2H, CH$_2$NH), 3.70 (t, 4H, OCH$_2$), 5.67 (br, 1H, NH), 6.67 (d, 1H, 5-H-pyrimidine), 7.2–7.6 (m, 4H, Ar—H), 7.64 (d, 1H, Ar—H), 7.90 (t, 1H, 2-H-bromophenyl), 8.17 (d, 1H, 6-H-pyrimidine), 10.6 (br, 1H, NH).

Example H1.1.9

2-(2,6-dichlorophenyl)-4-(3-bromophenyl)-5-(2-[3-N-morpholinopropyl]pyrimidin-4-yl)-N-H-imidazole (H1.1.8)

An analogous reaction to that described in example H1.1.1, but starting with N-(3-aminopropyl)morpholine gave H1.1.9 in 89% yield, m.p. 102–105° C.

MS: M=589 (ESI+), M=587 (ESI−). $^1$H-NMR (250 MHz, CDCl$_3$): δ=1.79 (quintett, 2H, C—CH$_2$—C), 2.4–2.6 (m, 6H, CH$_2$N), 3.51 (q, 2H, CH$_2$NH), 3.72 (t, 4H, OCH$_2$), 5.77 (br, 1H, NH), 6.73 (d, 1H, 5-H-pyrimidine), 7.2–7.6 (m, 4H, Ar—H), 7.66 (d, 1H, Ar—H), 7.88 (t, 1H, 2-H-bromophenyl), 8.13 (d, 1H, 6-H-pyrimidine), 10.5 (br, 1H, NH).

Example H1.1.10

2-(2,6-dichlorophenyl)-4-(3-bromophenyl)-5-(2-(3-[N-methylpiperazin-1-yl]propylamino)pyrimidin-4-yl)-N-H-imidazole (H1.1.10)

An analogous reaction to that described in example H1.1.1, but starting with 1-(3-aminopropyl)-4-methylpiperazine gave H1.1.10 in 73% yield, m.p. 113–116° C.

MS: M=602 (ESI+), M=600 (ESI−). $^1$H-NMR (250 MHz, CDCl$_3$): δ=1.79 (quintett, 2H, C—CH$_2$—C), 2.24 (NCH$_3$), 2.3–2.7 (m, 10H, CH$_2$N), 3.49 (q, 2H, CH$_2$NH), 5.92 (br, 1H, NH), 6.74 (d, 1H, 5-H-pyrimidine), 7.2–7.6 (m, 4H, Ar—H), 7.66 (d, 1H, Ar—H), 7.89 (t, 1H, 2-H-bromophenyl), 8.14 (d, 1H, 6-H-pyrimidine), 10.4 (br, 1H, NH).

Example H1.1.11

2-(2,6-dichlorophenyl)-4-(3-bromophenyl)-5-(2-[3-tert-butoxycarbonylpropylamino]-pyrimidin-4-yl)-N-H-imidazole (H1.1.11)

An analogous reaction to that described in example H1.1.1, but starting with tert-butyl 4-aminobutyrate gave H1.1.11 in 25% yield.

MS: M=604 (API+)

Example H1.1.12

2-(2,6-dichlorophenyl)-4-(3-bromophenyl)-5-(2-[3-carboxypropylamino]pyrimidin-4-yl)-N-H-imidazole (H1.1.12)

1 ml of a solution of 1.96 g KOH in 2.5 ml water and 5 ml ethanol was added to 50 mg (80 μmol) H1.1.11, and the mixture was heated to 110° C. for 4 h. The alcohol was removed and the precipitate was solved in water and concentated HCl was added until pH 1 was reached. After extraction with dichloromethane the organic layer was evaporated to dryness and the residue was purified preparative scale HPLC/MS on RP 18 (methanol-water-gradient) and 20.5 mg (47%) H1.1.12 were returned.

MS: M=548 (API+)

Example H1.2.1

2-(2,6-dichloro-4-hydroxyphenyl)-4-(3-bromophenyl)-5-(2-[3-hydroxypropylamino]-pyrimidin-4-yl)-N-H-imidazole (H1.2.1)

An analogous reaction to that described in example H1.1.1, but starting with G1.2 gave H1.2.1 in 76% yield.

MS: M=536 (API+)

Example H1.2.2

2-(2,6-dichloro-4-hydroxyphenyl)-4-(3-bromophenyl)-5-(2-[2-hydroxyethylamino]-pyrimidin-4-yl)-N-H-imidazole (H1.2.2)

An analogous reaction to that described in example H1.1.1, but starting with G1.2 and 2-aminoethanol gave H1.2.2 in 78% yield.

MS: M=522 (API+)

Example H1.2.3

2-(2,6-dichloro-4-hydroxyphenyl)-4-(3-bromophenyl)-5-(2-[3-methoxypropylamino]-pyrimidin-4-yl)-N-H-imidazole (H1.2.3)

An analogous reaction to that described in example H1.1.1, but starting with G1.2 and 3-methoxy-1-aminopropane gave H1.2.3 in 84% yield.

MS: M=550 (API+)

Example H1.2.4

2-(2,6-dichloro-4-hydroxyphenyl)-4-(3-bromophenyl)-5-(2-[2-methoxyethylamino]-pyrimidin-4-yl)-N-H-imidazole (H1.2.4)

An analogous reaction to that described in example H1.1.1, but starting with G1.2 and 2-methoxy-1-aminoethane gave H1.2.4 in 75% yield.

MS: M=536 (API+)

Example H1.2.5

(rac)-2-(2,6-dichloro-4-hydroxyphenyl)-4-(3-bromophenyl)-5-(2-[2,3-dihydroxypropylamino]pyrimidin-4-yl)-N-H-imidazole (H1.2.5)

An analogous reaction to that described in example H1.1.1, but starting with G1.2 and (rac)-2,3-dihydroxypropylamine gave H1.2.5 in 66% yield.

MS: M=552 (API+)

Example H1.3.1

2-(2,6-dichloro-4-hydroxymethylphenyl)-4-(3-bromophenyl)-5-(2-[3-hydroxypropylamino]pyrimidin-4-yl)-N-H-imidazole (H1.3.1)

An analogous reaction to that described in example H1.1.1, but starting with G1.3 gave H1.3.1 in 58% yield.
MS: M=550 (API+)

Example H1.3.2

2-(2,6-dichloro-4-hydroxymethylphenyl)-4-(3-bromophenyl)-5-(2-[2-hydroxyethylamino]pyrimidin-4-yl)-N-H-imidazole (H1.3.2)

An analogous reaction to that described in example H1.1.1, but starting with G1.3 and 2-aminoethanol gave H1.3.2 in 60% yield.
MS: M=536 (API+)

Example H1.3.3

2-(2,6-dichloro-4-hydroxymethylphenyl)-4-(3-bromophenyl)-5-(2-[3-methoxypropylamino]pyrimidin-4-yl)-N-H-imidazole (H1.3.3)

An analogous reaction to that described in example H1.1.1, but starting with G1.3 and 3-methoxy-1-aminopropane gave H1.3.3 in 55% yield.
MS: M=564 (API+)

Example H1.3.4

2-(2,6-dichloro-4-hydroxymethylphenyl)-4-(3-bromophenyl)-5-(2-[2-methoxy-ethylamino]pyrimidin-4-yl)-N-H-imidazole (H1.3.4)

An analogous reaction to that described in example H1.1.1, but starting with G1.3 and 2-methoxy-1-aminoethane gave H1.3.4 in 55% yield.
MS: M=550 (API+)

Example H1.3.5

2-(2,6-dichloro-4-hydroxymethylphenyl)-4-(3-bromophenyl)-5-(2-[2,3-dihydroxypropylamino]-pyrimidin-4-yl)-N-H-imidazole (H1.3.5)

Example H1.4.1

2-(2,6-dichloro-4-(2-methoxy-ethoxymethoxy)methylphenyl)-4-(3-bromophenyl)-5-(2-[3-hydroxypropyl-amino]pyrimidin-4-yl)-N-H-imidazole (H1.4.1)

An analogous reaction to that described in example H1.1.1, but starting with G1.4 gave H1.4.1 in 62% yield.
MS: M=622 (API+)

Example H1.4.2

2-(2,6-dichloro-4-(2-methoxy-ethoxymethoxy)methylphenyl)-4-(3-bromophenyl)-5-(2-[2-hydroxyethyl-amino]pyrimidin-4-yl)-N-H-imidazole (H1.4.2)

An analogous reaction to that described in example H1.1.1, but starting with G1.4 and 2-aminoethanol gave H1.4.2 in 18% yield.
MS: M=608 (API+)

Example H1.4.3

2-(2,6-dichloro-4-(2-methoxy-ethoxymethoxy)methylphenyl)-4-(3-bromophenyl)-5-(2-[3-methoxy-propylamino]pyrimidin-4-yl)-N-H-imidazole (H1.4.3)

An analogous reaction to that described in example H1.1.1, but starting with G1.4 and 3-methoxy-1-aminopropane gave H1.4.3 in 13% yield.
MS: M=636 (API+)

Example H1.4.4

2-(2,6-dichloro-4-(2-methoxy-ethoxymethoxy)methylphenyl)-4-(3-bromophenyl)-5-(2-[2-methoxy-ethylamino]pyrimidin-4-yl)-N-H-imidazole (H1.4.4)

An analogous reaction to that described in example H1.1.1, but starting with G1.4 and 2-methoxy-1-aminoethane gave H1.4.4 in 4% yield.
MS: M=622 (API+)

Example H1.4.5

2-(2,6-dichloro-4-(2-methoxy-ethoxymethoxy)phenyl)-4-(3-bromophenyl)-5-(2-[2,3-dihydroxypropyl-amino]pyrimidin-4-yl)-N-H-imidazole (H1.4.5)

An analogous reaction to that described in example H1.1.1, but starting with G1.4 and (rac)-2,3-dihydroxypropylamine gave H1.4.5 in 25% yield.
MS: M=638 (API+)

Example H2.1.1

2-(2,6-dichlorophenyl)-4-(3-iodophenyl)-5-(2-[3-hydroxypropylamino]pyrimidin-4-yl)-N-H-imidazole (H2.1.1)

An analogous reaction to that described in example H1.1.1, but starting with G2.1 gave H2.1.1 in 52% yield.
MS: M=566 (API+)

Example H2.1.2

2-(2,6-dichlorophenyl)-4-(3-iodophenyl)-5-(2-[2-hydroxyethylamino]pyrimidin-4-yl)-N-H-imidazole (H2.1.2)

An analogous reaction to that described in example H1.1.1, but starting with G2.1 and 2-aminoethanol gave H2.1.2 in 59% yield.
MS: M=552 (API+)

Example H2.1.3

2-(2,6-dichlorophenyl)-4-(3-iodophenyl)-5-(2-[3-methoxypropylamino]pyrimidin-4-yl)-N-H-imidazole (H2.1.3)

Example H2.1.4

2-(2,6-dichlorophenyl)-4-(3-iodophenyl)-5-(2-[2-methoxyethylamino]pyrimidin-4-yl)-N-H-imidazole (H2.1.4)

Example H2.1.5

2-(2,6-dichlorophenyl)-4-(3-iodophenyl)-5-(2-[2,3-dihydroxypropylamino]pyrimidin-4-yl)-N-H-imidazole (H2.1.5)

An analogous reaction to that described in example H1.1.1, but starting with G2.1 and 2,3-dihydroxypropylamine gave H2.1.5 in 58% yield.
MS: M=582 (API+)

Example H2.2.1

2-(2,6-dichloro-4-hydroxyphenyl)-4-(3-iodophenyl)-5-(2-[3-hydroxypropylamino]-pyrimidin-4-yl)-N-H-imidazole (H2.2.1)

An analogous reaction to that described in example H1.1.1, but starting with G2.2 gave H2.2.1 in 49% yield.
MS: M=582 (API+)

Example H2.2.2

2-(2,6-dichloro-4-hydroxyphenyl)-4-(3-iodophenyl)-5-(2-[2-hydroxyethylamino]-pyrimidin-4-yl)-N-H-imidazole (H2.2.2)

An analogous reaction to that described in example H1.1.1, but starting with G2.2 and 2-aminoethanol gave H2.2.2 in 49% yield.
MS: M=568 (API+)

Example H2.2.3

2-(2,6-dichloro-4-hydroxyphenyl)-4-(3-iodophenyl)-5-(2-[3-methoxypropylamino]-pyrimidin-4-yl)-N-H-imidazole (H2.2.3)

An analogous reaction to that described in example H1.1.1, but starting with G2.2 and 3-methoxy-1-aminopropane gave H2.2.3 in 61% yield.
MS: M=596 (API+)

Example H2.2.4

2-(2,6-dichloro-4-hydroxyphenyl)-4-(3-iodophenyl)-5-(2-[2-methoxyethylamino]-pyrimidin-4-yl)-N-H-imidazole (H2.2.4)

An analogous reaction to that described in example H1.1.1, but starting with G2.2 and 2-methoxy-1-aminoethane gave H2.2.4 in 52% yield.
MS: M=582 (API+)

Example H2.2.5

2-(2,6-dichloro-4-hydroxyphenyl)-4-(3-iodophenyl)-5-(2-[2,3-dihydroxypropylamino]-pyrimidin-4-yl)-N-H-imidazole (H2.2.5)

An analogous reaction to that described in example H1.1.1, but starting with G2.2 and 2,3-dihydroxypropylamine gave H2.2.5 in 39% yield.
MS: M=598 (API+)

Example H2.3.1

2-(2,6-dichloro-4-hydroxymethylphenyl)-4-(3-iodophenyl)-5-(2-[3-hydroxypropylamino]pyrimidin-4-yl)-N-H-imidazole (H2.3.1)

An analogous reaction to that described in example H1.1.1, but starting with G2.3 gave H2.3.1 in 34% yield.
MS: M=596 (API+)

Example H2.3.2

2-(2,6-dichloro-4-hydroxyphenyl)-4-(3-iodophenyl)-5-(2-[2-hydroxyethylamino]-pyrimidin-4-yl)-N-H-imidazole (H2.3.2)

An analogous reaction to that described in example H1.1.1, but starting with G2.3 and 2-aminoethanol gave H2.3.2 in 36% yield.
MS: M=582 (API+)

Example H2.3.3

2-(2,6-dichloro-4-hydroxyphenyl)-4-(3-iodophenyl)-5-(2-[3-methoxypropylamino]-pyrimidin-4-yl)-N-H-imidazole (H2.3.3)

An analogous reaction to that described in example H1.1.1, but starting with G2.3 and 3-methoxy-1-aminopropane gave H2.3.3 in 35% yield.
MS: M=610 (API+)

Example H2.3.4

2-(2,6-dichloro-4-hydroxyphenyl)-4-(3-iodophenyl)-5-(2-[2-methoxyethylamino]-pyrimidin-4-yl)-N-H-imidazole (H2.3.4)

An analogous reaction to that described in example H1.1.1, but starting with G2.3 and 2-methoxy-1-aminoethane gave H2.3.4 in 20% yield.
MS: M=596 (API+)

Example H2.3.5

2-(2,6-dichloro-4-hydroxyphenyl)-4-(3-iodophenyl)-5-(2-[2,3-dihydroxypropylamino]-pyrimidin-4-yl)-N-H-imidazole (H2.3.5)

An analogous reaction to that described in example H1.1.1, but starting with G2.3 and 2,3-dihydroxypropylamine gave H2.3.5 in 27% yield.
MS: M=612 (API+)

Example H3.1.1

2-(2,6-dichlorophenyl)-4-(3-chlorophenyl)-5-(2-[3-hydroxypropylamino]pyrimidin-4-yl)-N-H-imidazole (H3.1.1)

Example H3.1.2

2-(2,6-dichlorophenyl)-4-(3-chlorophenyl)-5-(2-[2-hydroxyethylamino]-pyrimidin-4-yl)-N-H-imidazole (H3.1.2)

Example H3.1.3

2-(2,6-dichlorophenyl)-4-(3-chlorophenyl)-5-(2-[3-methoxypropylamino]-pyrimidin-4-yl)-N-H-imidazole (H3.1.3)

Example H3.1.4

2-(2,6-dichlorophenyl)-4-(3-chlorophenyl)-5-(2-[2-methoxyethylamino]-pyrimidin-4-yl)-N-H-imidazole (H3.1.4)

Example H3.1.5

(rac)-2-(2,6-dichlorophenyl)-4-(3-chlorophenyl)-5-(2-[2,3-dihydroxypropylamino]pyrimidin-4-yl)-N-H-imidazole (H3.1.5)

Example H3.1.6

(R)-2-(2,6-dichlorophenyl)-4-(3-chlorophenyl)-5-(2-[2,3-dihydroxypropylamino]-pyrimidin-4-yl)-N-H-imidazole (H3.1.6)

An analogous reaction to that described in example H1.1.1, but starting with G3.1 and (R)-2,3-dihydroxypropylamine gave H3.1.6 in 25% yield.
MS: M=492 (API+)

Example H3.1.7

(S)-2-(2,6-dichlorophenyl)-4-(3-bromophenyl)-5-(2-[2,3-dihydroxypropylamino]-pyrimidin-4-yl)-N-H-imidazole (H3.1.7)

An analogous reaction to that described in example H1.1.1, but starting with G3.1 and (R)-2,3-dihydroxypropylamine gave H3.1.7 in 35% yield.
MS: M=492 (API+)

Example H3.2.1

2-(2,6-dichloro-4-hydroxyphenyl)-4-(3-chlorophenyl)-5-(2-[3-hydroxypropylamino]pyrimidin-4-yl)-N-H-imidazole (H3.2.1)

Example H3.2.2

2-(2,6-dichloro-4-hydroxyphenyl)-4-(3-chlorophenyl)-5-(2-[2-hydroxyethylamino]pyrimidin-4-yl)-N-H-imidazole (H3.2.2)

Example H3.2.3

2-(2,6-dichloro-4-hydroxyphenyl)-4-(3-chlorophenyl)-5-(2-[3-methoxypropylamino]pyrimidin-4-yl)-N-H-imidazole (H3.2.3)

Example H4.1.1

2-(2,6-dichlorophenyl)-4-(3-benzyloxyphenyl)-5-(2-[3-hydroxypropylamino]pyrimidin-4-yl)-N-H-imidazole (H4.1.1)

An analogous reaction to that described in example H1.1.1, but starting with G4.1 gave H4.1.1 in 72% yield.
MS: M=546 (API+)

Example H3.2.4

2-(2,6-dichloro-4-hydroxyphenyl)-4-(3-chlorophenyl)-5-(2-[2-methoxyethylamino]pyrimidin-4-yl)-N-H-imidazole (H3.2.4)

Example H3.2.5

(rac)-2-(2,6-dichloro-4-hydroxyphenyl)-4-(3-chlorophenyl)-5-(2-[2,3-dihydroxypropyl-amino]pyrimidin-4-yl)-N-H-imidazole (H3.2.5)

Example H3.3.1

2-(2,6-dichloro-4-hydroxymethylphenyl)-4-(3-chlorophenyl)-5-(2-[3-hydroxypropylamino]pyrimidin-4-yl)-N-H-imidazole (H3.3.1)

Example H3.3.2

2-(2,6-dichloro-4-hydroxymethylphenyl)-4-(3-chlorophenyl)-5-(2-[2-hydroxyethylamino]pyrimidin-4-yl)-N-H-imidazole (H3.3.2)

Example H3.3.3

2-(2,6-dichloro-4-hydroxymethylphenyl)-4-(3-chlorophenyl)-5-(2-[3-methoxypropylamino]pyrimidin-4-yl)-N-H-imidazole (H3.3.3)

Example H3.3.4

2-(2,6-dichloro-4-hydroxymethylphenyl)-4-(3-chlorophenyl)-5-(2-[2-methoxyethylamino]pyrimidin-4-yl)-N-H-imidazole (H3.3.4)

Example H3.3.5

(rac)-2-(2,6-dichloro-4-hydroxymethylphenyl)-4-(3-chlorophenyl)-5-(2-[2,3-dihydroxypropyl-amino]pyrimidin-4-yl)-N-H-imidazole (H3.1.5)

Example H3.3.6

(R)-2-(2,6-dichloro-4-hydroxymethylphenyl)-4-(3-chlorophenyl)-5-(2-[2,3-dihydroxypropyl-amino]pyrimidin-4-yl)-N-H-imidazole (H3.3.6)

An analogous reaction to that described in example H1.1.1, but starting with G3.1 and (R)-2,3-dihydroxypropylamine gave H3.1.6 in 55% yield.
MS: M=522 (API+)

Example H3.3.7

(S)-2-(2,6-dichloro-4-hydroxymethylphenyl)-4-(3-bromophenyl)-5-(2-[2,3-dihydroxypropylamino]-pyrimidin-4-yl)-N-H-imidazole (H3.3.7)

An analogous reaction to that described in example H1.1.1, but starting with G3.3 and (R)-2,3-dihydroxypropylamine gave H3.3.7 in 40% yield.
MS: M=522 (API+)

Example H4.1.2

2-(2,6-dichlorophenyl)-4-(3-benzyloxyphenyl)-5-(2-[2-hydroxyethylamino]pyrimidin-4-yl)-N-H-imidazole (H4.1.2)

An analogous reaction to that described in example H1.1.1, but starting with G4.1 and 2-aminoethanol gave H4.1.2 in 64% yield.

MS: M=532 (API+)

Example H4.1.3

2-(2,6-dichlorophenyl)-4-(3-benzyloxyphenyl)-5-(2-[3-methoxypropylamino]pyrimidin-4-yl)-N-H-imidazole (H4.1.3)

An analogous reaction to that described in example H1.1.1, but starting with G4.1 and 3-methoxy-1-aminopropane gave H4.1.3 in 98% yield.

MS: M=560 (API+)

Example H4.1.4

2-(2,6-dichlorophenyl)-4-(3-benzyloxyphenyl)-5-(2-[2-methoxyethylamino]pyrimidin-4-yl)-N-H-imidazole (H4.1.4)

An analogous reaction to that described in example H1.1.1, but starting with G4.1 and 2-methoxy-1-aminoethane gave H4.1.4 in 83% yield.

MS: M=546 (API+)

Example H4.1.5

(rac)-2-(2,6-dichlorophenyl)-4-(3-benzyloxyphenyl)-5-(2-[3-hydroxybutylamino]pyrimidin-4-yl)-N-H-imidazole (H4.1.5)

An analogous reaction to that described in example H1.1.1, but starting with G4.1 and (rac)-4-amino-2-butanol gave H4.1.5 in 24% yield.

MS: M=560 (API+)

Example H4.1.6

(rac)-2-(2,6-dichlorophenyl)-4-(3-benzyloxyphenyl)-5-(2-[2,3-dihydroxypropylamino]pyrimidin-4-yl)-N-H-imidazole (H4.1.6)

An analogous reaction to that described in example H1.1.1, but starting with G4.1 and (rac)-2,3-dihydroxypropylamine gave H4.1.6 in 62% yield.

MS: M=562 (API+)

Example H4.1.7

2-(2,6-dichlorophenyl)-4-(3-benzyloxyphenyl)-5-(2-[2-(2-dimethylaminoethyl)-thioethylamino]-pyrimidin-4-yl)-N-H-imidazole (H4.1.7)

An analogous reaction to that described in example H1.1.1, but starting with G4.1 and 2-(2-dimethylaminoethyl)thioethylamine gave H4.1.7 in 69% yield.

MS: M=619 (API+), 617 (API−)

Example H4.1.8

2-(2,6-dichlorophenyl)-4-(3-benzyloxyphenyl)-5-(2-[2-(3-dimethylaminopropyl)-thioethylamino]-pyrimidin-4-yl)-N-H-imidazole (H4.1.8)

An analogous reaction to that described in example H1.1.1, but starting with G4.1 and 2-(3-dimethylaminopropyl)thioethylamine gave H4.1.8 in 63% yield.

MS: M=633 (API+), 631 (API−)

Example H4.1.9

2-(2,6-dichlorophenyl)-4-(3-benzyloxyphenyl)-5-(2-[3-(2-dimethylaminoethyl)-thiopropylamino]-pyrimidin-4-yl)-N-H-imidazole (H4.1.9)

An analogous reaction to that described in example H1.1.1, but starting with G4.1 and 3-(2-dimethylaminoethyl)thiopropylamine gave H4.1.9 in 41% yield.

MS: M=633 (API+), 631 (API−)

Example H4.1.10

2-(2,6-dichlorophenyl)-4-(3-benzyloxyphenyl)-5-(2-[3-(3-dimethylaminopropyl)thiopropylamino]-pyrimidin-4-yl)-N-H-imidazole (H4.1.10)

An analogous reaction to that described in example H1.1.1, but starting with G4.1 and 3-(3-dimethylaminopropyl)thiopropylamine gave H4.1.10 in 74% yield.

MS: M=647 (API+), 645 (API−)

Example H4.2.1

2-(2,6-dichloro-4-hydroxyphenyl)-4-(3-benzyloxyphenyl)-5-(2-[3-hydroxypropylamino]-pyrimidin-4-yl)-N-H-imidazole (H4.2.1)

An analogous reaction to that described in example H1.1.1, but starting with G4.2 gave H4.2.1 in 51% yield.

MS: M=562 (API+)

Example H4.2.2

2-(2,6-dichloro-4-hydroxyphenyl)-4-(3-benzyloxyphenyl)-5-(2-[2-hydroxyethylamino]-pyrimidin-4-yl)-N-H-imidazole (H4.2.2)

An analogous reaction to that described in example H1.1.1, but starting with G4.2 and 2-aminoethanol gave H4.2.2 in 50% yield.

MS: M=548 (API+)

Example H4.2.3

2-(2,6-dichloro-4-hydroxyphenyl)-4-(3-benzyloxyphenyl)-5-(2-[3-methoxypropylamino]pyrimidin-4-yl)-N-H-imidazole (H4.2.3)

An analogous reaction to that described in example H1.1.1, but starting with G4.2 and 3-methoxy-1-aminopropane gave H4.2.3 in 53% yield.

MS: M=576 (API+)

Example H4.2.4

2-(2,6-dichloro-4-hydroxyphenyl)-4-(3-benzyloxyphenyl)-5-(2-[2-methoxyethylamino]pyrimidin-4-yl)-N-H-imidazole (H4.2.4)

An analogous reaction to that described in example H1.1.1, but starting with G4.2 and 2-methoxy-1-aminoethane gave H4.2.4 in 54% yield.
MS: M=562 (API+)

Example H4.2.5

(rac)-2-(2,6-dichloro-4-hydroxyphenyl)-4-(3-benzyloxyphenyl)-5-(2-[2,3-dihydroxypropyl-amino]pyrimidin-4-yl)-N-H-imidazole (H4.2.5)

An analogous reaction to that described in example H1.1.1, but starting with G4.2 and (rac)-2,3-dihydroxypropylamine gave H4.2.5 in 40% yield.
MS: M=578 (API+)

Example H4.3.1

2-(2,6-dichloro-4-hydroxymethylphenyl)-4-(3-benzyloxyphenyl)-5-(2-[3-hydroxypropylamino]pyrimidin-4-yl)-N-H-imidazole (H4.3.1)

An analogous reaction to that described in example H1.1.1, but starting with G4.3 gave H4.3.1 in 70% yield.
MS: M=576 (API+)

Example H4.3.2

2-(2,6-dichloro-4-hydroxymethylphenyl)-4-(3-benzyloxyphenyl)-5-(2-[2-hydroxyethylamino]pyrimidin-4-yl)-N-H-imidazole (H4.3.2)

An analogous reaction to that described in example H1.1.1, but starting with G4.3 and 2-aminoethanol gave H4.3.2 in 57% yield.
MS: M=562 (API+)

Example H4.3.3

2-(2,6-dichloro-4-hydroxymethylphenyl)-4-(3-benzyloxyphenyl)-5-(2-[3-methoxypropylamino]pyrimidin-4-yl)-N-H-imidazole (H4.3.3)

An analogous reaction to that described in example H1.1.1, but starting with G4.3 and 3-methoxy-1-aminopropane gave H4.3.3 in 76% yield.
MS: M=590 (ESI+).

Example H4.3.4

2-(2,6-dichloro-4-hydroxymethylphenyl)-4-(3-benzyloxyphenyl)-5-(2-[2-methoxyethylamino]pyrimidin-4-yl)-N-H-imidazole (H4.3.4)

An analogous reaction to that described in example H1.1.1, but starting with G4.3 and 2-methoxy-1-aminoethane gave H4.3.4 in 75% yield.
MS: M=576 (ESI+).

Example H4.3.5

(rac)-2-(2,6-dichloro-4-hydroxymethylphenyl)-4-(3-benzyloxyphenyl)-5-(2-[2,3-dihydroxypropyl-amino]pyrimidin-4-yl)-N-H-imidazole (H4.3.5)

An analogous reaction to that described in example H1.1.1, but starting with G4.3 and (rac)-2,3-dihydroxypropylamine gave H4.3.5 in 50% yield.
MS: M=592 (API+)

Example H4.4.1

2-(2,6-dichloro-4-[methoxycarbonylmethoxy]phenyl)-4-(3-benzyloxyphenyl)-5-(2-[3-hydroxypropyl-amino]pyrimidin-4-yl)-N-H-imidazole (H4.4.1)

Example H4.4.2

2-(2,6-dichloro-4-[methoxycarbonylmethoxy]phenyl)-4-(3-benzyloxyphenyl)-5-(2-[2-hydroxyethyl-amino]pyrimidin-4-yl)-N-H-imidazole (H4.4.2)

Example H4.4.3

2-(2,6-dichloro-4-[methoxycarbonylmethoxy]phenyl)-4-(3-benzyloxyphenyl)-5-(2-[3-methoxypropyl-amino]pyrimidin-4-yl)-N-H-imidazole (H4.4.3)

Example H4.4.4

2-(2,6-dichloro-4-[methoxycarbonylmethoxy]phenyl)-4-(3-benzyloxyphenyl)-5-(2-[2-methoxyethyl-amino]pyrimidin-4-yl)-N-H-imidazole (H4.4.4)

Example H4.4.5

2-(2,6-dichloro-4-[methoxycarbonylmethoxy]phenyl)-4-(3-benzyloxyphenyl)-5-(2-[2,3-dihydroxypropyl-amino]pyrimidin-4-yl)-N-H-imidazole (H4.4.5)

Example H4.5.1

2-(2,6-dichloro-4-(2-hydroxyethoxy)phenyl)-4-(3-benzyloxyphenyl)-5-(2-[3-hydroxypropyl-amino]pyrimidin-4-yl)-N-H-imidazole (H4.5.1)

An analogous reaction to that described in example H1.1, but starting with G4.5 gave H4.5.1 in 68% yield.
MS: M=606 (API+), 604 (API−)

Example H4.5.2

2-(2,6-dichloro-4-(2-hydroxyethoxy)phenyl)-4-(3-benzyloxyphenyl)-5-(2-[2-hydroxyethyl-amino]pyrimidin-4-yl)-N-H-imidazole (H4.5.2)

An analogous reaction to that described in example H1.1.1, but starting with G4.5 and 2-aminoethanol gave H4.5.2 in 72% yield.
MS: M=592 (API+), 590 (API−)

Example H4.5.3

2-(2,6-dichloro-4-(2-hydroxyethoxy)phenyl)-4-(3-benzyloxyphenyl)-5-(2-[3-methoxypropyl-amino]pyrimidin-4-yl)-N-H-imidazole (H4.5.3)

Example H4.5.4

2-(2,6-dichloro-4-(2-hydroxyethoxy)phenyl)-4-(3-benzyloxyphenyl)-5-(2-[2-methoxyethyl-amino]pyrimidin-4-yl)-N-H-imidazole (H4.5.4)

Example H4.5.5

(rac)-2-(2,6-dichloro-4-(2-hydroxyethoxy)phenyl)-4-(3-benzyloxyphenyl)-5-(2-[2,3-dihydroxypropyl-amino]pyrimidin-4-yl)-N-H-imidazole (H4.5.5)

An analogous reaction to that described in example H1.1.1, but starting with G4.5 and (rac)-2,3-dihydroxypropyl-amine gave H4.5.5 in 35% yield.
MS: M=622 (API+)

Example H4.6.1

2-(2,6-dichloro-4-(2-carboxymethoxy)phenyl)-4-(3-benzyloxyphenyl)-5-(2-[3-hydroxypropyl-amino]pyrimidin-4-yl)-N-H-imidazole (H4.6.1)

An analogous reaction to that described in example H1.1, but starting with G4.6 gave H4.6.1 in 31% yield.
MS: M=620 (API+)

Example H4.6.2

2-(2,6-dichloro-4-(2-carboxymethoxy)phenyl)-4-(3-benzyloxyphenyl)-5-(2-[2-hydroxyethyl-amino]pyrimidin-4-yl)-N-H-imidazole (H4.6.2)

Example H4.6.3

2-(2,6-dichloro-4-(2-carboxymethoxy)phenyl)-4-(3-benzyloxyphenyl)-5-(2-[3-methoxypropyl-amino]pyrimidin-4-yl)-N-H-imidazole (H4.6.3)

Example H4.6.4

2-(2,6-dichloro-4-(2-carboxymethoxy)phenyl)-4-(3-benzyloxyphenyl)-5-(2-[2-methoxyethyl-amino]pyrimidin-4-yl)-N-H-imidazole (H4.6.4)

Example H4.6.5

2-(2,6-dichloro-4-(2-carboxymethoxy)phenyl)-4-(3-benzyloxyphenyl)-5-(2-[2,3-dihydroxypropyl-amino]pyrimidin-4-yl)-N-H-imidazole (H4.6.5)

Example H4.7.1

(rac)-2-(2,6-dichloro-4-(2,2-dimethyl-[1,3]-dioxolane-4-ylmethoxy)phenyl)-4-(3-benzyloxyphenyl)-5-(2-[3-hydroxypropylamino]pyrimidin-4-yl)-N-H-imidazole (H4.7.1)

(R)-2-(2,6-dichloro-4-(2,2-dimethyl-[1,3]-dioxolane-4-ylmethoxy)phenyl)-4-(3-benzyloxyphenyl)-5-(2-[3-hydroxypropylamino]pyrimidin-4-yl)-N-H-imidazole (H4.7.1.1)

(S)-2-(2,6-dichloro-4-(2,2-dimethyl-[1,3]-dioxolane-4-ylmethoxy)phenyl)-4-(3-benzyloxyphenyl)-5-(2-[3-hydroxypropylamino]pyrimidin-4-yl)-N-H-imidazole (H4.7.1.2)

Example H4.7.2

(rac)-2-(2,6-dichloro-4-(2,2-dimethyl-[1,3]-dioxolane-4-ylmethoxy)phenyl)-4-(3-benzyloxyphenyl)-5-(2-[2-hydroxyethylamino]pyrimidin-4-yl)-N-H-imidazole (H4.7.2)

(R)-2-(2,6-dichloro-4-(2,2-dimethyl-[1,3]-dioxolane-4-ylmethoxy)phenyl)-4-(3-benzyloxyphenyl)-5-(2-[2-hydroxyethylamino]pyrimidin-4-yl)-N-H-imidazole (H4.7.2.1)

(S)-2-(2,6-dichloro-4-(2,2-dimethyl-[1,3]-dioxolane-4-ylmethoxy)phenyl)-4-(3-benzyloxyphenyl)-5-(2-[2-hydroxyethylamino]pyrimidin-4-yl)-N-H-imidazole (H4.7.2.2)

Example H4.7.3

(rac)-2-(2,6-dichloro-4-(2,2-dimethyl-[1,3]-dioxolane-4-ylmethoxy)phenyl)-4-(3-benzyloxyphenyl)-5-(2-[3-methoxypropylamino]pyrimidin-4-yl)-N-H-imidazole (H4.7.3)

(R)-2-(2,6-dichloro-4-(2,2-dimethyl-[1,3]-dioxolane-4-ylmethoxy)phenyl)-4-(3-benzyloxyphenyl)-5-(2-[3-methoxypropylamino]pyrimidin-4-yl)-N-H-imidazole (H4.7.3.1)

(S)-2-(2,6-dichloro-4-(2,2-dimethyl-[1,3]-dioxolane-4-ylmethoxy)phenyl)-4-(3-benzyloxyphenyl)-5-(2-[3-methoxypropylamino]pyrimidin-4-yl)-N-H-imidazole (H4.7.3.2)

Example H4.7.4

(rac)-2-(2,6-dichloro-4-(2,2-dimethyl-[1,3]-dioxolane-4-ylmethoxy)phenyl)-4-(3-benzyloxyphenyl)-5-(2-[2-methoxyethylamino]pyrimidin-4-yl)-N-H-imidazole (H4.7.4)

(R)-2-(2,6-dichloro-4-(2,2-dimethyl-[1,3]-dioxolane-4-ylmethoxy)phenyl)-4-(3-benzyloxyphenyl)-5-(2-[2-methoxyethylamino]pyrimidin-4-yl)-N-H-imidazole (H4.7.4.1)

(S)-2-(2,6-dichloro-4-(2,2-dimethyl-[1,3]-dioxolane-4-ylmethoxy)phenyl)-4-(3-benzyloxyphenyl)-5-(2-[2-methoxyethylamino]pyrimidin-4-yl)-N-H-imidazole (H4.7.4.2)

Example H4.7.5

(rac)-2-(2,6-dichloro-4-(2,2-dimethyl-[1,3]-dioxolane-4-ylmethoxy)phenyl)-4-(3-benzyloxyphenyl)-5-(2-[2,3-dihydroxypropylamino]pyrimidin-4-yl)-N-H-imidazole (H4.7.5)

(R)-2-(2,6-dichloro-4-(2,2-dimethyl-[1,3]-dioxolane-4-ylmethoxy)phenyl)-4-(3-benzyloxyphenyl)-5-(2-[2,3-dihydroxypropylamino]pyrimidin-4-yl)-N-H-imidazole (H4.7.5.1)

(S)-2-(2,6-dichloro-4-(2,2-dimethyl-[1,3]-dioxolane-4-ylmethoxy)phenyl)-4-(3-benzyloxyphenyl)-5-(2-[2,3-dihydroxypropylamino]pyrimidin-4-yl)-N-H-imidazole (H4.7.5.2)

Example H4.8.1

(rac)-2-(2,6-dichloro-4-(2,3-dihydroxypropoxy)
phenyl)-4-(3-benzyloxyphenyl)-5-(2-[3-
hydroxypropyl-amino]pyrimidin-4-yl)-N-H-
imidazole (H4.8.1)

(R)-2-(2,6-dichloro-4-(2,3-dihydroxypropoxy)
phenyl)-4-(3-benzyloxyphenyl)-5-(2-[3-
hydroxypropyl-amino]pyrimidin-4-yl)-N-H-
imidazole (H4.8.1.1)

An analogous reaction to that described in example H1.1, but starting with G4.8.2 gave H4.8.2.1 in 55% yield.
MS: M=636 (API+), 634 (API−)

(S)-2-(2,6-dichloro-4-(2,3-dihydroxypropoxy)
phenyl)-4-(3-benzyloxyphenyl)-5-(2-[3-
hydroxypropyl-amino]pyrimidin-4-yl)-N-H-
imidazole (H4.8.1.2)

An analogous reaction to that described in example H1.1, but starting with G4.8.1 gave H4.8.1.1 in 55% yield.
MS: M=636 (API+), 634 (API−)

Example H4.8.2

(rac)-2-(2,6-dichloro-4-(2,3-dihydroxypropoxy)
phenyl)-4-(3-benzyloxyphenyl)-5-(2-[2-
hydroxyethyl-amino]pyrimidin-4-yl)-N-H-imidazole
(H4.8.2)

(R)-2-(2,6-dichloro-4-(2,3-dihydroxypropoxy)
phenyl)-4-(3-benzyloxyphenyl)-5-(2-[2-
hydroxyethyl-amino]pyrimidin-4-yl)-N-H-imidazole
(H4.8.2.1)

An analogous reaction to that described in example H1.1, but starting with G4.8.1 and 2-aminoethanol gave H4.8.1.2 in 46% yield.
MS: M=622 (API+), 620 (API−)

(S)-2-(2,6-dichloro-4-(2,3-dihydroxypropoxy)
phenyl)-4-(3-benzyloxyphenyl)-5-(2-[2-
hydroxyethyl-amino]pyrimidin-4-yl)-N-H-imidazole
(H4.8.2.2)

An analogous reaction to that described in example H1.1, but starting with G4.8.2 and 2-aminoethanol gave H4.8.2.2 in 87% yield.
MS: M=622 (API+), 620 (API−)

Example H4.8.3

(rac)-2-(2,6-dichloro-4-(2,3-dihydroxypropoxy)
phenyl)-4-(3-benzyloxyphenyl)-5-(2-[3-
methoxypropyl-amino]pyrimidin-4-yl)-N-H-
imidazole (H4.8.3)

(R)-2-(2,6-dichloro-4-(2,3-dihydroxypropoxy)
phenyl)-4-(3-benzyloxyphenyl)-5-(2-[3-
methoxypropyl-amino]pyrimidin-4-yl)-N-H-
imidazole (H4.8.3.1)

An analogous reaction to that described in example H1.1, but starting with G4.8.2 and and 3-methoxy-propylamine gave H4.8.2.3 in 58% yield.
MS: M=650 (API+), 648 (API−)

(S)-2-(2,6-dichloro-4-(2,3-dihydroxypropoxy)
phenyl)-4-(3-benzyloxyphenyl)-5-(2-[3-
methoxypropyl-amino]pyrimidin-4-yl)-N-H-
imidazole (H4.8.3.2)

An analogous reaction to that described in example H1.1, but starting with G4.8.1 and and 3-methoxy-propylamine gave H4.8.1.3 in 68% yield.
MS: M=650 (API+), 648 (API−)

Example H4.8.4

(rac)-2-(2,6-dichloro-4-(2,3-dihydroxypropoxy)
phenyl)-4-(3-benzyloxyphenyl)-5-(2-[2-
methoxyethyl-amino]pyrimidin-4-yl)-N-H-imidazole
(H4.8.4)

(R)-2-(2,6-dichloro-4-(2,3-dihydroxypropoxy)
phenyl)-4-(3-benzyloxyphenyl)-5-(2-[2-
methoxyethyl-amino]pyrimidin-4-yl)-N-H-imidazole
(H4.8.4.1)

An analogous reaction to that described in example H1.1, but starting with G4.8.1 and 2-methoxy-ethylamine gave H4.8.1.4in 20% yield.
MS: M=622 (API+), 620 (API−)

(S)-2-(2,6-dichloro-4-(2,3-dihydroxypropoxy)
phenyl)-4-(3-benzyloxyphenyl)-5-(2-[2-
methoxyethyl-amino]pyrimidin-4-yl)-N-H-imidazole
(H4.8.4.2)

An analogous reaction to that described in example H1.1, but starting with G4.8.2 and and 2-methoxy-ethylamine gave H4.8.2.4 in 45% yield.
MS: M=622 (API+), 620 (API−)

Example H4.8.5

(rac)-2-(2,6-dichloro-4-(2,3-dihydroxypropoxy)
phenyl)-4-(3-benzyloxyphenyl)-5-(2-[2,3-
dihydroxyethyl-amino]pyrimidin-4-yl)-N-H-
imidazole (H4.8.5)

(R)-2-(2,6-dichloro-4-(2,3-dihydroxypropoxy)
phenyl)-4-(3-benzyloxyphenyl)-5-(2-[2,3-
dihydroxyethyl-amino]pyrimidin-4-yl)-N-H-
imidazole (H4.8.5.1)

(S)-2-(2,6-dichloro-4-(2,3-dihydroxypropoxy)
phenyl)-4-(3-benzyloxyphenyl)-5-(2-[2,3-
dihydroxyethyl-amino]pyrimidin-4-yl)-N-H-
imidazole (H4.8.5.2)

Example H4.9.1

2-(2,6-dichloro-4-(dimethylphoshinoylmethoxy)
phenyl)-4-(3-benzyloxyphenyl)-5-(2-[3-
hydroxypropyl-amino]pyrimidin-4-yl)-N-H-
imidazole (H4.9.1)

An analogous reaction to that described in example H1.1, but starting with G4.9 gave H4.9.1 in 66% yield.
MS: M=652 (API+)

Example H4.9.2

2-(2,6-dichloro-4-(dimethylphoshinoylmethoxy)
phenyl)-4-(3-benzyloxyphenyl)-5-(2-[2-
hydroxyethyl-amino]pyrimidin-4-yl)-N-H-imidazole
(H4.9.2)

Example H4.9.3

2-(2,6-dichloro-4-(dimethylphoshinoylmethoxy)phenyl)-4-(3-benzyloxyphenyl)-5-(2-[3-methoxypropyl-amino]pyrimidin-4-yl)-N-H-imidazole (H4.9.3)

Example H4.9.4

2-(2,6-dichloro-4-(dimethylphoshinoylmethoxy)phenyl)-4-(3-benzyloxyphenyl)-5-(2-[2-methoxyethyl-amino]pyrimidin-4-yl)-N-H-imidazole (H4.9.4)

Example H4.9.5

2-(2,6-dichloro-4-(dimethylphoshinoylmethoxy)phenyl)-4-(3-benzyloxyphenyl)-5-(2-[2,3-dihydroxypropyl-amino]pyrimidin-4-yl)-N-H-imidazole (H4.9.5)

Example H4.10.1

2-(2,6-dichloro-4-methylthiophenyl)-4-(3-benzyloxyphenyl)-5-(2-[3-hydroxypropyl-amino]pyrimidin-4-yl)-N-H-imidazole (H4.10.1)

Example H4.10.2

2-(2,6-dichloro-4-methylthiophenyl)-4-(3-benzyloxyphenyl)-5-(2-[2-hydroxyethyl-amino]pyrimidin-4-yl)-N-H-imidazole (H4.10.2)

Example H4.10.3

2-(2,6-dichloro-4-methylthiophenyl)-4-(3-benzyloxyphenyl)-5-(2-[3-methoxypropyl-amino]pyrimidin-4-yl)-N-H-imidazole (H4.10.3)

Example H4.10.4

2-(2,6-dichloro-4-methylthiophenyl)-4-(3-benzyloxyphenyl)-5-(2-[2-methoxyethyl-amino]pyrimidin-4-yl)-N-H-imidazole (H4.10.4)

Example H4.10.5

2-(2,6-dichloro-4-methylthiophenyl)-4-(3-benzyloxyphenyl)-5-(2-[2,3-dihydroxypropyl-amino]pyrimidin-4-yl)-N-H-imidazole (H4.10.5)

Example H4.11.1

2-(2,6-dichloro-4-methanesulfinylphenyl)-4-(3-benzyloxyphenyl)-5-(2-[3-hydroxypropyl-amino]-pyrimidin-4-yl)-N-H-imidazole (H4.11.1)

An analogous reaction to that described in example H1.1, but starting with G4.11 gave H4.11.1 in 59% yield.
MS: M=608 (API+)

Example H4.11.2

2-(2,6-dichloro-4-methanesulfinylphenyl)-4-(3-benzyloxyphenyl)-5-(2-[2-hydroxyethyl-amino]-pyrimidin-4-yl)-N-H-imidazole (H4.11.2)

Example H4.11.3

2-(2,6-dichloro-4-methanesulfinylphenyl)-4-(3-benzyloxyphenyl)-5-(2-[3-methoxypropyl-amino]-pyrimidin-4-yl)-N-H-imidazole (H4.11.3)

Example H4.11.4

2-(2,6-dichloro-4-methanesulfinylphenyl)-4-(3-benzyloxyphenyl)-5-(2-[2-methoxyethyl-amino]-pyrimidin-4-yl)-N-H-imidazole (H4.11.4)

Example H4.11.5

2-(2,6-dichloro-4-methanesulfinylphenyl)-4-(3-benzyloxyphenyl)-5-(2-[2,3-dihydroxypropyl-amino]-pyrimidin-4-yl)-N-H-imidazole (H4.11.5)

Example H4.12.1

2-(2,6-dichloro-4-methanesulfonylphenyl)-4-(3-benzyloxyphenyl)-5-(2-[3-hydroxypropyl-amino]pyrimidin-4-yl)-N-H-imidazole (H4.12.1)

Example H4.12.2

2-(2,6-dichloro-4-methanesulfonylphenyl)-4-(3-benzyloxyphenyl)-5-(2-[2-hydroxyethyl-amino]pyrimidin-4-yl)-N-H-imidazole (H4.12.2)

Example H4.12.3

2-(2,6-dichloro-4-methanesulfonylphenyl)-4-(3-benzyloxyphenyl)-5-(2-[3-methoxypropyl-amino]pyrimidin-4-yl)-N-H-imidazole (H4.12.3)

Example H4.12.4

2-(2,6-dichloro-4-methanesulfonylphenyl)-4-(3-benzyloxyphenyl)-5-(2-[2-methoxypropyl-amino]pyrimidin-4-yl)-N-H-imidazole (H4.12.4)

Example H4.12.5

2-(2,6-dichloro-4-methanesulfonylphenyl)-4-(3-benzyloxyphenyl)-5-(2-[2,3-dihydroxypropyl-amino]pyrimidin-4-yl)-N-H-imidazole (H4.12.5)

Example H4.13.1

2-(2,6-dichloro-4-cyanomethyloxyphenyl)-4-(3-benzyloxyphenyl)-5-(2-[3-hydroxypropyl-amino]pyrimidin-4-yl)-N-H-imidazole (H4.13.1)

Example H4.13.2

2-(2,6-dichloro-4-cyanomethyloxyphenyl)-4-(3-benzyloxyphenyl)-5-(2-[2-hydroxyethyl-amino]pyrimidin-4-yl)-N-H-imidazole (H4.13.2)

Example H4.13.3

2-(2,6-dichloro-4-cyanomethyloxyphenyl)-4-(3-benzyloxyphenyl)-5-(2-[3-methoxypropyl-amino]pyrimidin-4-yl)-N-H-imidazole (H4.13.3)

Example H4.13.4

2-(2,6-dichloro-4-cyanomethyloxyphenyl)-4-(3-benzyloxyphenyl)-5-(2-[2-methoxyethyl-amino]pyrimidin-4-yl)-N-H-imidazole (H4.13.4)

Example H4.13.5

2-(2,6-dichloro-4-cyanomethyloxyphenyl)-4-(3-benzyloxyphenyl)-5-(2-[2,3-dihydroxypropyl-amino]pyrimidin-4-yl)-N-H-imidazole (H4.13.5)

Example H4.14.1

2-(2,6-dichloro-4-(N-morpholino)methylphenyl)-4-(3-benzyloxyphenyl)-5-(2-[3-hydroxypropyl-amino]pyrimidin-4-yl)-N-H-imidazole (H4.14.1)

Example H4.14.2

2-(2,6-dichloro-4-(N-morpholino)methylphenyl)-4-(3-benzyloxyphenyl)-5-(2-[2-hydroxyethyl-amino]pyrimidin-4-yl)-N-H-imidazole (H4.14.2)

Example H4.14.3

2-(2,6-dichloro-4-(N-morpholino)methylphenyl)-4-(3-benzyloxyphenyl)-5-(2-[3-methoxypropyl-amino]pyrimidin-4-yl)-N-H-imidazole (H4.14.3)

Example H4.14.4

2-(2,6-dichloro-4-(N-morpholino)methylphenyl)-4-(3-benzyloxyphenyl)-5-(2-[2-methoxyethyl-amino]pyrimidin-4-yl)-N-H-imidazole (H4.14.4)

Example H4.14.5

2-(2,6-dichloro-4-(N-morpholino)methylphenyl)-4-(3-benzyloxyphenyl)-5-(2-[2,3-dihydroxypropyl-amino]pyrimidin-4-yl)-N-H-imidazole (H4.14.5)

Example H4.15.1

2-(2,6-dichloro-4-ethoxycarbonylmethylthiomethylphenyl)-4-(3-benzyloxyphenyl)-5-(2-[3-hydroxypropyl-amino]pyrimidin-4-yl)-N-H-imidazole (H4.15.1)

Example H4.15.2

2-(2,6-dichloro-4-ethoxycarbonylmethylthiomethylphenyl)-4-(3-benzyloxyphenyl)-5-(2-[2-hydroxyethyl-amino]pyrimidin-4-yl)-N-H-imidazole (H4.15.2)

Example H4.15.3

2-(2,6-dichloro-4-ethoxycarbonylmethylthiomethylphenyl)-4-(3-benzyloxyphenyl)-5-(2-[3-methoxypropyl-amino]pyrimidin-4-yl)-N-H-imidazole (H4.15.3)

Example H4.15.4

2-(2,6-dichloro-4-ethoxycarbonylmethylthiomethylphenyl)-4-(3-benzyloxyphenyl)-5-(2-[2-methoxyethyl-amino]pyrimidin-4-yl)-N-H-imidazole (H4.15.4)

Example H4.15.5

2-(2,6-dichloro-4-ethoxycarbonylmethylthiomethylphenyl)-4-(3-benzyloxyphenyl)-5-(2-[2,3-dihydroxypropyl-amino]pyrimidin-4-yl)-N-H-imidazole (H4.15.5)

Example H4.16.1

2-(2,6-dichloro-4-hydroxyethylthiomethylphenyl)-4-(3-benzyloxyphenyl)-5-(2-[3-hydroxypropyl-amino]pyrimidin-4-yl)-N-H-imidazole (H4.16.1)

Example H4.16.2

2-(2,6-dichloro-4-hydroxyethylthiomethylphenyl)-4-(3-benzyloxyphenyl)-5-(2-[2-hydroxyethyl-amino]pyrimidin-4-yl)-N-H-imidazole (H4.16.2)

Example H4.16.3

2-(2,6-dichloro-4-hydroxyethylthiomethylphenyl)-4-(3-benzyloxyphenyl)-5-(2-[3-methoxypropyl-amino]pyrimidin-4-yl)-N-H-imidazole (H4.16.3)

Example H4.16.4

2-(2,6-dichloro-4-hydroxyethylthiomethylphenyl)-4-(3-benzyloxyphenyl)-5-(2-[2-methoxyethyl-amino]pyrimidin-4-yl)-N-H-imidazole (H4.16.4)

Example H4.16.5

2-(2,6-dichloro-4-hydroxyethylthiomethylphenyl)-4-(3-benzyloxyphenyl)-5-(2-[2,3-dihydroxypropyl-amino]pyrimidin-4-yl)-N-H-imidazole (H4.16.5)

Example H4.17.1

2-(2,6-dichloro-4-(N-morpholinoethylaminomethyl)phenyl)-4-(3-benzyloxyphenyl)-5-(2-[3-hydroxypropyl-amino]pyrimidin-4-yl)-N-H-imidazole (H4.17.1)

Example H4.17.2

2-(2,6-dichloro-4-(N-morpholinoethylaminomethyl) phenyl)-4-(3-benzyloxyphenyl)-5-(2-[2-hydroxyethyl-amino]pyrimidin-4-yl)-N-H-imidazole (H4.17.2)

Example H4.17.3

2-(2,6-dichloro-4-(N-morpholinoethylaminomethyl) phenyl)-4-(3-benzyloxyphenyl)-5-(2-[3-methoxypropyl-amino]pyrimidin-4-yl)-N-H-imidazole (H4.17.3)

Example H4.17.4

2-(2,6-dichloro-4-(N-morpholinoethylaminomethyl) phenyl)-4-(3-benzyloxyphenyl)-5-(2-[2-methoxyethyl-amino]pyrimidin-4-yl)-N-H-imidazole (H4.17.4)

Example H4.17.5

2-(2,6-dichloro-4-(N-morpholinoethylaminomethyl) phenyl)-4-(3-benzyloxyphenyl)-5-(2-[2,3-dihydroxypropyl-amino]pyrimidin-4-yl)-N-H-imidazole (H4.17.5)

Example H4.18.1

2-(2,6-dichloro-4-(2-hydroxy-1-hydroxymethyl-ethoxy)-phenyl)-4-(3-benzyloxyphenyl)-5-(2-[3-hydroxypropyl-amino]pyrimidin-4-yl)-N-H-imidazole (H4.18.1)

An analogous reaction to that described in example H1.1.1, but starting with G4.18 gave H4.18.1 in 31% yield. MS: M=636 (API+)

Example H4.18.2

2-(2,6-dichloro-4-(2-hydroxy-1-hydroxymethyl-ethoxy)-phenyl)-4-(3-benzyloxyphenyl)-5-(2-[2-hydroxyethyl-amino]pyrimidin-4-yl)-N-H-imidazole (H4.18.2)

Example H4.18.3

2-(2,6-dichloro-4-(2-hydroxy-1-hydroxymethyl-ethoxy)-phenyl)-4-(3-benzyloxyphenyl)-5-(2-[3-methoxypropyl-amino]pyrimidin-4-yl)-N-H-imidazole (H4.18.3)

Example H4.18.4

2-(2,6-dichloro-4-(2-hydroxy-1-hydroxymethyl-ethoxy)-phenyl)-4-(3-benzyloxyphenyl)-5-(2-[2-methoxyethyl-amino]pyrimidin-4-yl)-N-H-imidazole (H4.18.4)

Example H4.18.5

2-(2,6-dichloro-4-(2-hydroxy-1-hydroxymethyl-ethoxy)-phenyl)-4-(3-benzyloxyphenyl)-5-(2-[2,3-dihydroxypropyl-amino]pyrimidin-4-yl)-N-H-imidazole (H4.18.5)

Example H4.19.1

2-(2,6-dichloro-4-(3-hydroxy-2-hydroxymethyl-propoxy)-phenyl)-4-(3-benzyloxyphenyl)-5-(2-[3-hydroxypropyl-amino]pyrimidin-4-yl)-N-H-imidazole (H4.19.1)

Example H4.19.2

2-(2,6-dichloro-4-(3-hydroxy-2-hydroxymethyl-propoxy)-phenyl)-4-(3-benzyloxyphenyl)-5-(2-[2-hydroxyethyl-amino]pyrimidin-4-yl)-N-H-imidazole (H4.19.2)

Example H4.19.3

2-(2,6-dichloro-4-(3-hydroxy-2-hydroxymethyl-propoxy)-phenyl)-4-(3-benzyloxyphenyl)-5-(2-[3-methoxypropyl-amino]pyrimidin-4-yl)-N-H-imidazole (H4.19.3)

Example H4.19.4

2-(2,6-dichloro-4-(3-hydroxy-2-hydroxymethyl-propoxy)-phenyl)-4-(3-benzyloxyphenyl)-5-(2-[2-methoxyethyl-amino]pyrimidin-4-yl)-N-H-imidazole (H4.19.4)

Example H4.19.5

2-(2,6-dichloro-4-(3-hydroxy-2-hydroxymethyl-propoxy)-phenyl)-4-(3-benzyloxyphenyl)-5-(2-[2,3-dihydroxypropyl-amino]pyrimidin-4-yl)-N-H-imidazole (H4.19.5)

Example H5.1.1

2-(2,6-dichlorophenyl)-4-(3-hydroxyphenyl)-5-(2-[3-hydroxypropylamino]pyrimidin-4-yl)-N-H-imidazole (H5.1.1)

Example H5.1.2

2-(2,6-dichlorophenyl)-4-(3-hydroxyphenyl)-5-(2-[2-hydroxyethylamino]pyrimidin-4-yl)-N-H-imidazole (H5.1.2)

Example H5.1.3

2-(2,6-dichlorophenyl)-4-(3-hydroxyphenyl)-5-(2-[3-methoxypropylamino]pyrimidin-4-yl)-N-H-imidazole (H5.1.3)

Example H5.1.4

2-(2,6-dichlorophenyl)-4-(3-hydroxyphenyl)-5-(2-[2-methoxyethylamino]pyrimidin-4-yl)-N-H-imidazole (H5.1.4)

Example H5.1.5

2-(2,6-dichlorophenyl)-4-(3-hydroxyphenyl)-5-(2-[2,3-dihydroxypropylamino]pyrimidin-4-yl)-N-H-imidazole (H5.1.5)

Example H5.2.1

2-(2,6-dichloro-4-hydroxyphenyl)-4-(3-hydroxyphenyl)-5-(2-[3-hydroxypropylamino]pyrimidin-4-yl)-N-H-imidazole (H5.2.1)

Example H5.2.2

2-(2,6-dichloro-4-hydroxyphenyl)-4-(3-hydroxyphenyl)-5-(2-[2-hydroxyethylamino]-pyrimidin-4-yl)-N-H-imidazole (H5.2.2)

Example H5.2.3

2-(2,6-dichloro-4-hydroxyphenyl)-4-(3-hydroxyphenyl)-5-(2-[3-methoxypropylamino]-pyrimidin-4-yl)-N-H-imidazole (H5.2.3)

Example H5.2.4

2-(2,6-dichloro-4-hydroxyphenyl)-4-(3-hydroxyphenyl)-5-(2-[2-methoxyethylamino]-pyrimidin-4-yl)-N-H-imidazole (H5.2.4)

Example H5.2.5

2-(2,6-dichloro-4-hydroxyphenyl)-4-(3-hydroxyphenyl)-5-(2-[2,3-dihydroxypropyl-amino]pyrimidin-4-yl)-N-H-imidazole (H5.2.5)

Example H5.3.1

2-(2,6-dichloro-4-hydroxymethylphenyl)-4-(3-hydroxyphenyl)-5-(2-[3-hydroxypropylamino]pyrimidin-4-yl)-N-H-imidazole (H5.3.1)

MS: M=486.4 (API+)

Example H5.3.2

2-(2,6-dichloro-4-hydroxymethylphenyl)-4-(3-hydroxyphenyl)-5-(2-[2-hydroxyethylamino]pyrimidin-4-yl)-N-H-imidazole (H5.3.2)

MS: M=472.4 (API+)

Example H5.3.3

2-(2,6-dichloro-4-hydroxymethylphenyl)-4-(3-hydroxyphenyl)-5-(2-[3-methoxypropylamino]pyrimidin-4-yl)-N-H-imidazole (H5.3.3)

MS: M=500.4 (API+)

Example H5.3.4

2-(2,6-dichloro-4-hydroxymethylphenyl)-4-(3-hydroxyphenyl)-5-(2-[2-methoxyethylamino]pyrimidin-4-yl)-N-H-imidazole (H5.3.4)

MS: M=486.4 (API+)

Example H5.3.5

(rac)-2-(2,6-dichloro-4-hydroxymethylphenyl)-4-(3-hydroxyphenyl)-5-(2-[2,3-dihydroxypropyl-amino]pyrimidin-4-yl)-N-H-imidazole (H5.3.5)

MS: M=502.4 (API+)

Example H6.1.1

2-(2,6-dichlorophenyl)-4-(3-methoxymethoxyphenyl)-5-(2-[3-hydroxypropylamino]pyrimidin-4-yl)-N-H-imidazole (H6.1.1)

An analogous reaction to that described in example H1.1.1, but starting with G6.1 gave H6.1.1 in 83% yield, m.p. 160–162° C.

MS: M=500 (ESI+), M=498 (ESI−). $^1$H-NMR (250 MHz, CDCl$_3$): δ=5.20 (s, 2H, OCH$_2$O), 6.63 (d, 1H, 5-H-pyrimidine), 8.22 (d, 1H, 6-H-pyrimidine), 12.9 (s, 1H, NH).
$^{13}$C-NMR (62.9 MHz, D$_6$-DMSO): δ=32.1 (C-2'), 55.5 (OCH$_3$), 58.6 (CH$_2$OH), 93.8 (OCH$_2$O).

Example H6.1.2

2-(2,6-dichlorophenyl)-4-(3-methoxymethoxyphenyl)-5-(2-[2-hydroxyethylamino]pyrimidin-4-yl)-N-H-imidazole (H6.1.2)

An analogous reaction to that described in example H1.1.1, but starting with G6.1 and 2-aminoethanol gave H6.1.2 in 45% yield

MS: M=486 (API+)

Example H6.1.3

2-(2,6-dichlorophenyl)-4-(3-methoxymethoxyphenyl)-5-(2-[3-methoxypropylamino]pyrimidin-4-yl-N-H-imidazole (H6.1.3)

An analogous reaction to that described in example H1.1.1, but starting with G6.1 and 3-methoxy-propylamine gave H6.1.3 in 43% yield

MS: M=514 (API+)

Example H6.1.4

2-(2,6-dichlorophenyl)-4-(3-methoxymethoxyphenyl)-5-(2-[2-methoxyethylamino]pyrimidin-4-yl-N-H-imidazole (H6.1.4)

An analogous reaction to that described in example H1.1.1, but starting with G6.1 and 2-methoxyethylamine gave H6.1.4 in 47% yield

MS: M=500 (API+)

Example H6.1.5

(rac)-2-(2,6-dichlorophenyl)-4-(3-methoxymethoxyphenyl)-5-(2-[3-hydroxybutylamino]pyrimidin-4-yl-N-H-imidazole (H6.1.5)

An analogous reaction to that described in example H1.1.1, but starting with G6.1 and 3-hydroxybutylamine gave H6.1.5 in 13% yield

MS: M=514 (API+)

Example H6.1.6

(rac)-2-(2,6-dichlorophenyl)-4-(3-methoxymethoxyphenyl)-5-(2-[2,3-dihydroxypropylamino]pyrimidin-4-yl-N-H-imidazole (H6.1.6)

An analogous reaction to that described in example H1.1.1, but starting with G6.1 and 2,3-dihydroxypropylamine gave H6.1.6 in 78% yield

MS: M=516 (API+)

Example H6.1.7

2-(2,6-dichlorophenyl)-4-(3-methoxymethoxyphenyl)-5-(2-[2-(2-dimethylaminoethyl)thioethylamino]-pyrimidin-4-yl)-N-H-imidazole (H6.1.7)

An analogous reaction to that described in example H1.1.1, but starting with G6.1 and 2-(2-dimethylaminoethyl)thioethylamine gave H6.1.7 in 55% yield MS: M=573 (ESI+), M=571 (ESI−). $^1$H-NMR (250 MHz, CDCl$_3$): δ=2.23 (s, 6H, NCH$_3$), 2.45–2.75 (m, 4 H, S(CH$_2$)$_2$N), 2.82 (t, 2H, CH$_2$S), 3.50 (s, 3H, OCH$_3$), 3.68 (q, 2H, CH$_2$—NH), 5.22 (s, 2H, OCH$_2$O), 5.54 (t, 1H, NH), 6.86 (d, 1H, 5-H-pyrimidine), 7.05 (m, 1H, Ar—H), 7.3–7.5 (m, 6H, Ar—H), 8.12 (d, 1H, 6-H-pyrimidine), 10.5 (br, 1H, NH).

Example H6.1.8

2-(2,6-dichlorophenyl)-4-(3-methoxymethoxyphenyl)-5-(2-[2-(2-dimethylaminoethyl)thiopropylamino]-pyrimidin-4-yl)-N-H-imidazole (H6.1.8)

An analogous reaction to that described in example H1.1.1, but starting with G6.1 and 2-(2-dimethylaminoethyl)thiopropylamine gave H6.1.8 in 69% yield MS: M=587 (ESI+), M=585 (ESI−). $^1$H-NMR (250 MHz, CDCl$_3$): δ=1.95 (quintett, 2H, C—CH$_2$—C), 2.21 (s, 6H, NCH$_3$), 2.4–2.7 (m, 4H, S(CH$_2$)$_2$N), 2.65 (t, 2H, CH$_2$S), 3.48 (s, 3H, OCH$_3$), 3.58 (q, 2H, NH—CH$_2$), 5.20 (s, 2H, OCH$_2$O), 5.26 (t, 1H, NH), 6.84 (d, 1H, 5-H-pyrimidine), 7.05 (m, 1H, Ar—H), 7.3–7.5 (m, 6H, Ar—H), 8.08 (d, 1H, 6-H-pyrimidine), 10.8 (br, 1H, NH).

Example H6.1.9

2-(2,6-dichlorophenyl)-4-(3-methoxymethoxyphenyl)-5-(2-[2-(morpholin-4-yl)ethylamino]-pyrimidin-4-yl)-N-H-imidazole (H6.1.9)

An analogous reaction to that described in example H1.1.1, but starting with G6.1 and 4-(2-aminoethyl)morpholine gave H6.1.9 in 91% yield

MS: M=555 (API+), 553 (API−)

Example H6.1.10

2-(2,6-dichlorophenyl)-4-(3-methoxymethoxyphenyl)-5-(2-[3-(morpholin-4-yl)propylamino]-pyrimidin-4-yl)-N-H-imidazole (H6.1.10)

An analogous reaction to that described in example H1.1.1, but starting with G6.1 and 4-(3-aminopropyl)morpholine gave H6.1.10 in 90% yield

MS: M=569 (API+), 567 (API−)

Example H6.1.11

2-(2,6-dichlorophenyl)-4-(3-methoxymethoxyphenyl)-5-(2-[3-(N-methylpiperazin-1-yl)propylamino]-pyrimidin-4-yl)-N-H-imidazole (H6.1.11)

An analogous reaction to that described in example H1.1.1, but starting with G6.1 and 1-(3-aminopropyl)-4-methylpiperazine gave H6.1.11 in 86% yield

MS: M=582 (API+), 580 (API−)

Example H6.1.12

2-(2,6-dichlorophenyl)-4-(3-methoxymethoxyphenyl)-5-(2-[2-(2-dimethylaminoethoxy)ethylamino]-pyrimidin-4-yl)-N-H-imidazole (H6.1.12)

An analogous reaction to that described in example H1.1.1, but starting with G6.1 and 2-(2-dimethylaminoethoxy)ethylamine gave H6.1.12 in 86% yield.

MS: M=557 (API+), 555 (API−)

Example H6.1.13

2-(2,6-dichlorophenyl)-4-(3-methoxymethoxyphenyl)-5-(2-[2-(2-morpholin-4-ylethoxy)ethylamino]-pyrimidin-4-yl)-N-H-imidazole (H6.1.13)

An analogous reaction to that described in example H1.1.1, but starting with G6.1 and 2-(2-morpholin-4-ylethoxy)ethylamine gave H6.1.13 in 79% yield.

MS: M=599 (API+), 597 (API−)

Example H6.2.1

2-(2,6-dichloro-4-hydroxyphenyl)-4-(3-methoxymethoxyphenyl)-5-(2-[3-hydroxypropylamino]pyrimidin-4-yl)-N-H-imidazole (H6.2.1)

An analogous reaction to that described in example H1.1.1, but starting with G6.2 gave H6.2.1 in 43% yield.

MS: M=516 (API+)

Example H6.2.2

2-(2,6-dichloro-4-hydroxyphenyl)-4-(3-methoxymethoxyphenyl)-5-(2-[2-hydroxyethylamino]pyrimidin-4-yl)-N-H-imidazole (H6.2.2)

An analogous reaction to that described in example H1.1.1, but starting with G6.2 and 2-aminoethanol gave H6.2.2 in 67% yield

MS: M=502 (API+)

Example H6.2.3

2-(2,6-dichloro-4-hydroxyphenyl)-4-(3-methoxymethoxyphenyl)-5-(2-[3-methoxypropylamino]pyrimidin-4-yl-N-H-imidazole (H6.2.3)

An analogous reaction to that described in example H1.1.1, but starting with G6.2 and 3-methoxypropylamine gave H6.2.3 in 65% yield

MS: M=530 (API+)

Example H6.2.4

2-(2,6-dichloro-4-hydroxyphenyl)-4-(3-methoxymethoxyphenyl)-5-(2-[2-methoxyethylamino]pyrimidin-4-yl-N-H-imidazole (H6.2.4)

An analogous reaction to that described in example H1.1.1, but starting with G6.2 and 2-methoxyethylamine gave H6.2.4 in 67% yield

MS: M=516 (API+)

Example H6.2.5

(rac)-2-(2,6-dichloro-4-hydroxyphenyl)-4-(3-methoxymethoxyphenyl)-5-(2-[2,3-dihydroxypropylamino]-pyrimidin-4-yl-N-H-imidazole (H6.2.5)

An analogous reaction to that described in example H1.1.1, but starting with G6.2 and 2,3-dihydroxypropylamine gave H6.2.5 in 57% yield
MS: M=532 (API+)

Example H6.3.1

2-(2,6-dichloro-4-hydroxymethylphenyl)-4-(3-methoxymethoxyphenyl)-5-(2-[3-hydroxypropylamino]pyrimidin-4-yl)-N-H-imidazole (H6.3.1)

An analogous reaction to that described in example H1.1.1, but starting with G6.3 gave H6.3.1 in 4% yield.
MS: M=530 (API+)

Example H6.3.2

2-(2,6-dichloro-4-hydroxymethylphenyl)-4-(3-methoxymethoxyphenyl)-5-(2-[2-hydroxyethyl-amino]pyrimidin-4-yl)-N-H-imidazole (H6.3.2)

An analogous reaction to that described in example H1.1.1, but starting with G6.3 and 2-aminoethanol gave H6.3.2 in 9% yield.
MS: M=516 (API+)

Example H6.3.3

2-(2,6-dichloro-4-hydroxymethylphenyl)-4-(3-methoxymethoxyphenyl)-5-(2-[3-methoxypropyl-amino]pyrimidin-4-yl-N-H-imidazole (H6.3.3)

An analogous reaction to that described in example H1.1.1, but starting with G6.3 and 3-methoxy-propylamine gave H6.3.3 in 8% yield.
MS: M=544 (API+)

Example H6.3.4

2-(2,6-dichloro-4-hydroxymethylphenyl)-4-(3-methoxymethoxyphenyl)-5-(2-[2-methoxyethyl-amino]pyrimidin-4-yl-N-H-imidazole (H6.3.4)

An analogous reaction to that described in example H1.1.1, but starting with G6.3 and 2-methoxy-ethylamine gave H6.3.4 in 4% yield.
MS: M=530 (API+)

Example H6.3.5

(rac)-2-(2,6-dichloro-4-hydroxymethylphenyl)-4-(3-methoxymethoxyphenyl)-5-(2-[2,3-dihydroxypropyl-amino]-pyrimidin-4-yl-N-H-imidazole (H6.3.5)

An analogous reaction to that described in example H1.1.1, but starting with G6.3 and 2,3-dihydroxypropylamine gave H6.3.5 in 7% yield.
MS: M=546 (API+)

Example H6.4.1

2-(2,6-dichloro-4-[2-hydroxyethoxy]phenyl)-4-(3-methoxymethoxyphenyl)-5-(2-[3-hydroxypropyl-amino]pyrimidin-4-yl)-N-H-imidazole (H6.4.1)

An analogous reaction to that described in example H1.1.1, but starting with G6.5 gave H6.4.1 in 57% yield.
MS: M=560 (API+)

Example H6.4.2

2-(2,6-dichloro-4-[2-hydroxyethoxy]phenyl)-4-(3-methoxymethoxyphenyl)-5-(2-[2-hydroxyethyl-amino]pyrimidin-4-yl)-N-H-imidazole (H6.4.2)

An analogous reaction to that described in example H1.1.1, but starting with G6.5 and 2-aminoethanol gave H6.4.2 in 48% yield.
MS: M=546 (API+)

Example H6.4.3

2-(2,6-dichloro-4-[2-hydroxyethoxy]phenyl)-4-(3-methoxymethoxyphenyl)-5-(2-[3-methoxypropyl-amino]pyrimidin-4-yl-N-H-imidazole (H6.4.3)

An analogous reaction to that described in example H1.1.1, but starting with G6.5 and 3-methoxy-propylamine gave H6.4.3 in 65% yield.
MS: M=574 (API+)

Example H6.4.4

2-(2,6-dichloro-4-[2-hydroxyethoxy]phenyl)-4-(3-methoxymethoxyphenyl)-5-(2-[2-methoxyethyl-amino]pyrimidin-4-yl-N-H-imidazole (H6.4.4)

An analogous reaction to that described in example H1.1.1, but starting with G6.5 and 2-methoxy-ethylamine gave H6.4.4 in 59% yield.
MS: M=560 (API+)

Example H6.4.5

2-(2,6-dichloro-4-[2-hydroxyethoxy]phenyl)-4-(3-methoxymethoxyphenyl)-5-(2-[2,3-dihydroxypropyl-amino]-pyrimidin-4-yl-N-H-imidazole (H6.4.5)

Example H6.5.1

2-(2,6-dichloro-4-[carboxymethoxy]phenyl)-4-(3-methoxymethoxyphenyl)-5-(2-[3-hydroxypropyl-amino]pyrimidin-4-yl)-N-H-imidazole (H6.5.1)

An analogous reaction to that described in example H1.1.1, but starting with G6.6 gave H6.5.1 in 65% yield.
MS: M=574 (API+)

Example H6.5.2

2-(2,6-dichloro-4-[carboxymethoxy]phenyl)-4-(3-methoxymethoxyphenyl)-5-(2-[2-hydroxyethyl-amino]pyrimidin-4-yl)-N-H-imidazole (H6.5.2)

An analogous reaction to that described in example H1.1.1, but starting with G6.6 and 2-aminoethanol gave H6.5.2 in 70% yield.
MS: M=560 (API+)

Example H6.5.3

2-(2,6-dichloro-4-[carboxymethoxy]phenyl)-4-(3-methoxymethoxyphenyl)-5-(2-[3-methoxypropyl-amino]pyrimidin-4-yl-N-H-imidazole (H6.5.3)

An analogous reaction to that described in example H1.1.1, but starting with G6.6 and 3-methoxy-propylamine gave H6.6.3 in 24% yield.

MS: M=588 (API+)

Example H6.5.4

2-(2,6-dichloro-4-[carboxymethoxy]phenyl)-4-(3-methoxymethoxyphenyl)-5-(2-[2-methoxyethyl-amino]pyrimidin-4-yl-N-H-imidazole (H6.5.4)

An analogous reaction to that described in example H1.1.1, but starting with G6.6 and 2-methoxy-ethylamine gave H6.5.4 in 61% yield.

MS: M=574 (API+)

Example H6.5.5

(rac)-2-(2,6-dichloro-4-[carboxymethoxy]phenyl)-4-(3-methoxymethoxyphenyl)-5-(2-[2,3-dihydroxypropyl-amino]-pyrimidin-4-yl-N-H-imidazole (H6.3.5)

Example H6.6.1

2-(2,6-dichloro-4-(2,2-dimethyl-[1,3]-dioxolane-4-ylmethoxy)phenyl)-4-(3-methoxymethoxyphenyl)-5-(2-[3-hydroxypropyl-amino]pyrimidin-4-yl)-N-H-imidazole (H6.6.1)

Example H6.6.2

2-(2,6-dichloro-4-(2,2-dimethyl-[1,3]-dioxolane-4-ylmethoxy)phenyl)-4-(3-methoxymethoxyphenyl)-5-(2-[2-hydroxyethyl-amino]pyrimidin-4-yl)-N-H-imidazole (H6.6.2)

Example H6.6.3

2-(2,6-dichloro-4-(2,2-dimethyl-[1,3]-dioxolane-4-ylmethoxy)phenyl)-4-(3-methoxy-methoxyphenyl)-5-(2-[3-methoxypropyl-amino]pyrimidin-4-yl)-N-H-imidazole (H6.6.3)

Example H6.6.4

2-(2,6-dichloro-4-(2,2-dimethyl-[1,3]-dioxolane-4-ylmethoxy)phenyl)-4-(3-methoxy-methoxyphenyl)-5-(2-[2-methoxyethylamino]pyrimidin-4-yl)-N-H-imidazole (H6.6.4)

Example H6.6.5

2-(2,6-dichloro-4-(2,2-dimethyl-[1,3]-dioxolane-4-ylmethoxy)phenyl)-4-(3-methoxy-methoxyphenyl)-5-(2-[2,3-dihydroxypropyl-amino]pyrimidin-4-yl)-N-H-imidazole (H6.6.5)

Example H6.7.1

2-(2,6-dichloro-4-(2,3-dihydroxypropoxy)phenyl)-4-(3-methoxymethoxyphenyl)-5-(2-[3-hydroxypropyl-amino]pyrimidin-4-yl)-N-H-imidazole (H6.7.1)

Example H6.7.2

2-(2,6-dichloro-4-(2,3-dihydroxypropoxy)phenyl)-4-(3-methoxymethoxyphenyl)-5-(2-[2-hydroxyethyl-amino]pyrimidin-4-yl)-N-H-imidazole (H6.7.2)

Example H6.7.3

2-(2,6-dichloro-4-(2,3-dihydroxypropoxy)phenyl)-4-(3-methoxymethoxyphenyl)-5-(2-[3-methoxypropyl-amino]pyrimidin-4-yl)-N-H-imidazole (H6.7.3)

Example H6.7.4

2-(2,6-dichloro-4-(2,3-dihydroxypropoxy)phenyl)-4-(3-methoxymethoxyphenyl)-5-(2-[2-methoxyethyl-amino]pyrimidin-4-yl)-N-H-imidazole (H6.7.4)

Example H6.7.5

2-(2,6-dichloro-4-(2,3-dihydroxypropoxy)phenyl)-4-(3-methoxymethoxyphenyl)-5-(2-[2,3-dihydroxypropylamino]pyrimidin-4-yl)-N-H-imidazole (H6.7.5)

Example H6.8.1

2-(2,6-dichloro-4-(dimethylphoshinoylmethoxy)phenyl)-4-(3-methoxymethoxyphenyl)-5-(2-[3-hydroxypropyl-amino]pyrimidin-4-yl)-N-H-imidazole (H6.8.1)

An analogous reaction to that described in example H1.1.1, but starting with G6.9 gave H6.8.1

MS: M=606 (API+)

Example H6.8.2

2-(2,6-dichloro-4-(dimethylphoshinoylmethoxy)phenyl)-4-(3-methoxymethoxyphenyl)-5-(2-[2-hydroxyethylamino]pyrimidin-4-yl)-N-H-imidazole (H6.8.2)

Example H6.8.3

2-(2,6-dichloro-4-(dimethylphoshinoylmethoxy)phenyl)-4-(3-methoxymethoxyphenyl)-5-(2-[3-methoxypropylamino]pyrimidin-4-yl)-N-H-imidazole (H6.8.3)

Example H6.8.4

2-(2,6-dichloro-4-(dimethylphoshinoylmethoxy)phenyl)-4-(3-methoxymethoxyphenyl)-5-(2-[2-methoxypropylamino]pyrimidin-4-yl)-N-H-imidazole (H6.8.4)

Example H6.8.5

2-(2,6-dichloro-4-(dimethylphoshinoylmethoxy)
phenyl)-4-(3-methoxymethoxyphenyl)-5-(2-[2,3-
dihydroxypropylamino]pyrimidin-4-yl)-N-H-
imidazole (H6.8.5)

Example H6.9.1

2-(2,6-dichloro-4-methanesulfinylphenyl)-4-(3-
methoxymethoxyphenyl)-5-(2-[3-hydroxypropyl-
amino]pyrimidin-4-yl)-N-H-imidazole (H6.9.1)

An analogous reaction to that described in example H1.1.1, but starting with G6.10 gave H6.9.1 in 28% yield. MS: M=562 (API+)

Example H6.9.2

2-(2,6-dichloro-4-methanesulfinylphenyl)-4-(3-
methoxymethoxyphenyl)-5-(2-[2-hydroxyethyl-
amino]pyrimidin-4-yl)-N-H-imidazole (H6.9.2)

Example H6.9.3

2-(2,6-dichloro-4-methanesulfinylphenyl)-4-(3-
methoxymethoxyphenyl)-5-(2-[3-methoxypropyl-
amino]pyrimidin-4-yl)-N-H-imidazole (H6.9.3)

Example H6.9.4

2-(2,6-dichloro-4-methanesulfinylphenyl)-4-(3-
methoxymethoxyphenyl)-5-(2-[2-methoxyethyl-
amino]pyrimidin-4-yl)-N-H-imidazole (H6.9.4)

Example H6.9.5

2-(2,6-dichloro-4-methanesulfinylphenyl)-4-(3-
methoxymethoxyphenyl)-5-(2-[2,3-
dihydroxypropyl-amino]pyrimidin-4-yl)-N-H-
imidazole (H6.9.5)

Example H7.1.1

2-(2,6-dichlorophenyl)-4-(3-[4'-cyanobenzyloxy]
phenyl)-5-(2-[3-hydroxypropylamino]pyrimidin-4-
yl)-N-H-imidazole (H7.1.1)

Example H7.1.2

2-(2,6-dichlorophenyl)-4-(3-[4'-cyanobenzyloxy]
phenyl)-5-(2-[2-hydroxyethylamino]-pyrimidin-4-
yl)-N-H-imidazole (H7.1.2)

Example H7.1.3

2-(2,6-dichlorophenyl)-4-(3-[4'-cyanobenzyloxy]
phenyl)-5-(2-[3-methoxypropylamino]pyrimidin-4-
yl)-N-H-imidazole (H7.1.3)

Example H7.1.4

2-(2,6-dichlorophenyl)-4-(3-[4'-cyanobenzyloxy]
phenyl)-5-(2-[2-merhoxyethylamino]pyrimidin-4-
yl)-N-H-imidazole (H7.1.4)

Example H7.1.5

2-(2,6-dichlorophenyl)-4-(3-[4'-cyanobenzyloxy]
phenyl)-5-(2-[2,3-dihydroxypropyl-amino]
pyrimidin-4-yl)-N-H-imidazole (H7.1.5)

Example H7.2.1

2-(2,6-dichloro-4-hydroxyphenyl)-4-(3-[4'-
cyanobenzyloxy]phenyl)-5-(2-[3-
hydroxypropylamino]pyrimidin-4-yl)-N-H-
imidazole (H7.2.1)

Example H7.2.2

2-(2,6-dichloro-4-hydroxyphenyl)-4-(3-[4'-
cyanobenzyloxy]phenyl)-5-(2-[2-
hydroxyethylamino]pyrimidin-4-yl)-N-H-imidazole
(H7.2.2)

Example H7.2.3

2-(2,6-dichloro-4-hydroxyphenyl)-4-(3-[4'-
cyanobenzyloxy]phenyl)-5-(2-[3-
methoxypropylamino]pyrimidin-4-yl)-N-H-
imidazole (H7.2.3)

Example H7.2.4

2-(2,6-dichloro-4-hydroxyphenyl)-4-(3-[4'-
cyanobenzyloxy]phenyl)-5-(2-[2-
methoxyethylamino]pyrimidin-4-yl)-N-H-imidazole
(H7.2.4)

Example H7.2.5

2-(2,6-dichloro-4-hydroxyphenyl)-4-(3-[4'-
cyanobenzyloxy]phenyl)-5-(2-[2,3-
dihydroxypropylamino]pyrimidin-4-yl)-N-H-
imidazole (H7.2.5)

Example H7.3.1

2-(2,6-dichloro-4-hydroxymethylphenyl)-4-(3-[4'-
cyanobenzyloxy]phenyl)-5-(2-[3-
hydroxypropylamino]pyrimidin-4-yl)-N-H-
imidazole (H7.3.1)

Example H7.3.2

2-(2,6-dichloro-4-hydroxymethylphenyl)-4-(3-[4'-
cyanobenzyloxy]phenyl)-5-(2-[2-
hydroxyethylamino]pyrimidin-4-yl)-N-H-imidazole
(H7.3.2)

Example H7.3.3

2-(2,6-dichloro-4-hydroxymethylphenyl)-4-(3-[4'-
cyanobenzyloxy]phenyl)-5-(2-[3-
methoxypropylamino]pyrimidin-4-yl)-N-H-
imidazole (H7.3.3)

Example H7.3.4

2-(2,6-dichloro-4-hydroxymethylphenyl)-4-(3-[4'-cyanobenzyloxy]phenyl)-5-(2-[2-methoxyethylamino]pyrimidin-4-yl)-N-H-imidazole (H7.3.4)

Example H7.3.5

2-(2,6-dichloro-4-hydroxymethylphenyl)-4-(3-[4'-cyanobenzyloxy]phenyl)-5-(2-[2,3-dihydroxypropylamino]pyrimidin-4-yl)-N-H-imidazole (H7.3.5)

Example H7.4.1

2-(2,6-dichloro-4-(2-hydroxyethoxy)phenyl)-4-(3-[4'-cyanobenzyloxy]phenyl)-5-(2-[3-hydroxypropylamino]pyrimidin-4-yl)-N-H-imidazole (H7.4.1)

An analogous reaction to that described in example H1.1.1, but starting with G7.4 gave H7.4.1.
MS: M=631 (API+)

Example H7.4.2

2-(2,6-dichloro-4-(2-hydroxyethoxy)phenyl)-4-(3-[4'-cyanobenzyloxy]phenyl)-5-(2-[2-hydroxyethylamino]pyrimidin-4-yl)-N-H-imidazole (H7.4.2)

Example H7.4.3

2-(2,6-dichloro-4-(2-hydroxyethoxy)phenyl)-4-(3-[4'-cyanobenzyloxy]phenyl)-5-(2-[3-methoxypropylamino]pyrimidin-4-yl)-N-H-imidazole (H7.4.3)

Example H7.4.4

2-(2,6-dichloro-4-(2-hydroxyethoxy)phenyl)-4-(3-[4'-cyanobenzyloxy]phenyl)-5-(2-[2-methoxyethylamino]pyrimidin-4-yl)-N-H-imidazole (H7.4.4)

Example H7.4.5

2-(2,6-dichloro-4-(2-hydroxyethoxy)phenyl)-4-(3-[4'-cyanobenzyloxy]phenyl)-5-(2-[2,3-dihydroxypropylamino]pyrimidin-4-yl)-N-H-imidazole (H7.4.5)

Example H8.1.1

2-(2,6-dichlorophenyl)-4-(3-[4'-chlorobenzyloxy]phenyl)-5-(2-[3-hydroxypropylamino]pyrimidin-4-yl)-N-H-imidazole (H8.1.1)

An analogous reaction to that described in example H1.1.1, but starting with G8.1 gave H8.1.1 in 77% yield.
MS: M=582 (API+)

Example H8.1.2

2-(2,6-dichlorophenyl)-4-(3-[4'-chlorobenzyloxy]phenyl)-5-(2-[2-hydroxyethylamino]pyrimidin-4-yl)-N-H-imidazole (H8.1.2)

An analogous reaction to that described in example H1.1.1, but starting with G8.1 and 2-aminoethanol gave H8.1.2 in 46% yield.
MS: M=568 (API+)

Example H8.1.3

2-(2,6-dichlorophenyl)-4-(3-[4'-chlorobenzyloxy]phenyl)-5-(2-[3-methoxypropylamino]pyrimidin-4-yl)-N-H-imidazole (H8.1.3)

An analogous reaction to that described in example H1.1.1, but starting with G8.1 and 3-methoxy-1-aminopropane gave H8.1.3 in 84% yield.
MS: M=596 (API+)

Example H8.1.4

2-(2,6-dichlorophenyl)-4-(3-[4'-chlorobenzyloxy]phenyl)-5-(2-[2-methoxyethylamino]pyrimidin-4-yl)-N-H-imidazole (H8.1.4)

An analogous reaction to that described in example H1.1.1, but starting with G8.1 and 2-methoxy-1-aminoethane gave H8.1.4 in 83% yield.
MS: M=582 (API+)

Example H8.1.5

(rac)-2-(2,6-dichlorophenyl)-4-(3-benzyloxyphenyl)-5-(2-[2,3-dihydroxypropylamino]pyrimidin-4-yl)-N-H-imidazole (H8.1.5)

An analogous reaction to that described in example H1.1.1, but starting with G8.1 and (rac)-2,3-dihydroxypropyl-amine gave H8.1.5 in 46% yield.
MS: M=598 (API+)

Example H8.2.1

2-(2,6-dichloro-4-hydroxyphenyl)-4-(3-[4'-chlorobenzyloxy]phenyl)-5-(2-[3-hydroxypropyl-amino]pyrimidin-4-yl)-N-H-imidazole (H8.2.1)

An analogous reaction to that described in example H1.1.1, but starting with G8.2 gave H8.2.1 in 68% yield.
MS: M=596 (API+)

Example H8.2.2

2-(2,6-dichloro-4-hydroxyphenyl)-4-(3-[4'-chlorobenzyloxy]phenyl)-5-(2-[2-hydroxyethyl-amino]pyrimidin-4-yl)-N-H-imidazole (H8.2.2)

An analogous reaction to that described in example H1.1.1, but starting with G8.2 and 2-aminoethanol gave H8.2.2 in 60% yield.
MS: M=584 (API+)

Example H8.2.3

2-(2,6-dichloro-4-hydroxyphenyl)-4-(3-[4'-chlorobenzyloxy]phenyl)-5-(2-[3-methoxypropyl-amino]pyrimidin-4-yl)-N-H-imidazole (H8.2.3)

An analogous reaction to that described in example H1.1.1, but starting with G8.2 and 3-methoxy-1-aminopropane gave H8.2.3 in 67% yield.
MS: M=612 (API+)

Example H8.2.4

2-(2,6-dichloro-4-hydroxyphenyl)-4-(3-[4'-chlorobenzyloxy]phenyl)-5-(2-[2-methoxyethyl-amino]pyrimidin-4-yl)-N-H-imidazole (H8.2.4)

An analogous reaction to that described in example H1.1.1, but starting with G8.2 and 2-methoxy-1-aminoethane gave H8.2.4 in 64% yield.
MS: M=598 (API+)

Example H8.2.5

(rac)-2-(2,6-dichloro-4-hydroxyphenyl)-4-(3-[4'-chlorobenzyloxy]phenyl)-5-(2-[2,3-dihydroxypropyl-amino]pyrimidin-4-yl)-N-H-imidazole (H8.2.5)

An analogous reaction to that described in example H1.1.1, but starting with G8.2 and (rac)-2,3-dihydroxypropyl-amine gave H8.2.5 in 11% yield.
MS: M=612 (API+)

Example H8.3.1

2-(2,6-dichloro-4-hydroxymethylphenyl)-4-(3-[4'-chlorobenzyloxy]phenyl)-5-(2-[3-hydroxypropyl-amino]pyrimidin-4-yl)-N-H-imidazole (H8.3.1)

Example H8.3.2

2-(2,6-dichloro-4-hydroxymethylphenyl)-4-(3-[4'-chlorobenzyloxy]phenyl)-5-(2-[2-hydroxyethyl-amino]pyrimidin-4-yl)-N-H-imidazole (H8.3.2)

Example H8.3.3

2-(2,6-dichloro-4-hydroxymethylphenyl)-4-(3-[4'-chlorobenzyloxy]phenyl)-5-(2-[3-methoxypropyl-amino]pyrimidin-4-yl)-N-H-imidazole (H8.3.3)

Example H8.3.4

2-(2,6-dichloro-4-hydroxymethylphenyl)-4-(3-[4'-chlorobenzyloxy]phenyl)-5-(2-[2-methoxyethyl-amino]pyrimidin-4-yl)-N-H-imidazole (H8.3.4)

Example H8.3.5

2-(2,6-dichloro-4-hydroxymethylphenyl)-4-(3-[4'-chlorobenzyloxy]phenyl)-5-(2-[2,3-dihydroxypropyl-amino]pyrimidin-4-yl)-N-H-imidazole (H8.3.5)

Example H9.1.1

2-(2,6-dichlorophenyl)-4-(3-[4'-methoxybenzyloxy]phenyl)-5-(2-[3-hydroxypropyl-amino]pyrimidin-4-yl)-N-H-imidazole (H9.1.1)

Example H9.1.2

2-(2,6-dichlorophenyl)-4-(3-[4'-methoxybenzyloxy]phenyl)-5-(2-[2-hydroxyethylamino]pyrimidin-4-yl)-N-H-imidazole (H9.1.2)

Example H9.1.3

2-(2,6-dichlorophenyl)-4-(3-[4'-methoxybenzyloxy]phenyl)-5-(2-[3-methoxypropyl-amino]pyrimidin-4-yl)-N-H-imidazole (H9.1.3)

Example H9.1.4

2-(2,6-dichlorophenyl)-4-(3-[4'-methoxybenzyloxy]phenyl)-5-(2-[2-methoxyethyl-amino]pyrimidin-4-yl)-N-H-imidazole (H9.1.4)

Example H9.1.5

2-(2,6-dichlorophenyl)-4-(3-[4'-methoxybenzyloxy]phenyl)-5-(2-[2,3-dihydroxypropyl-amino]pyrimidin-4-yl)-N-H-imidazole (H9.1.5)

Example H9.2.1

2-(2,6-dichloro-4-hydroxyphenyl)-4-(3-[4'-methoxybenzyloxy]phenyl)-5-(2-[3-hydroxypropylamino]pyrimidin-4-yl)-N-H-imidazole (H9.2.1)

Example H9.2.2

2-(2,6-dichloro-4-hydroxyphenyl)-4-(3-[4'-methoxybenzyloxy]phenyl)-5-(2-[2-hydroxyethylamino]pyrimidin-4-yl)-N-H-imidazole (H9.2.2)

Example H9.2.3

2-(2,6-dichloro-4-hydroxyphenyl)-4-(3-[4'-methoxybenzyloxy]phenyl)-5-(2-[3-methoxypropylamino]pyrimidin-4-yl)-N-H-imidazole (H9.2.3)

Example H9.2.4

2-(2,6-dichloro-4-hydroxyphenyl)-4-(3-[4'-methoxybenzyloxy]phenyl)-5-(2-[2-methoxyethylamino]pyrimidin-4-yl)-N-H-imidazole (H9.2.4)

Example H9.2.5

2-(2,6-dichloro-4-hydroxyphenyl)-4-(3-[4'-methoxybenzyloxy]phenyl)-5-(2-[2,3-dihydroxypropylamino]pyrimidin-4-yl)-N-H-imidazole (H9.2.5)

Example H9.3.1

2-(2,6-dichloro-4-hydroxymethylphenyl)-4-(3-[4'-methoxybenzyloxy]phenyl)-5-(2-[3-hydroxypropylamino]pyrimidin-4-yl)-N-H-imidazole (H9.3.1)

Example H9.3.2

2-(2,6-dichloro-4-hydroxymethylphenyl)-4-(3-[4'-methoxybenzyloxy]phenyl)-5-(2-[2-hydroxyethylamino]pyrimidin-4-yl)-N-H-imidazole (H9.3.2)

Example H9.3.3

2-(2,6-dichloro-4-hydroxymethylphenyl)-4-(3-[4'-methoxybenzyloxy]phenyl)-5-(2-[3-methoxypropylamino]pyrimidin-4-yl)-N-H-imidazole (H9.3.3)

Example H9.3.4

2-(2,6-dichloro-4-hydroxymethylphenyl)-4-(3-[4'-methoxybenzyloxy]phenyl)-5-(2-[2-methoxyethylamino]pyrimidin-4-yl)-N-H-imidazole (H9.3.4)

Example H9.3.5

2-(2,6-dichloro-4-hydroxymethylphenyl)-4-(3-[4'-methoxybenzyloxy]phenyl)-5-(2-[2,3-dihydroxypropylamino]pyrimidin-4-yl)-N-H-imidazole (H9.3.5)

Example H10.1.1

2-(2,6-dichlorophenyl)-4-(3-allyloxyphenyl)-5-(2-[3-hydroxypropylamino]pyrimidin-4-yl)-N-H-imidazole (H10.1.1)

An analogous reaction to that described in example H1.1.1, but starting with G10.1 gave H10.1.1 in 55% yield.
MS: M=496 (API+)

Example H10.1.2

2-(2,6-dichlorophenyl)-4-(3-allyloxyphenyl)-5-(2-[2-hydroxyethylamino]pyrimidin-4-yl)-N-H-imidazole (H10.1.2)

An analogous reaction to that described in example H1.1.1, but starting with G10.1 and 2-aminoethanol gave H10.1.2 in 99% yield.
MS: M=482 (API+)

Example H10.1.3

2-(2,6-dichlorophenyl)-4-(3-allyloxyphenyl)-5-(2-[3-methoxypropyl-amino]pyrimidin-4-yl)-N-H-imidazole (H10.1.3)

Example H10.1.4

2-(2,6-dichlorophenyl)-4-(3-allyloxyphenyl)-5-(2-[2-methoxyethylamino]pyrimidin-4-yl)-N-H-imidazole (H10.1.4)

Example H10.1.5

2-(2,6-dichlorophenyl)-4-(3-allyloxyphenyl)-5-(2-[2,3-dihydroxypropylamino]pyrimidin-4-yl)-N-H-imidazole (H10.1.5)

Example H10.2.1

2-(2,6-dichloro-4-hydroxyphenyl)-4-(3-allyloxyphenyl)-5-(2-[3-hydroxypropylamino]pyrimidin-4-yl)-N-H-imidazole (H10.2.1)

Example H10.2.2

2-(2,6-dichloro-4-hydroxyphenyl)-4-(3-allyloxyphenyl)-5-(2-[2-hydroxyethylamino]-pyrimidin-4-yl)-N-H-imidazole (H10.2.2)

Example H10.2.3

2-(2,6-dichloro-4-hydroxyphenyl)-4-(3-allyloxyphenyl)-5-(2-[3-methoxypropylamino]pyrimidin-4-yl)-N-H-imidazole (H10.2.3)

Example H10.2.4

2-(2,6-dichloro-4-hydroxyphenyl)-4-(3-allyloxyphenyl)-5-(2-[2-methoxyethylamino]pyrimidin-4-yl)-N-H-imidazole (H10.2.4)

Example H10.2.5

2-(2,6-dichloro-4-hydroxyphenyl)-4-(3-allyloxyphenyl)-5-(2-[2,3-dihydroxypropyl-amino]pyrimidin-4-yl)-N-H-imidazole (H10.2.5)

Example H10.3.1

2-(2,6-dichloro-4-hydroxmethylphenyl)-4-(3-allyloxyphenyl)-5-(2-[3-hydroxypropyl-amino]pyrimidin-4-yl)-N-H-imidazole (H10.3.1)

Example H10.3.2

2-(2,6-dichloro-4-hydroxymethylphenyl)-4-(3-allyloxyphenyl)-5-(2-[2-hydroxyethyl-amino]pyrimidin-4-yl)-N-H-imidazole (H10.3.2)

Example H10.3.3

2-(2,6-dichloro-4-hydroxymethylphenyl)-4-(3-allyloxyphenyl)-5-(2-[3-methoxypropyl-amino]pyrimidin-4-yl)-N-H-imidazole (H10.3.3)

Example H10.3.4

2-(2,6-dichloro-4-hydroxymethylphenyl)-4-(3-allyloxyphenyl)-5-(2-[2-methoxyethyl-amino]pyrimidin-4-yl)-N-H-imidazole (H10.3.4)

Example H10.3.5

2-(2,6-dichloro-4-hydroxymethylphenyl)-4-(3-allyloxyphenyl)-5-(2-[2,3-dihydroxy-propylamino]pyrimidin-4-yl)-N-H-imidazole (H10.3.5)

Example H11.1.1

2-(2,6-dichlorophenyl)-4-(4-chlorophenyl)-5-(2-[3-hydroxypropylamino]pyrimidin-4-yl)-N-H-imidazole (H11.1.1)

An analogous reaction to that described in example H1.1.1, but starting with G11.1 gave H11.1.1 in 49% yield.
MS: M=476 (API+)

Example H11.1.2

2-(2,6-dichlorophenyl)-4-(4-chlorophenyl)-5-(2-[2-hydroxyethylamino]pyrimidin-4-yl)-N-H-imidazole (H11.1.2)

An analogous reaction to that described in example H1.1.1, but starting with G11.1 and 2-aminoethanol gave H11.1.2 in 40% yield, m.p. 129–134° C.
MS: M=462 (API+)

Example H11.1.3

2-(2,6-dichlorophenyl)-4-(4-chlorophenyl)-5-(2-[3-methoxypropylamino]pyrimidin-4-yl)-N-H-imidazole (H11.1.3)

An analogous reaction to that described in example H1.1.1, but starting with G11.1 and 3-methoxy-1-aminopropane gave H11.1.3 in 73% yield.
MS: M=490 (API+)

Example H11.1.4

2-(2,6-dichlorophenyl)-4-(4-chlorophenyl)-5-(2-[2-methoxyethylamino]pyrimidin-4-yl)-N-H-imidazole (H11.1.4)

An analogous reaction to that described in example H1.1.1, but starting with G11.1 and 2-methoxy-1-aminoethane gave H11.1.4 in 73% yield.
MS: M=476 (API+)

Example H11.1.5

(rac)-2-(2,6-dichlorophenyl)-4-(4-chlorophenyl)-5-(2-[2,3-dihydroxypropylamino]pyrimidin-4-yl)-N-H-imidazole (H11.1.5)

An analogous reaction to that described in example H1.1.1, but starting with G11.1 and (rac)-2,3-dihydroxypropylamine gave H11.1.5 in 86% yield.
MS: M=492 (+)

Example H11.1.6

(R)-2-(2,6-dichlorophenyl)-4-(4-chlorophenyl)-5-(2-[2,3-dihydroxypropylamino]pyrimidin-4-yl)-N-H-imidazole (H11.1.6)

An analogous reaction to that described in example H1.1.1, but starting with G11.1 and (R)-2,3-dihydroxypropylamine gave H11.1.6 in 47% yield.
MS: M=492 (API+)

Example H11.1.7

(S)-2-(2,6-dichlorophenyl)-4-(3-bromophenyl)-5-(2-[2,3-dihydroxypropylamino]pyrimidin-4-yl)-N-H-imidazole (H11.1.7)

Example H11.1.8

2-(2,6-dichlorophenyl)-4-(4-chlorophenyl)-5-(2-[4-hydroxybutylamino]pyrimidin-4-yl)-N-H-imidazole (H11.1.8)

An analogous reaction to that described in example H1.1.1, but starting with G11.1 and 4-amino-1-butanol gave H11.1.8 in 52% yield.
MS: M=488 (API+)

Example H11.1.9

2-(2,6-dichlorophenyl)-4-(4-chlorophenyl)-5-(2-[5-hydroxypentylamino]pyrimidin-4-yl)-N-H-imidazole (H11.1.9)

An analogous reaction to that described in example H1.1.1, but starting with G11.1 and 5-amino-1-pentanol gave H11.1.9 in 53% yield, m.p. 188–194° C.
MS: M=504 (API+)

Example H11.1.10

2-(2,6-dichlorophenyl)-4-(4-chlorophenyl)-5-(2-[3-hydroxy-2,2-dimethylpropylamino]pyrimidin-4-yl)-N-H-imidazole (H11.1.10)

An analogous reaction to that described in example H1.1.1, but starting with G11.1 and 3-amino-2,2-dimethyl-1-propanol gave H11.1.10 in 73% yield.
MS: M=504 (API+)

Example H11.1.1

(rac)-2-(2,6-dichlorophenyl)-4-(4-chlorophenyl)-5-(2-[3-hydroxybutylamino]pyrimidin-4-yl)-N-H-imidazole (H11.1.11)

An analogous reaction to that described in example H1.1.1, but starting with G11.1 and (rac)-4-amino-2-butanol gave H1.1.1 in 53% yield.
MS: M=490 (API+)

Example H11.1.12

(rac)-2-(2,6-dichlorophenyl)-4-(4-chlorophenyl)-5-(2-[3-hydroxy-1-phenylpropylamino]pyrimidin-4-yl)-N-H-imidazole (H11.1.12)

An analogous reaction to that described in example H1.1.1, but starting with G11.1 and (rac)-3-amino-3-phenyl-1-propanol gave H11.1.12 in 31% yield, m.p. 129–134° C.
MS: M=552 (API+)

Example H11.1.13

2-(2,6-dichlorophenyl)-4-(4-chlorophenyl)-5-(2-[2-tert-butyloxyethylamino]pyrimidin-4-yl)-N-H-imidazole (H11.1.13)

An analogous reaction to that described in example H1.1.1, but starting with G11.1 and 2-tert-butyloxyethylamine gave H11.1.13 in 84% yield.

MS: M=518 (API+)

Example H11.1.14

2-(2,6-dichlorophenyl)-4-(4-chlorophenyl)-5-(2-aminopyrimidin-4-yl)-N-H-imidazole (H11.1.14)

A solution of 30 mg (0.06 mmol) G11.1 were placed in an autoclave and 10 ml liquid ammonia was added. After 20 h at 40° C. the solvent was removed and the residue was purified by column chromatography on SiGel (dichloromethane/methanolic ammonia 95:5). Yield: 17 mg (64%) H11.1.14.

MS: M=418 (API+)

Example H11.1.15

2-(2,6-dichlorophenyl)-4-(4-chlorophenyl)-5-(2-[(2-tert-butyloxycarbonylaminoethyl)amino]pyrimidin-4-yl)-N-H-imidazole (H11.1.15)

An analogous reaction to that described in example H1.1.1, but starting with G11.1 and N-BOC-ethylendiamine gave H11.1.15 in 81% yield.

MS: M=561 (API+)

Example H11.1.16

2-(2,6-dichlorophenyl)-4-(4-chlorophenyl)-5-(2-[(3-tert-butyloxycarbonylaminopropyl)amino]pyrimidin-4-yl)-N-H-imidazole (H11.1.16)

An analogous reaction to that described in example H1.1.1, but starting with G11.1 and N-BOC-1,3-diaminopropane gave H11.1.16 in 81% yield.

MS: M=575 (API+)

Example H11.1.17

2-(2,6-dichlorophenyl)-4-(4-chlorophenyl)-5-(2-[(4-tert-butyloxycarbonylaminobutyl)amino]pyrimidin-4-yl)-N-H-imidazole (H11.1.17)

An analogous reaction to that described in example H1.1.1, but starting with G11.1 and N-BOC-1,4-diaminobutane gave H11.1.17 in 75% yield.

MS: M=589 (API+)

Example H11.1.18

2-(2,6-dichlorophenyl)-4-(4-chlorophenyl)-5-(2-[(2 aminoethyl)amino]pyrimidin-4-yl)-N-H-imidazole (H11.1.18)

From H11.1.15 by treatment with trifluoroacetic acid at room temperature overnight. Isolated as trifluoroacetate in 63% yield.

MS: M=461 (API+)

Example H11.1.19

2-(2,6-dichlorophenyl)-4-(4-chlorophenyl)-5-(2-[(3-aminopropyl)amino]pyrimidin-4-yl)-N-H-imidazole (H11.1.19)

An analogous reaction to that described in example H11.1.18, but starting with H11.1.16 gave H11.1.19 in 82% yield.

MS: M=475 (API+)

Example H11.1.20

2-(2,6-dichlorophenyl)-4-(4-chlorophenyl)-5-(2-[(4-aminobutyl)amino]pyrimidin-4-yl)-N-H-imidazole (H11.1.20)

An analogous reaction to that described in example H11.1.18, but starting with H11.1.17 gave H11.1.20 in 26% yield.

MS: M=489 (API+)

Example H11.1.21

2-(2,6-dichlorophenyl)-4-(4-chlorophenyl)-5-(2-[(2-N,N-dimethylaminoethyl)-amino]pyrimidin-4-yl)-N-H-imidazole (H11.1.21)

An analogous reaction to that described in example H1.1.1, but starting with G11.1 and N,N-dimethylethylendiamine gave H11.1.21 in 69% yield, m.p. 109–119° C.

MS: M=489 (API+)

Example H11.1.22

2-(2,6-dichlorophenyl)-4-(4-chlorophenyl)-5-(2-[(3-N,N-dimethylaminopropyl)amino]pyrimidin-4-yl)-N-H-imidazole (H11.1.22)

An analogous reaction to that described in example H1.1.1, but starting with G11.1 and N,N-dimethyl-1,3-diaminopropane gave H11.1.22 in 67% yield, m.p. 98–113° C.

MS: M=503 (API+)

Example H11.1.23

2-(2,6-dichlorophenyl)-4-(4-chlorophenyl)-5-(2-[3-(pyrrolidin-1-yl)propylamino]pyrimidin-4-yl)-N-H-imidazole (H11.1.23)

An analogous reaction to that described in example H1.1.1, but starting with G11.1 and 1-(3-aminopropyl)pyrrolidine gave H11.1.23 in 55% yield.

MS: M=529 (API+)

Example H11.1.24

2-(2,6-dichlorophenyl)-4-(4-chlorophenyl)-5-(2-[3-(morpholin-4-yl)propylamino]pyrimidin-4-yl)-N-H-imidazole (H11.1.24)

An analogous reaction to that described in example H1.1.1, but starting with G11.1 and 4-(3-aminopropyl)morpholine gave H11.1.24 in 55% yield.

MS: M=545 (API+)

Example H11.1.25

2-(2,6-dichlorophenyl)-4-(4-chlorophenyl)-5-(2-[3-(4-methylpiperazin-1-yl)propylamino]pyrimidin-4-yl)-N-H-imidazole (H11.1.25)

An analogous reaction to that described in example H1.1.1, but starting with G11.1 and 1-(3-aminopropyl)-4-methylpiperazine gave H11.1.25 in 69% yield, m.p. 113–118° C.

MS: M=558 (API+)

Example H11.1.26

2-(2,6-dichlorophenyl)-4-(4-chlorophenyl)-5-(2-[(tert-butylcarboxy)methylamino]pyrimidin-4-yl)-N-H-imidazole (H11.1.26)

An analogous reaction to that described in example H1.1.1, but starting with G11.1 and tert-butyl 2-aminoacetate gave H11.1.26 in 18% yield.

MS: M=532 (API+)

Example H11.1.27

2-(2,6-dichlorophenyl)-4-(4-chlorophenyl)-5-(2-[2-(tert-butylcarboxy)ethylamino]pyrimidin-4-yl)-N-H-imidazole (H11.1.27)

An analogous reaction to that described in example H1.1.1, but starting with G11.1 and tert-butyl 3-aminopropionate gave H11.1.27 in 62% yield.

MS: M=546 (API+)

Example H11.1.28

2-(2,6-dichlorophenyl)-4-(4-chlorophenyl)-5-(2-[3-(tert-butylcarboxy)propylamino]-pyrimidin-4-yl)-N-H-imidazole (H11.1.28)

An analogous reaction to that described in example H1.1.1, but starting with G11.1 and tert-butyl 4-aminobutyrate gave H11.1.28 in 76% yield.

MS: M=560 (API+)

Example H11.1.29

2-(2,6-dichlorophenyl)-4-(4-chlorophenyl)-5-(2-[(R)-1-(tert-butylcarboxy)propylamino]-pyrimidin-4-yl)-N-H-imidazole (H11.1.29)

An analogous reaction to that described in example H1.1.1, but starting with G11.1 and tert-butyl 2-aminobutyrate gave H11.1.29 in 47% yield.

MS: M=560 (API+)

Example H11.1.30

2-(2,6-dichlorophenyl)-4-(4-chlorophenyl)-5-(2-[carboxymethylamino]pyrimidin-4-yl)-N-H-imidazole (H11.1.30)

From H11.1.26 with trifluoroacetic acid at room temperature overnight.

MS: M=476 (API+)

Example H11.1.31

2-(2,6-dichlorophenyl)-4-(4-chlorophenyl)-5-(2-[2-carboxyethylamino]pyrimidin-4-yl)-N-H-imidazole (H11.1.31)

An analogous reaction to that described in example H11.1.29, but starting with H11.1.27 gave H11.1.31.

MS: M=490 (API+)

Example H11.1.32

2-(2,6-dichlorophenyl)-4-(4-chlorophenyl)-5-(2-[3-carboxypropylamino]pyrimidin-4-yl)-N-H-imidazole (H11.1.32)

An analogous reaction to that described in example H11.1.29, but starting with H11.1.28 gave H11.1.32.

MS: M=504 (API+)

Example H11.1.33

2-(2,6-dichlorophenyl)-4-(4-chlorophenyl)-5-(2-[(R)-1-carboxypropylamino]pyrimidin-4-yl)-N-H-imidazole (H11.1.33)

An analogous reaction to that described in example H11.1.29, but starting with H11.1.29 gave H11.1.29.

MS: M=504 (API+)

Example H11.1.34

2-(2,6-dichlorophenyl)-4-(4-chlorophenyl)-5-(2-[2-(2-aminoethoxy)ethylamino]-pyrimidin-4-yl)-N-H-imidazole (H11.1.34)

An analogous reaction to that described in example H1.1.1, but starting with G11.1 and 2-(2-aminoethoxy)ethylamine gave H11.1.34 in 30% yield.

MS: M=505 (API+)

Example H11.1.35

2-(2,6-dichlorophenyl)-4-(4-chlorophenyl)-5-(2-[2-(2-N,N-dimethylaminopropoxy)-propylamino]-pyrimidin-4-yl)-N-H-imidazole (H11.1.35)

An analogous reaction to that described in example H1.1.1, but starting with G11.1 and 2-(2-N,N-dimethylaminoethoxy)ethylamine gave H11.1.35 in 76% yield.

MS: M=561 (API+)

Example H11.1.36

2-(2,6-dichlorophenyl)-4-(4-chlorophenyl)-5-(2-[2-(2-N,N-dimethylaminoethyl)-thioethylamino]-pyrimidin-4-yl)-N-H-imidazole (H11.1.36)

An analogous reaction to that described in example H1.1.1, but starting with G11.1 and 2-(2-N,N-dimethylaminoethyl)thioethylamine gave H11.1.36 in 79% yield.

MS: M=549 (API+), 547 (API−)

Example H11.1.37

2-(2,6-dichlorophenyl)-4-(4-chlorophenyl)-5-(2-[2-(3-N,N-dimethylaminopropyl)-thioethylamino]-pyrimidin-4-yl)-N-H-imidazole (H11.1.37)

An analogous reaction to that described in example H1.1.1, but starting with G11.1 and 2-(3-N,N-dimethylaminopropyl)thioethylamine gave H11.1.37 in 87% yield.

MS: M=563 (API+), 561 (API−)

Example H11.1.38

2-(2,6-dichlorophenyl)-4-(4-chlorophenyl)-5-(2-[3-(2-N,N-dimethylaminoethyl)-thiopropylamino]-pyrimidin-4-yl)-N-H-imidazole (H11.1.38)

An analogous reaction to that described in example H1.1.1, but starting with G11.1 and 3-(2-N,N-dimethylaminoethyl)thiopropylamine gave H11.1.38 in 62% yield.

MS: M=563 (API+), 561 (API−)

Example H11.1.39

2-(2,6-dichlorophenyl)-4-(4-chlorophenyl)-5-(2-[3-(3-N,N-dimethylaminopropyl)thiopropylamino]-pyrimidin-4-yl)-N-H-imidazole (H11.1.39)

An analogous reaction to that described in example H1.1.1, but starting with G11.1 and 3-(3-N,N-dimethylaminopropyl)thiopropylamine gave H11.1.39 in 68% yield.

MS: M=577 (API+), 575 (API−)

Example H11.1.40

2-(2,6-dichlorophenyl)-4-(4-chlorophenyl)-5-(2-[(3-methylthiophen-2-yl)methylamino]-pyrimidin-4-yl)-N-H-imidazole (H11.1.40)

An analogous reaction to that described in example H1.1.1, but starting with G11.1 and 2-aminomethyl-3-methylthiophene gave H11.1.40 in 40% yield.

MS: M=528 (API+)

Example H11.1.41

2-(2,6-dichlorophenyl)-4-(4-chlorophenyl)-5-(2-[2-(thiophen-2-yl)ethylamino]pyrimidin-4-yl)-N-H-imidazole (H11.1.41)

An analogous reaction to that described in example H1.1.1, but starting with G11.1 2-(thiophen-2-yl)ethylamine gave H11.1.41 in 74% yield.

MS: M=528 (API+)

Example H11.1.42

2-(2,6-dichlorophenyl)-4-(4-chlorophenyl)-5-(2-[(furan-3-yl)methylamino]-pyrimidin-4-yl)-N-H-imidazole (H11.1.42)

An analogous reaction to that described in example H1.1.1, but starting with G11.1 3-aminomethylfurane gave H11.1.42 in 45% yield.

MS: M=498 (API+)

Example H11.1.43

2-(2,6-dichlorophenyl)-4-(4-chlorophenyl)-5-(2-[2-(1,2,4-triazol-1-yl)ethylamino]-pyrimidin-4-yl)-N-H-imidazole (H11.1.43)

An analogous reaction to that described in example H1.1.1, but starting with G11.1 2-(1,2,4-triazol-1-yl) ethylamine gave H11.1.43 in 49% yield.

MS: M=513 (API+)

Example H11.1.44

2-(2,6-dichlorophenyl)-4-(4-chlorophenyl)-5-(2-[3-(1,2,4-triazol-3-yl)propylamino]-pyrimidin-4-yl)-N-H-imidazole (H11.1.44)

An analogous reaction to that described in example H1.1.1, but starting with G11.1 3-(1,2,4-triazol-3-yl) propylamine gave H11.1.44 in 81% yield.

MS: M=527 (API+)

Example H11.2.1

2-(2,6-dichloro-4-hydroxyphenyl)-4-(4-chlorophenyl)-5-(2-[3-hydroxypropylamino] pyrimidin-4-yl)-N-H-imidazole (H11.2.1)

Example H11.2.2

2-(2,6-dichloro-4-hydroxyphenyl)-4-(4-chlorophenyl)-5-(2-[2-hydroxyethyl-amino] pyrimidin-4-yl)-N-H-imidazole (H11.2.2)

Example H11.2.3

2-(2,6-dichloro-4-hydroxyphenyl)-4-(4-chlorophenyl)-5-(2-[3-methoxypropylamino] pyrimidin-4-yl)-N-H-imidazole (H11.2.3)

Example H11.2.4

2-(2,6-dichloro-4-hydroxyphenyl)-4-(4-chlorophenyl)-5-(2-[2-methoxyethylamino] pyrimidin-4-yl)-N-H-imidazole (H11.2.4)

Example H11.2.5

2-(2,6-dichloro-4-hydroxyphenyl)-4-(4-chlorophenyl)-5-(2-[2,3-dihydroxypropylamino] pyrimidin-4-yl)-N-H-imidazole (H11.2.5)

Example H11.3.1

2-(2,6-dichloro-4-hydroxymethylphenyl)-4-(4-chlorophenyl)-5-(2-[3-hydroxypropylamino] pyrimidin-4-yl)-N-H-imidazole (H11.3.1)

An analogous reaction to that described in example H1.1.1, but starting with G11.3 gave H11.3.1 in 13% yield.

MS: M=506 (API+), 504 (API−)

Example H11.3.2

2-(2,6-dichloro-4-hydroxymethylphenyl)-4-(4-chlorophenyl)-5-(2-[2-hydroxyethylamino]pyrimidin-4-yl)-N-H-imidazole (H11.3.2)

Example H11.3.3

2-(2,6-dichloro-4-hydroxymethylphenyl)-4-(4-chlorophenyl)-5-(2-[3-methoxypropylamino]pyrimidin-4-yl)-N-H-imidazole (H11.3.3)

Example H11.3.4

2-(2,6-dichloro-4-hydroxymethylphenyl)-4-(4-chlorophenyl)-5-(2-[2-methoxyethylamino]pyrimidin-4-yl)-N-H-imidazole (H11.3.4)

Example H11.3.5

2-(2,6-dichloro-4-hydroxymethylphenyl)-4-(4-chlorophenyl)-5-(2-[2,3-dihydroxypropylamino]pyrimidin-4-yl)-N-H-imidazole (H11.3.5)

Example H12.1.1

2-(2,6-dichlorophenyl)-4-(4-fluorophenyl)-5-(2-[3-hydroxypropylamino]pyrimidin-4-yl)-N-H-imidazole (H12.1.1)

Example H12.1.2

2-(2,6-dichlorophenyl)-4-(4-fluorophenyl)-5-(2-[2-hydroxyethylamino]pyrimidin-4-yl)-N-H-imidazole (H12.1.2)

Example H12.1.3

2-(2,6-dichlorophenyl)-4-(4-fluorophenyl)-5-(2-[3-methoxypropylamino]-pyrimidin-4-yl)-N-H-imidazole (H12.1.3)

Example H12.1.4

2-(2,6-dichlorophenyl)-4-(4-fluorophenyl)-5-(2-[2-methoxyethylamino]pyrimidin-4-yl)-N-H-imidazole (H12.1.4)

Example H12.1.5

2-(2,6-dichlorophenyl)-4-(4-fluorophenyl)-5-(2-[2,3-dihydroxypropylamino]-pyrimidin-4-yl)-N-H-imidazole (H12.1.5)

Example H12.2.1

2-(2,6-dichloro-4-hydroxyphenyl)-4-(4-fluorophenyl)-5-(2-[3-hydroxypropylamino]pyrimidin-4-yl)-N-H-imidazole (H12.2.1)

Example H12.2.2

2-(2,6-dichloro-4-hydroxyphenyl)-4-(4-fluorophenyl)-5-(2-[2-hydroxyethylamino]pyrimidin-4-yl)-N-H-imidazole (H12.2.2)

Example H12.2.3

2-(2,6-dichloro-4-hydroxyphenyl)-4-(4-fluorophenyl)-5-(2-[3-methoxypropylamino]pyrimidin-4-yl)-N-H-imidazole (H12.2.3)

Example H12.2.4

2-(2,6-dichloro-4-hydroxyphenyl)-4-(4-fluorophenyl)-5-(2-[2-methoxyethylamino]pyrimidin-4-yl)-N-H-imidazole (H12.2.4)

Example H12.2.5

2-(2,6-dichloro-4-hydroxyphenyl)-4-(4-fluorophenyl)-5-(2-[2,3-dihydroxypropylamino]pyrimidin-4-yl)-N-H-imidazole (H12.2.5)

Example H12.3.1

2-(2,6-dichloro-4-hydroxymethylphenyl)-4-(4-fluorophenyl)-5-(2-[3-hydroxypropylamino]pyrimidin-4-yl)-N-H-imidazole (H12.3.1)

Example H12.3.2

2-(2,6-dichloro-4-hydroxymethylphenyl)-4-(4-fluorophenyl)-5-(2-[2-hydroxyethylamino]pyrimidin-4-yl)-N-H-imidazole (H12.3.2)

Example H2.3.3

2-(2,6-dichloro-4-hydroxymethylphenyl)-4-(4-fluorophenyl)-5-(2-[3-methoxypropylamino]pyrimidin-4-yl)-N-H-imidazole (H12.3.3)

Example H12.3.4

2-(2,6-dichloro-4-hydroxymethylphenyl)-4-(4-fluorophenyl)-5-(2-[2-methoxyethylamino]pyrimidin-4-yl)-N-H-imidazole (H12.3.4)

Example H12.3.5

2-(2,6-dichloro-4-hydroxymethylphenyl)-4-(4-fluorophenyl)-5-(2-[2,3-dihydroxypropylamino]pyrimidin-4-yl)-N-H-imidazole (H12.3.5)

Example H13.1.1

2-(2,6-dichlorophenyl)-4-(4-chloro-3-methoxyphenyl)-5-(2-[3-hydroxypropylamino]pyrimidin-4-yl)-N-H-imidazole (H13.1.1)

Example H3.1.2

2-(2,6-dichlorophenyl)-4-(4-chloro-3-methoxyphenyl)-5-(2-[2-hydroxyethylamino]pyrimidin-4-yl)-N-H-imidazole (H13.1.2)

Example H13.1.3

2-(2,6-dichlorophenyl)-4-(4-chloro-3-methoxyphenyl)-5-(2-[3-methoxypropylamino]pyrimidin-4-yl)-N-H-imidazole (H13.1.3)

Example H13.1.4

2-(2,6-dichlorophenyl)-4-(4-chloro-3-methoxyphenyl)-5-(2-[2-methoxyethylamino]pyrimidin-4-yl)-N-H-imidazole (H13.1.4)

Example H13.1.5

2-(2,6-dichlorophenyl)-4-(4-chloro-3-methoxyphenyl)-5-(2-[2,3-dihydroxypropylamino]pyrimidin-4-yl)-N-H-imidazole (H13.1.5)

Example H13.2.1

2-(2,6-dichloro-4-hydroxyphenyl)-4-(4-chloro-3-methoxyphenyl)-5-(2-[3-hydroxypropylamino]pyrimidin-4-yl)-N-H-imidazole (H13.2.1)

Example H13.2.2

2-(2,6-dichloro-4-hydroxyphenyl)-4-(4-chloro-3-methoxyphenyl)-5-(2-[2-hydroxyethylamino]pyrimidin-4-yl)-N-H-imidazole (H13.2.2)

Example H13.2.3

2-(2,6-dichloro-4-hydroxyphenyl)-4-(4-chloro-3-methoxyphenyl)-5-(2-[3-methoxypropylamino]pyrimidin-4-yl)-N-H-imidazole (H13.2.3)

Example H13.2.4

2-(2,6-dichloro-4-hydroxyphenyl)-4-(4-chloro-3-methoxyphenyl)-5-(2-[2-methoxyethylamino]pyrimidin-4-yl)-N-H-imidazole (H13.2.4)

Example H13.2.5

2-(2,6-dichloro-4-hydroxyphenyl)-4-(4-chloro-3-methoxyphenyl)-5-(2-[2,3-dihydroxypropylamino]pyrimidin-4-yl)-N-H-imidazole (H13.2.5)

Example H13.3.1

2-(2,6-dichloro-4-hydroxymethylphenyl)-4-(4-chloro-3-methoxyphenyl)-5-(2-[3-hydroxypropylamino]pyrimidin-4-yl)-N-H-imidazole (H13.3.1)

Example H13.3.2

2-(2,6-dichloro-4-hydroxymethylphenyl)-4-(4-chloro-3-methoxyphenyl)-5-(2-[2-hydroxyethylamino]pyrimidin-4-yl)-N-H-imidazole (H13.3.2)

Example H13.3.3

2-(2,6-dichloro-4-hydroxymethylphenyl)-4-(4-chloro-3-methoxyphenyl)-5-(2-[3-methoxypropylamino]pyrimidin-4-yl)-N-H-imidazole (H13.3.3)

Example H13.3.4

2-(2,6-dichloro-4-hydroxymethylphenyl)-4-(4-chloro-3-methoxyphenyl)-5-(2-[2-methoxyethylamino]pyrimidin-4-yl)-N-H-imidazole (H13.3.4)

Example H13.3.5

2-(2,6-dichloro-4-hydroxyphenyl)-4-(4-chloro-3-methoxyphenyl)-5-(2-[2,3-dihydroxypropylamino]pyrimidin-4-yl)-N-H-imidazole (H13.3.5)

Example H14.1.1

2-(2,6-dichlorophenyl)-4-(3-benzyloxy-4-fluorophenyl)-5-(2-[3-hydroxypropylamino]pyrimidin-4-yl)-N-H-imidazole (H14.1.1)

An analogous reaction to that described in example H1.1.1, but starting with G14.1 gave H14.1.1 in 68% yield.
MS: M=564 (API+)

Example H14.1.2

2-(2,6-dichlorophenyl)-4-(3-benzyloxy-4-fluorophenyl)-5-(2-[2-hydroxyethylamino]-pyrimidin-4-yl)-N-H-imidazole (H14.1.2)

An analogous reaction to that described in example H1.1.1, but starting with G14.1 and 2-aminoethanol gave H14.1.2 in 73% yield.
MS: M=550 (API+)

Example H14.1.3

2-(2,6-dichlorophenyl)-4-(3-benzyloxy-4-fluorophenyl)-5-(2-[3-methoxypropylamino]-pyrimidin-4-yl)-N-H-imidazole (H14.1.3)

An analogous reaction to that described in example H1.1.1, but starting with G14.1 and 3-methoxy-1-aminopropane gave H14.1.3 in 80% yield.
MS: M=578 (API+)

Example H14.1.4

2-(2,6-dichlorophenyl)-4-(3-benzyloxy-4-fluorophenyl)-5-(2-[2-methoxyethylamino]pyrimidin-4-yl)-N-H-imidazole (H14.1.4)

An analogous reaction to that described in example H1.1.1, but starting with G14.1 and 2-methoxy-1-aminoethane gave H14.1.4 in 67% yield.
MS: M=564 (API+)

Example H14.1.5

(rac)-2-(2,6-dichlorophenyl)-4-(3-benzyloxy-4-fluorophenyl)-5-(2-[2,3-dihydroxypropyl-amino]pyrimidin-4-yl)-N-H-imidazole (H14.1.5)

An analogous reaction to that described in example H1.1.1, but starting with G14.1 and (rac)-2,3-dihydroxypropyl-amine gave H14.1.5 in 58% yield.
MS: M=580 (API+)

Example H14.2.1

2-(2,6-dichloro-4-hydroxyphenyl)-4-(3-benzyloxy-4-fluorophenyl)-5-(2-[3-hydroxypropyl-amino]pyrimidin-4-yl)-N-H-imidazole (H14.2.1)

An analogous reaction to that described in example H1.1.1, but starting with G14.2 gave H14.2.1 in 58% yield.
MS: M=580 (API+)

Example H14.2.2

2-(2,6-dichloro-4-hydroxyphenyl)-4-(3-benzyloxy-4-fluorophenyl)-5-(2-[2-hydroxyethylamino]pyrimidin-4-yl)-N-H-imidazole (H14.2.2)

An analogous reaction to that described in example H1.1.1, but starting with G14.2 and 2-aminoethanol gave H14.2.2 in 76% yield.
MS: M=566 (API+)

Example H14.2.3

2-(2,6-dichloro-4-hydroxyphenyl)-4-(3-benzyloxy-4-fluorophenyl)-5-(2-[3-methoxypropyl-amino]pyrimidin-4-yl)-N-H-imidazole (H14.2.3)

An analogous reaction to that described in example H1.1.1, but starting with G14.2 and 3-methoxy-1-aminopropane gave H14.2.3 in 77% yield.
MS: M=594 (API+)

Example H14.2.4

2-(2,6-dichloro-4-hydroxyphenyl)-4-(3-benzyloxy-4-fluorophenyl)-5-(2-[2-methoxyethyl-amino]pyrimidin-4-yl)-N-H-imidazole (H14.2.4)

An analogous reaction to that described in example H1.1.1, but starting with G14.2 and 2-methoxy-1-aminoethane gave H14.2.4 in 53% yield.
MS: M=580 (API+)

Example H14.2.5

(rac)-2-(2,6-dichloro-4-hydroxyphenyl)-4-(3-benzyloxy-4-fluorophenyl)-5-(2-[2,3-dihydroxypropyl-amino]pyrimidin-4-yl)-N-H-imidazole (H14.2.5)

An analogous reaction to that described in example H1.1.1, but starting with G14.2 and (rac)-2,3-dihydroxypropyl-amine gave H14.2.5 in 48% yield.
MS: M=596 (API+)

Example H14.3.1

2-(2,6-dichloro-4-hydroxymethylphenyl)-4-(3-benzyloxy-4-fluorophenyl)-5-(2-[3-hydroxypropyl-amino]pyrimidin-4-yl)-N-H-imidazole (H14.3.1)

An analogous reaction to that described in example H1.1.1, but starting with G14.3 gave H14.3.1 in 53% yield.
MS: M=594 (API+)

Example H14.3.2

2-(2,6-dichloro-4-hydroxymethylphenyl)-4-(3-benzyloxy-4-fluorophenyl)-5-(2-[2-hydroxyethyl-amino]pyrimidin-4-yl)-N-H-imidazole (H14.3.2)

An analogous reaction to that described in example H1.1.1, but starting with G14.3 and 2-aminoethanol gave H14.3.2 in 39% yield.
MS: M=580 (API+)

Example H14.3.3

2-(2,6-dichloro-4-hydroxymethylphenyl)-4-(3-benzyloxy-4-fluorophenyl)-5-(2-[3-methoxypropyl-amino]pyrimidin-4-yl)-N-H-imidazole (H14.3.3)

An analogous reaction to that described in example H1.1.1, but starting with G14.3 and 3-methoxy-1-aminopropane gave H14.3.3 in 24% yield.
MS: M=608 (API+)

Example H14.3.4

2-(2,6-dichloro-4-hydroxymethylphenyl)-4-(3-benzyloxy-4-fluorophenyl)-5-(2-[2-methoxyethyl-amino]pyrimidin-4-yl)-N-H-imidazole (H14.3.4)

An analogous reaction to that described in example H1.1.1, but starting with G14.3 and 2-methoxy-1-aminoethane gave H14.3.4 in 60% yield.
MS: M=594 (API+)

Example H14.3.5

(rac)-2-(2,6-dichloro-4-hydroxymethylphenyl)-4-(3-benzyloxy-4-fluorophenyl)-5-(2-[2,3-dihydroxypropylamino]pyrimidin-4-yl)-N-H-imidazole (H14.3.5)

An analogous reaction to that described in example H1.1.1, but starting with G14.3 and (rac)-2,3-dihydroxypropyl-amine gave H14.3.5 in 49% yield.
MS: M=610 (API+)

Example H15.1.1

2-(2,6-dichlorophenyl)-4-(3-benzyloxy-4-methylphenyl)-5-(2-[3-hydroxypropylamino]-pyrimidin-4-yl)-N-H-imidazole (H15.1.1)

Example H15.1.2

2-(2,6-dichlorophenyl)-4-(3-benzyloxy-4-methylphenyl)-5-(2-[2-hydroxyethylamino]-pyrimidin-4-yl)-N-H-imidazole (H15.1.2)

Example H5.1.3

2-(2,6-dichlorophenyl)-4-(3-benzyloxy-4-methylphenyl)-5-(2-[3-methoxypropylamino]pyrimidin-4-yl)-N-H-imidazole (H15.1.3)

Example H5.1.4

2-(2,6-dichlorophenyl)-4-(3-benzyloxy-4-methylphenyl)-5-(2-[2-methoxypropylamino]pyrimidin-4-yl)-N-H-imidazole (H15.1.4)

Example H15.1.5

2-(2,6-dichlorophenyl)-4-(3-benzyloxy-4-methylphenyl)-5-(2-[2,3-dihydroxypropylamino]pyrimidin-4-yl)-N-H-imidazole (H15.1.5)

Example H15.2.1

2-(2,6-dichloro-4-hydroxyphenyl)-4-(3-benzyloxy-4-methylphenyl)-5-(2-[3-hydroxypropyl-amino]pyrimidin-4-yl)-N-H-imidazole (H15.2.1)

An analogous reaction to that described in example H1.1.1, but starting with G15.2 gave H15.2.1 in 71% yield.
MS: M=576 (API+)

Example H15.2.2

2-(2,6-dichloro-4-hydroxyphenyl)-4-(3-benzyloxy-4-methylphenyl)-5-(2-[2-hydroxyethylamino]pyrimidin-4-yl)-N-H-imidazole (H15.2.2)

An analogous reaction to that described in example H1.1.1, but starting with G15.2 and 2-aminoethanol gave H15.2.2 in 76% yield.
MS: M=562 (API+)

Example H15.2.3

2-(2,6-dichloro-4-hydroxyphenyl)-4-(3-benzyloxy-4-methylphenyl)-5-(2-[3-methoxypropyl-amino]pyrimidin-4-yl)-N-H-imidazole (H15.2.3)

An analogous reaction to that described in example H1.1.1, but starting with G15.2 and 3-methoxy-1-aminopropane gave H15.2.3 in 70% yield.
MS: M=590 (API+)

Example H15.2.4

2-(2,6-dichloro-4-hydroxyphenyl)-4-(3-benzyloxy-4-methylphenyl)-5-(2-[2-methoxyethyl-amino]pyrimidin-4-yl)-N-H-imidazole (H15.2.4)

An analogous reaction to that described in example H1.1.1, but starting with G15.2 and 2-methoxy-1-aminoethane gave H15.2.4 in 70% yield.
MS: M=576 (API+)

Example H15.2.5

(rac)-2-(2,6-dichloro-4-hydroxyphenyl)-4-(3-benzyloxy-4-methylphenyl)-5-(2-[2,3-dihydroxypropyl-amino]pyrimidin-4-yl)-N-H-imidazole (H15.2.5)

An analogous reaction to that described in example H1.1.1, but starting with G15.2 and (rac)-2,3-dihydroxypropyl-amine gave H15.2.5 in 53% yield.
MS: M=592 (API+)

Example H15.3.1

2-(2,6-dichloro-4-hydroxymethylphenyl)-4-(3-benzyloxy-4-methylphenyl)-5-(2-[3-hydroxypropyl-amino]pyrimidin-4-yl)-N-H-imidazole (H15.3.1)

An analogous reaction to that described in example H1.1.1, but starting with G15.3 gave H15.3.1 in 58% yield.
MS: M=590 (API+)

Example H15.3.2

2-(2,6-dichloro-4-hydroxymethylphenyl)-4-(3-benzyloxy-4-methylphenyl)-5-(2-[2-hydroxyethyl-amino]pyrimidin-4-yl)-N-H-imidazole (H15.3.2)

An analogous reaction to that described in example H1.1.1, but starting with G15.3 and 2-aminoethanol gave H15.3.2 in 45% yield.
MS: M=576 (API+)

Example H15.3.3

2-(2,6-dichloro-4-hydroxymethylphenyl)-4-(3-benzyloxy-4-methylphenyl)-5-(2-[3-methoxypropyl-amino]pyrimidin-4-yl)-N-H-imidazole (H15.3.3)

An analogous reaction to that described in example H1.1.1, but starting with G15.3 and 3-methoxy-1-aminopropane gave H15.3.3 in 27% yield.
MS: M=604 (API+)

Example H15.3.4

2-(2,6-dichloro-4-hydroxymethylphenyl)-4-(3-benzyloxy-4-methylphenyl)-5-(2-[2-methoxyethyl-amino]pyrimidin-4-yl)-N-H-imidazole (H15.3.4)

An analogous reaction to that described in example H1.1.1, but starting with G15.3 and 2-methoxy-1-aminoethane gave H15.3.4 in 60% yield.
MS: M=590 (API+)

Example H15.3.5

(rac)-2-(2,6-dichloro-4-hydroxymethylphenyl)-4-(3-benzyloxy-4-methylphenyl)-5-(2-[2,3-dihydroxypropylamino]pyrimidin-4-yl)-N-H-imidazole (H15.3.5)

An analogous reaction to that described in example H1.1.1, but starting with G15.3 and (rac)-2,3-dihydroxypropyl-amine gave H15.3.5 in 55% yield.
MS: M=606 (API+)

Example H16.1.1

2-(2,6-dichlorophenyl)-4-(3-methylthiophenyl)-5-(2-[3-hydroxypropylamino]-pyrimidin-4-yl)-N-H-imidazole (H16.1.1)

Example H16.1.2

2-(2,6-dichlorophenyl)-4-(3-methylthiophenyl)-5-(2-[2-hydroxyethylamino]-pyrimidin-4-yl)-N-H-imidazole (H16.1.2)

Example H16.1.3

2-(2,6-dichlorophenyl)-4-(3-methylthiophenyl)-5-(2-[3-methoxypropylamino]pyrimidin-4-yl)-N-H-imidazole (H16.1.3)

Example H16.1.4

2-(2,6-dichlorophenyl)-4-(3-methylthiophenyl)-5-(2-[2-methoxyethylamino]-pyrimidin-4-yl)-N-H-imidazole (H16.1.4)

Example H16.1.5

(rac)-2-(2,6-dichlorophenyl)-4-(3-methylthiophenyl)-5-(2-[2,3-dihydroxypropylamino]pyrimidin-4-yl)-N-H-imidazole (H16.1.5)

Example H16.2.1

2-(2,6-dichloro-4-hydroxyphenyl)-4-(3-methylthiophenyl)-5-(2-[3-hydroxypropylamino]pyrimidin-4-yl)-N-H-imidazole (H16.2.1)

Example H16.2.2

2-(2,6-dichloro-4-hydroxyphenyl)-4-(3-methylthiophenyl)-5-(2-[2-hydroxyethylamino]pyrimidin-4-yl)-N-H-imidazole (H16.2.2)

Example H16.2.3

2-(2,6-dichloro-4-hydroxyphenyl)-4-(3-methylthiophenyl)-5-(2-[3-methoxypropylamino]pyrimidin-4-yl)-N-H-imidazole (H16.2.3)

Example H16.2.4

2-(2,6-dichloro-4-hydroxyphenyl)-4-(3-methylthiophenyl)-5-(2-[2-methoxyethylamino]pyrimidin-4-yl)-N-H-imidazole (H16.2.4)

Example H16.2.5

(rac)-2-(2,6-dichloro-4-hydroxyphenyl)-4-(3-methylthiophenyl)-5-(2-[2,3-dihydroxypropyl-amino]pyrimidin-4-yl)-N-H-imidazole (H16.2.5)

Example H16.3.1

2-(2,6-dichloro-4-hydroxymethylphenyl)-4-(3-methylthiophenyl)-5-(2-[3-hydroxypropylamino]pyrimidin-4-yl)-N-H-imidazole (H16.3.1)

Example H16.3.2

2-(2,6-dichloro-4-hydroxymethylphenyl)-4-(3-methylthiophenyl)-5-(2-[2-hydroxyethylamino]pyrimidin-4-yl)-N-H-imidazole (H16.3.2)

Example H16.3.3

2-(2,6-dichloro-4-hydroxymethylphenyl)-4-(3-methylthiophenyl)-5-(2-[3-methoxypropylamino]pyrimidin-4-yl)-N-H-imidazole (H16.3.3)

Example H16.3.4

2-(2,6-dichloro-4-hydroxymethylphenyl)-4-(3-methylthiophenyl)-5-(2-[2-methoxyethylamino]pyrimidin-4-yl)-N-H-imidazole (H16.3.4)

Example H16.3.5

(rac)-2-(2,6-dichloro-4-hydroxymethylphenyl)-4-(3-methylthiophenyl)-5-(2-[2,3-dihydroxypropyl-amino]pyrimidin-4-yl)-N-H-imidazole (H16.3.5)

Example H17.1.1

2-(2,6-dichlorophenyl)-4-(3-acetylenylphenyl)-5-(2-[3-hydroxypropylamino]-pyrimidin-4-yl)-N-H-imidazole (H17.1.1)

An analogous reaction to that described in example H1.1.1, but starting with G17.1 gave H17.1.1 in 69% yield.
MS: M=464 (API+)

Example H17.1.2

2-(2,6-dichlorophenyl)-4-(3-acetylenylphenyl)-5-(2-[2-hydroxyethylamino]pyrimidin-4-yl)-N-H-imidazole (H17.1.2)

An analogous reaction to that described in example H1.1.1, but starting with G17.1 and 2-aminoethanol gave H17.1.2 in 71% yield.
MS: M=450 (API+)

Example H17.1.3

2-(2,6-dichlorophenyl)-4-(3-acetylenylphenyl)-5-(2-[3-methoxypropylamino]-pyrimidin-4-yl)-N-H-imidazole (H17.1.3)

Example H17.1.4

2-(2,6-dichlorophenyl)-4-(3-acetylenylphenyl)-5-(2-[2-methoxyethylamino]-pyrimidin-4-yl)-N-H-imidazole (H17.1.4)

Example H17.1.5

(R)-2-(2,6-dichlorophenyl)-4-(3-acetylenylphenyl)-5-(2-[2,3-dihydroxypropylamino]pyrimidin-4-yl)-N-H-imidazole (H17.1.5)

An analogous reaction to that described in example H1.1.1, but starting with G17.1 and (R)-2,3-dihydroxypropylamine gave H17.1.5 in 61% yield.
MS: M=480 (API+)

Example H17.1.6

(S)-2-(2,6-dichlorophenyl)-4-(3-acetylenylphenyl)-5-(2-[2,3-dihydroxypropylamino]pyrimidin-4-yl)-N-H-imidazole (H17.1.6)

An analogous reaction to that described in example H1.1.1, but starting with G17.1 and (S)-2,3-dihydroxypropyl-amine gave H17.1.6 in 63% yield.
MS: M=480 (API+)

Example H17.2.1

2-(2,6-dichloro-4-hydroxyphenyl)-4-(3-acetylenylphenyl)-5-(2-[3-hydroxypropylamino]pyrimidin-4-yl)-N-H-imidazole (H17.2.1)

Example H17.2.2

2-(2,6-dichloro-4-hydroxyphenyl)-4-(3-acetylenylphenyl)-5-(2-[2-hydroxyethylamino]pyrimidin-4-yl)-N-H-imidazole (H17.2.2)

Example H17.2.3

2-(2,6-dichloro-4-hydroxyphenyl)-4-(3-acetylenylphenyl)-5-(2-[3-methoxypropylamino]pyrimidin-4-yl)-N-H-imidazole (H17.2.3)

Example H17.2.4

2-(2,6-dichloro-4-hydroxyphenyl)-4-(3-acetylenylphenyl)-5-(2-[2-metoxyethylamino]pyrimidin-4-yl)-N-H-imidazole (H17.2.4)

Example H17.2.5

2-(2,6-dichloro-4-hydroxyphenyl)-4-(3-acetylenylphenyl)-5-(2-[2,3-dihydroxypropylamino]pyrimidin-4-yl)-N-H-imidazole (H17.2.5)

Example H17.3.1

2-(2,6-dichloro-4-hydroxymethylphenyl)-4-(3-acetylenylphenyl)-5-(2-[3-hydroxypropylamino]pyrimidin-4-yl)-N-H-imidazole (H17.3.1)

Example H17.3.2

2-(2,6-dichloro-4-hydroxymethylphenyl)-4-(3-acetylenylphenyl)-5-(2-[2-hydroxyethylamino]pyrimidin-4-yl)-N-H-imidazole (H17.3.2)

Example H17.3.3

2-(2,6-dichloro-4-hydroxymethylphenyl)-4-(3-acetylenylphenyl)-5-(2-[3-methoxypropylamino]pyrimidin-4-yl)-N-H-imidazole (H17.3.3)

Example H17.3.4

2-(2,6-dichloro-4-hydroxymethylphenyl)-4-(3-acetylenylphenyl)-5-(2-[2-metoxyethylamino]pyrimidin-4-yl)-N-H-imidazole (H17.3.4)

Example H17.3.5

2-(2,6-dichloro-4-hydroxymethylphenyl)-4-(3-acetylenylphenyl)-5-(2-[2,3-dihydroxypropylamino]pyrimidin-4-yl)-N-H-imidazole (H17.3.5)

Example J c-met Autoactivation Kinase Assay (AKA)

Assay Principle

C-met is a typical tyrosine kinase which is involved in metastasis, proliferation/apoptosis and angiogenesis of tumors. The assay is an ELISA type assay measuring the phosphorylation of c-met using a phospho-tyrosine specific antibody. Cell lysate of human colon adenocarcinoma HT29 known for its high content of c-met is bound to the wells of a microtiterplate (MTP) via an anti-hHGF receptor antibody (anti-hHGFR). ATP-phosphorylation of c-met is detected in presence or absence of the test compounds by using an anti-phospho-tyrosine mouse IgG and a POD labeled goat anti-mouse IgG detection system. Using the classical POD substrate TMB, an absorption at 450 nm/620 nm is used to calculate enzymatic activity.

Materials:

Plates: 96-well polystyrene plates (NUNC) streptavidin-coated microtiter plates

Cell line/Lysate: HT29 (ATCC HTB-38), human colon adenocarcinoma (confluence: $2.5 \times 10^5$ cells/cm$^2$) are washed with PBS and incubated with Lysis buffer for 10 min on ice. Supernatent is collected and diluted with TBS. Lysate is shockfrozen in liquid nitrogen and stored at −80° C.)

Reagents (all working solutions are kept at 4° C., unless stated otherwise): anti-hHGFR detection stock solution: 50 µg/ml (R&D Systems, Cat.No. BAF 358) antibody final conc.: 1 µg/ml p-Tyr (PY99) mouse stock solution: 200 µg/ml (Santa Cruz Biotechnology, monoclonal IgG2b Cat.No. SC-7020) final conc.: 0.2 µg/ml goat-anti-mouse IgG: 2 ml (BIO RAD, Cat. No. 170-6516) (H+L)-HRP Conjugate; final conc.: 1:2000

Blocking Reagent: Roche Diagnostics GmbH, Cat.No. 1112589 for ELISA diluted 1:10 in TBS ATP: Adenosine-5'-triphosphate, stock solution 10 mM, stock solution 10 mM (Roche Diagnostics GmbH, Cat. No. 127531) final conc.: 40 µM TBS: Tris-buffered saline, 50 mM TRIS pH 7.5 (Roche Diagnostics GmbH, Cat.No. 708976), 150 mM NaCl (SIGMA, Cat.No. S-3014)

Wash buffer TBS-T: Tris-buffered saline, 50 mM TRIS pH7.5 150 mM NaCl, containing 0.5% Tween20

Kinase buffer: Tris-buffered saline, 50 mM TRIS pH7.5, 100 mM NaCl, 60 mM MgCl$_2$ (SIGMA Chemical Company, Cat.No. M-1028)

Lysis buffer: 50 mM TRIS pH7.5 containing 1% Nonidet P40 (Roche Diagnostics GmbH, Cat.No.1754599) 0.5% Deoxycholic acid (SIGMA Chemical Company, Cat.No. D-6750)

final conc.: 1 mM 1 mM PMSF stock solution 70 mM (Diagnostics GmbH, Cat. No.837091 40 µl/ml Complete (Roche Diagnostics GmbH, Cat.No. 1836145) Final conc.: 40 µl/ml TMB: Tetramethylbenzidin (Intergen Company, Cat.No. 91000)

Samples: 10 mM in DMSO (stored at −20° C.), thawed at room temperature

Procedure:
1. Add 50 µl of anti-hHGFR detection antibody in Blocking Reagent to assay plate (final conc. 1 µg/ml), incubate assay plate for 60 min at room temperature on a MTP shaker.
2. Remove anti-hHGFR detection antibody solution from assay plate.
3. Add 250 µl Blocking Reagent per well to assay plate, incubate assay plate for 20 h, at 4° C.
4. Remove Blocking Reagent from assay plate.
5. Add 50 µl of HT29 lysate, incubate assay plate for 180 min, at 4° C. on a MTP shaker.
6. Wash assay plate with 2×200 µl TBS buffer per well.
7. Add 40 µl of 0.2% DMSO in kinase buffer to assay plate.
8. Add 40 µl sample solution (dissolved in kinase buffer—final conc. 22.5 µM).

9. Disolute samples (1:3 ratio) in MTP.
10. Add 10 μl ATP disolved in kinase buffer (200 μM) to samples (final conc. 40 μM ATP) Positive control: add 40 μl kinase buffer plus 10 μl 200 μM ATP. Negative control: add 40 μl kinase buffer plus 10 μl kinase buffer without ATP. Incubate assay plate for 60 min at room temperature on a MTP shaker.
11. Wash assay plate with 2×200 μl TBS buffer and 2×200 μl Blocking Reagent per well.
12. Add 50 μl of P-Tyr (PY99) mouse monoclonal IgG$_{2b}$ in Blocking Reagent (final conc. 200 ng/ml) to assay plate, incubate assay plate over night at 4° C. on a MTP shaker.
13. Wash assay plate with 2×200 μl TBS buffer and 2×200 μl Blocking Reagent per well.
14. Add 50 μl of goat anti-mouse IgG (H+L)-HRP conjugate in Blocking Reagent (1:2000 ratio), incubate assay plate for 60 min at room temperature on a MTP shaker.
15. Wash assay plate with 6×200 μl TBS-T buffer per well.
16. Add 50 μl TMB solution, incubate for 30 min at room temperature on a MTP shaker, add 25 μl 1 M $H_2SO_4$.
17. Measure optical density (E) at 450 nm/620 nm.
18. Calculate % inhibition as:

$$1-[(E_{sample}-E_{negative\ control})/(E_{positive\ control}-E_{negative}\ control)\times 100]$$

Agents of the invention typically have $IC_{50}$ values for kinase inhibition in the range from about 1 nM to about 10 μM when tested in the above assay.

Example K

Tablet Formulation (Wet Granulation)

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Example L

Capsule Formulation

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |

-continued

| Item | Ingredients | mg/capsule | | | |
|---|---|---|---|---|---|
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

What is claimed is:
1. A method for the treatment of a c-met related cancer in a patient in need of such treatment, which comprises administering to the patient a pharmaceutically effective amount of a compound of formula (I) or a pharmaceutically acceptable salt thereof, wherein formula (1) is:

wherein:
X is selected from the group consisting of:
  (a) hydrogen;
  (b) $OR^1$;
  (c) $SR^2$;
  (d) $(SO)R^2$;
  (e) $(SO_2)R^2$; and
  (f) a group $A^1$—Q;
$A^1$ is a $C_1$–$C_3$-alkylen or $C_1$–$C_3$-alkyl group;
Q is selected from the group consisting of:
  (a) $OR^1$;
  (b) $SR^2$;
  (c) $SOR^2$;
  (d) $SO_2R^2$;
  (e) $NR^3R^4$;
  (f) $NHCH_2CH_2NR^3R^4$; and
  (g) halogen;
$R^1$ is selected from the group consisting of:
  (a) hydrogen;
  (b) $C_1$–$C_3$-alkyl;
  (c) allyl;
  (d) dimethylphosphonylmethyl;
  (e) 2,3-epoxy-1-propyl;
  (f) (R)-2,3-dihydroxy-1-propyl;
  (g) (S)-2,3-dihydroxy-1-propyl;
  (h) 1,3-dihydroxy-2-propyl;
  (i) 3-hydroxy-2-hydroxymethyl-1-propyl;
  (j) 2-methoxyethoxymethyl;
  (k) 2,2-dimethyl-1,3-dioxolan-4-ylmethyl; and
  (l) a group $A^1$—$Q^1$;

$Q^1$ is selected from the group consisting of:
 (a) $C_1$–$C_2$-alkoxy;
 (b) cyano;
 (c) carboxyl;
 (d) $C_1$–$C_6$-alkoxycarbonyl;
 (e) carboxamide;
 (f) —CO—$NR^3R^4$;
 (g) $C_1$–$C_6$-alkylsulfanyl;
 (h) $C_1$–$C_6$-alkylsulfenyl; and
 (i) $C_1$–$C_6$-alkylsulfonyl;
 with the proviso that if $A^1$ represents a 1,2-ethylen or 1,3-propylen group, then $Q^1$ is hydroxy or NR3R4;
$R^2$ is selected from the group consisting of:
 (a) $C_1$–$C_6$-alkyl;
 (b) dimethylphosphonylmethyl;
 (c) 2,3-epoxy-1-propyl;
 (d) 2,3-dihydroxy-1-propyl;
 (e) 2,2-dimethyl-1,3-dioxolan-4-ylmethyl; and
 (f) $A^1$—$Q^1$;
$R^3$ and $R^4$ are independently selected from the group consisting of:
 (a) hydrogen; and
 (b) $C_1$–$C_6$-alkyl; or
alternatively, $R^3$ and $R^4$ together form a 5 to 7 membered ring containing one or two heteroatoms, independently selected from the group consisting of N and O, wherein said ring is (a) saturated or unsaturated and (b) unsubstituted or substituted by a methyl group;
Y is selected from the group consisting of:
 (a) hydrogen; and
 (b) a group $A^2$—R;
$A^2$ is selected from the group consisting of:
 (a) an unsubstituted $C_1$–$C_5$-alkylen or $C_1$–$C_3$-alkyl;
 (b) substituted $C_1$–$C_5$-alkylen or $C_1$–$C_3$-alkyl, substituted by $C_1$–$C_6$-alkyl;
 (c) phenyl; and
 (d) hydroxy;
R is selected from the group consisting of:
 (a) hydroxy;
 (b) linear or branched $C_1$–$C_6$-alkoxy;
 (c) amino;
 (d) dimethylamino;
 (e) diethylamino;
 (f) t-butyloxycarbonylamino;
 (g) carboxyl;
 (h) $C_1$–$C_6$-alkoxycarbonyl;
 (i) triazolyl;
 (j) cyano;
 (k) piperidino;
 (l) 1-pyrrolidinyl;
 (m) morpholino;
 (n) 4-methylpiperazin-1-yl;
 (o) O—$A^1$—N $R^3R^4$;
 (p) S—$A^1$—$NR^3R^4$;
 (q) 4-carboxyphenyl;
 (r) furan-3-yl;
 (s) thiophen-2-yl; and
 (t) 3-methylthiophen-2-yl; and
Z represents one or two substituents independently selected from the group consisting of:
 (a) halogen;
 (b) hydroxy;
 (c) allyloxy;
 (d) methyl;
 (e) $C_1$–$C_5$-alkoxy;
 (f) methyoxymethoxy;
 (g) (2-methoxyethoxy)methyloxy;
 (h) methylthio;
 (i) ethoxymethoxy;
 (j) methylenedioxy;
 (k) ethynyl;
 (l) trimethylsilyethynyl;
 (m) unsubstituted benzyloxy; and
 (n) substituted benzyloxy substituted by halogen, methyoxy, cyano, nitro, methylenedioxy, carboxy, or ethoxy.

2. A method according to claim 1, wherein the cancer is non-small cell lung cancer.

3. A method according to claim 1, wherein the cancer is small cell lung cancer.

4. A method according to claim 1, wherein the cancer is breast cancer.

5. A method according to claim 1, wherein the cancer is colon cancer.

6. A method according to claim 1, wherein the cancer is prostate cancer.

7. A method according to claim 1, wherein the cancer is ovarian cancer.

8. A method according to claim 1, wherein the cancer is gastric cancer.

9. A method according to claim 1, wherein the cancer is human papillary renal carcinoma.

10. A method according to claim 1, wherein the cancer is metastatic head and neck squamous cell carcinoma.

11. A method according to claim 1, wherein the cancer is hapatocellular carcinoma.

12. A method according to claim 1, wherein:
 $R^1$ and $R^2$ are alkyl groups independently selected from the group consisting of:
  (a) methyl;
  (b) ethyl; and
  (c) propyl;
 $Q^1$ is methoxy or ethoxy;
 R and Z are alkoxy groups independently selected from the group consisting of:
  (a) methoxy;
  (b) ethoxy; and
  (c) isopropyloxy;
 $R^3$ and $R^4$ together form ring systems selected from the group consisting of:
  (a) 1-pyrrolidinyl-;
  (b) piperidino-;
  (c) morpholino-; and
  (d) 4-methylpiperazin-1-yl;
 X is located in the 4-position of the phenyl ring;
 Y is $A^2$—R selected from the group consisting of:
  (a) 2-hydroxyethyl;
  (b) 3-hydroxypropyl;
  (c) 2-methoxyethyl;
  (d) 3-methoxypropyl;
  (e) (R)-2,3-dihydroxy-1-propyl;
  (f) (S)-2,3-dihydroxy-1-propyl;
  (g) (R)-3-hydroxybutyl;
  (h) (S)-3-hydroxybutyl;
  (i) 2-morpholinoethyl;
  (j) 3-morpholinopropyl;
  (k) (CH2)$_3$COOH;
  (l) 3-(4-methylpiperazin-1-yl)ethyl;
  (m) 3-Hydroxy-2,2-dimethylpropyl;
  (n) 3-hydroxy-1-phenylpropyl;
  (o) 3-tert-butyloxyethyl;
  (p) 2-aminoethyl;

(q) 3-aminopropyl;
(r) 4-aminobutyl;
(s) 2-(N,N-dimethylamino)ethyl;
(t) 3-(N,N-dimethylamino)propyl;
(u) 3-(pyrrolidin-1-yl)propyl;
(v) CH$_2$COOH;
(w) (CH$_2$)$_2$COOH;
(x) CH(C$_2$H$_5$)COOH;
(y) (CH$_2$)$_3$COOC(CH$_3$)$_3$;
(z) (CH$_2$)$_2$—N—COOC(CH$_3$)$_3$;
(aa) (CH$_2$)$_3$—N—COOC(CH$_3$)$_3$;
(ab) (CH$_2$)$_2$—O—(CH$_2$)$_2$—N(CH$_3$)$_2$;
(ac) (CH$_2$)$_2$—O—(CH$_2$)$_2$—NH$_2$;
(ad) (CH$_2$)$_2$—S—(CH$_2$)$_2$—N(CH$_3$)$_2$;
(ae) (CH$_2$)$_2$—S—(CH$_2$)$_3$—N(CH$_3$)$_2$;
(af) (CH$_2$)$_3$—S—(CH$_2$)$_2$—N(CH$_3$)$_2$;
(ag) (CH$_2$)$_3$—S—(CH$_2$)$_3$—N(CH$_3$)$_2$;
(ah) (1,2,4-triazol-1-yl)ethyl; and
(ai) 3-(1,2,4-triazol-3-yl)propyl; and Z is located in the 3- or 4-position, with the proviso that if Z is benzyloxy or a substituted benzyloxy group, Z is located in the 3-position.

13. A method according to claim 1, wherein Z is selected from the group consisting of: 3-chloro; 4-chloro; 3-bromo; 3-iodo; 3-ethynyl; 3-methoxymethoxy; 3-(2-methoxyethoxy)methyloxy; 3-methylthio; 3-ethoxymethoxy; and 3,4-methylendioxy.

14. A method according to claim 1, wherein Z is unsubstituted 3-benzyloxy or substituted 3-benzyloxy; substituted by halogen, methoxy, cyano, nitro, methylendioxy, carboxy or ethoxy.

15. A method according to claim 1, wherein:

X is located in the 4-position of the phenyl ring and is hydrogen; OR$^1$; (SO)CH$_3$; (SO$_2$)CH$_3$; or a group CH$_2$—Q;

Q is OH; NR$^3$R$^4$ or NHCH$_2$CH$_2$NR$^3$R$^4$;

R$^1$ is selected from the group consisting of:
(a) hydrogen;
(b) dimethylphosphonylmethyl;
(c) (R)-2,3-dihydroxy-1-propyl;
(d) (S)-2,3-dihydroxy-1-propyl;
(e) 1,3-dihydroxy-2-propyl;
(f) 3-hydroxy-2-hydroxymethyl-1-propyl;
(g) 2-methoxyethoxymethyl;
(h) 2,2-dimethyl-1,3-dioxolan-4-ylmethyl; and
(i) a group A$^1$—Q$^1$ wherein A$^1$ is a methylene, ethylene or propylene group and Q$^1$ is cyano, carboxyl, carboxamide, or —CO—NR$^3$R$^4$;

Y is selected from the group consisting of:
(a) 2-hydroxyethyl;
(b) 3-hydroxypropyl;
(c) 2-methoxyethyl;
(d) 3-methoxypropyl;
(e) (R)-2,3-dihydroxy-1-propyl;
(f) (S)-2,3-dihydroxy-1-propyl;
(g) (R)-3-hydroxybutyl;
(h) (S)-3-hydroxybutyl;
(i) 3-hydroxy-2,2-dimethylpropyl;
(j) 2-morpholinoethyl;
(k) 3-morpholinopropyl;
(l) 2-(4-methylpiperazin-1-yl)ethyl;
(m) 3-hydroxy-1-phenylpropyl;
(n) 2-aminoethyl;
(o) 3-aminopropyl;
(p) 4-aminobutyl;
(q) 2-(N,N-dimethylamino)ethyl;
(r) 3-(N,N-dimethylamino)propyl;
(s) 3-(pyrrolidin-1-yl)propyl;
(t) CH$_2$COOH;
(u) (CH$_2$)$_2$COOH;
(v) (CH$_2$)$_3$COOH;
(w) CH(C$_2$H$_5$)COOH;
(x) (CH$_2$)$_2$—O—(CH$_2$)$_2$—N(CH$_3$)$_2$;
(y) (CH$_2$)$_2$—O—(CH$_2$)$_2$—NH$_2$;
(z) (CH$_2$)$_2$—S—(CH$_2$)$_2$—N(CH$_3$)$_2$;
(aa) (CH$_2$)$_2$—S—(CH$_2$)$_3$—N(CH$_3$)$_2$;
(ab) (CH$_2$)$_3$—S—(CH$_2$)$_2$—N(CH$_3$)$_2$; and
(ac) (CH$_2$)$_3$—S—(CH$_2$)$_3$—N(CH$_3$)$_2$; and Z is selected from the group consisting of:
(a) 3-chloro;
(b) 4-chloro;
(c) 3-bromo;
(d) 3-iodo;
(e) 3-ethynyl;
(f) 3-methoxymethoxy,
(g) unsubstituted 3-benzyloxy, and
(h) substituted 3-benzyloxy substituted by halogen, methoxy, cyano, nitro, methylendioxy, carboxy or ethoxy.

16. A method according to claim 1, wherein:

X is located in the 4-position of the phenyl ring and is selected from the group consisting of:
(a) hydrogen;
(b) OR$^1$;
(c) (SO)CH$_3$;
(d) (SO$_2$)CH$_3$; and
(e) a group CH$_2$—Q;

Q is selected from the group consisting of:
(a) OH;
(b) NR$^3$R$^4$; and
(c) NHCH$_2$CH$_2$NR$^3$R$^4$;

R$^1$ is selected from the group consisting of:
(a) hydrogen;
(b) dimethylphosphonylmethyl;
(c) (R)-2,3-dihydroxy-1-propyl;
(d) (S)-2,3-dihydroxy-1-propyl;
(e) 1,3-dihydroxy-2-propyl;
(f) 3-hydroxy-2-hydroxymethyl-1-propyl;
(g) 2-methoxyethoxymethyl; and
(h) and a group A$^1$—Q$^1$;

A$^1$ is selected from the group consisting of:
(a) methylene;
(b) ethylene; and
(c) propylene;

Q$^1$ is selected from the group consisting of: cyano; carboxyl; hydroxy; and NR$^3$R$^4$;

Y is selected from the group consisting of:
(a) 2-hydroxyethyl;
(b) 3-hydroxypropyl;
(c) (R)-2,3-dihydroxy-1-propyl;
(d) (S)-2,3-dihydroxy-1-propyl;
(e) 2-morpholinoethyl;
(f) 3-morpholinopropyl;
(g) 2-(4-methylpiperazin-1-yl)ethyl;
(h) 3-hydroxy-1-phenylpropyl;
(i) 2-aminoethyl;
(j) 3-aminopropyl;
(k) 2-(N,N-dimethylamino)ethyl;
(l) 3-(N,N-dimethylamino)propyl; and
(m) 3-(pyrrolidin-1-yl)propyl; and Z is selected from the group consisting of:
 (a) 3-chloro;
 (b) 4-chloro;
 (c) 3-bromo;
 (d) 3-iodo;
 (e) 3-ethynyl;
 (f) 3-methoxymethoxy;
 (g) unsubstituted 3-benzyloxy; and
 (h) substituted 3-benzyloxy, substituted by halogen, methoxy, or cyano.

* * * * *